US006455288B1

(12) United States Patent
Jakobovits et al.

(10) Patent No.: US 6,455,288 B1
(45) Date of Patent: Sep. 24, 2002

(54) HOMOGENEOUS IMMUNOASSAYS USING MUTANT GLUCOSE-6-PHOSPHATE DEHYDROGENASES

(75) Inventors: Edward Benjamin Jakobovits, Menlo Park; Joy L. Silen, Belmont; Mark J. Levy, San Jose; Thomas C. Goodman, Mountain View; Martin Becker, Palo Alto; Edwin F. Ullman, Atherton; Robert M. Caldwell, San Carlos; Richard R. Bott, Burlingame; Christopher Charles Barnett, South San Francisco, all of CA (US)

(73) Assignees: Dade Behring Marburg GmbH, Marburg (DE); Genencor International, Inc., San Francisco, CA (US)

( * ) Notice: Subject to any disclaimer, the term of this patent is extended or adjusted under 35 U.S.C. 154(b) by 0 days.

(21) Appl. No.: 08/044,857

(22) Filed: Apr. 8, 1993

(51) Int. Cl.[7] .......................... C12N 15/52; C12N 15/63; C12N 1/21

(52) U.S. Cl. ................. 435/190; 435/252.3; 435/320.1; 536/23.2

(58) Field of Search ..................... 435/26, 190, 252.3, 435/252.33, 320.1; 536/22.1, 23.1, 23.2, 23.7

(56) References Cited

U.S. PATENT DOCUMENTS

| | | | |
|---|---|---|---|
| 3,817,837 A | 6/1974 | Rubenstein et al. | .. 195/103.5 R |
| 3,935,074 A | 1/1976 | Rubenstein et al. | .. 195/103.5 R |
| 4,233,401 A | 11/1980 | Yoshida et al. | ................. 435/7 |
| 4,727,022 A | 2/1988 | Skold et al. | .................... 435/7 |

FOREIGN PATENT DOCUMENTS

| | | |
|---|---|---|
| CA | 2045838 A1 | 1/1992 |
| EP | 0 154276 | 9/1985 |
| EP | 0 469 523 | 2/1992 |
| EP | 0 487301 | 5/1992 |
| EP | 487 301 A1 * | 5/1992 |
| WO | WO 92/07078 | 4/1992 |

OTHER PUBLICATIONS

Adams, et al., The Journal of Biological Chemistry, (May 10, 1983) vol. 258:9, pp. 5867–5868, "Crystallization and preliminary X–ray data for glucose–6–phosphate dehydrogenase from *Leuconosoc mesenteroides*".
Barnell, et al., Journal of Bacteriology, (Dec. 1990) vol. 172:12, pp. 7227–7240, "Sequence and genetic organization of a *Zymomonas mobillis* gene cluster that encodes several enzymes of glucose metabolism".

Bhadbhade, et al., Febs Lett, (Jan. 1987) vol. 211:2 pp. 243–246, "Sequence indentity between a lysine–containing peptide from *Leuconostoc mesenteroides* glucose–6–phosphate dehydrogenase and an active site peptide from human erythrocte glucose–6–phosphate dehydrogenase".
Gasser, et al., International Journal of Systematic Bacteriology, (Jan. 1977) vol. 27, pp. 6–8, "Immunological relationships of glucose–6–phosphate dehydrogenase of Leuconostoc mesenteroides NCDO 768 (=ATCC 12291)".
Haghighi, et al., Biochemistry, (1982) vol. 21:25, pp. 6415–6420, "Glucose–6–phosphate dehydrogenease from *Leuconostoc mesenteroides*".
Heilmann, et al., Eur. Journal Biochemistry, (1988) vol. 174, pp. 485–490, "Identification and isolation of glucose dehydrogenase genes of *Bacillus megaterium* M1286 and their expression in *Escherichia coli*".
Hey, et al., Biochem. Journal, (1983) vol. 209, pp. 363–371 Tandem dye–ligand chromatography and biospecific elution applied to the purification of glucose–6–phosphate dehydrogenase from *Leuconostoc mesenteroides*.
Hontebeyrie, et al., Int. Journal Systematic Bacteriology, (Jan. 1975) vol. 25:1, pp. 1–6, "Comparative immunological relationships of two distinct sets of isofunctional dehydrogenases in the genus Leuconostoc".
Ishaque, et al., Biochemical and Biophysical Research Communications, (1974) vol. 59:3, pp. 894–901, "On the Absence of cysteine in glucose–6–phosphate from *Leuconostoc mesenteroides*".
Jeffery, et al., Biochemistry, (1985) vol. 24, pp. 666–671, Glucose–6–phosphate dehydrogenase from *Saccharomyces cerevisiae*: characterization of a reactive lysine residue labeled with acetylsalicylic acid.

(List continued on next page.)

Primary Examiner—Christine J. Saoud
(74) Attorney, Agent, or Firm—Theodore J Leitereg; Patrick G. Gattari

(57) ABSTRACT

The present invention relates to methods for immunoassay of analytes employing mutant glucose-6-phosphate dehydrogenase (G6PDH) enzymes as labels. In particular, the invention relates-to the use of conjugates of an analyte or analyte analog and a mutant $NAD^+$ dependent G6PDH differing from any precursor G6PDH by the deletion, substitution, or insertion, or any combination thereof of at least one amino acid per subunit. The invention also involves the construction of several mutations in precursor glucose-6-phosphate dehydrogenase (G6PDH) enzymes. Typically, the mutations involve deletion or substitution of one or more lysine residues, or introduction of one or more cysteine residues by insertion of cysteine to precursor G6PDH or substitution of precursor G6PDH amino acids residues with cysteine. The present invention also relates to conjugates of the subject enzymes and specific binding pair members, kits useful in performing the methods of the invention, cell lines producing the subject enzymes, DNA sequences encoding the subject enzymes, and vectors containing DNA encoding the subject enzymes and designed to allow a host cell to produce the subject enzymes.

9 Claims, 16 Drawing Sheets

OTHER PUBLICATIONS

Jeffery, et al., Biochemical and Biophysical Research Communications, (May 15, 1989) vol. 160:3, pp 1290–1295, "Glucose–6–phosphate dehydrogenase: characterization of a reactive lysine in the Pichia jadinii enzyme reveals a limited structural variation in a functionally significant segment".

Lee, et al., Journal of Biological Chemistry, (Jul. 15, 1991) vol. 266:20, pp 13028–13034, "Cloning of the gene and amino acid sequence for glucose for glucose–6–phosphate dehydrogenease from Leuconostoc mesenteroides".

Lee, et al., Protein Science, (1992) vol. 1, pp. 329–334, "Lysine–21 of Leuconostoc mesenteroides glucose 6–phosphate dehydrogenase participates in substrate binding though charge–charge interaction".

Levy, H.R., Advances in Enzymology, (1979) vol. 48, pp. 97–192, "Glucose–6–phosphate dehydrogenases".

Murphy, et al., Journal of Bacteriology, (Jan. 1987) vol. 169:1, pp. 334–339, "Expression of the gene for $NAD^+$–dependent glucose–6–phosphate dehydrogenase from Lueconostoc mesenteroides cloned in Escherichia coli K–12".

Olive, et al., Biochemistry, (Mar. 1967) vol. 6:3, pp. 730–736, "The preparation and some properties of crystalline glucose 6–phosphate dehydrogenase from Leuconostoc mesenteroides".

Rowley, et al., Journal of Bacteriology, (Feb. 1991) vol. 173:3, pp. 968–977 "Molecular characterization of the Escherichia coli K–12 zwf gene encoding glucose–6–phosphate dehydrogenase".

Skold, et al., Journal of Immunology, (May 15, 1987) vol. 138, pp. 3408–3414 "Monoclonal antibodies to glucose–6–phosphate dehydrogenase (G6PDH) form cyclic 1:1 complexes with G6PDH and act as regulatory subunits".

* cited by examiner

| | | | | | |
|---|---|---|---|---|---|
| GCGCTATAAT | GAAAAGTGAA | TTTAACTAAA | AATAAGGGGT | ACATCATGGT | TTCAGAAATC | 60
| AAGACGTTAG | TAACTTTCTT | TGGTGGCACT | GGTGACTTGG | CCAAGCGTAA | GCTTTACCCA | 120
| TCAGTTTTCA | ATCTTTATAA | AAAAGGCTAC | TTGCAAAAGC | ATTTTGCCAT | TGTTGGAACG | 180
| GCCCGTCAAG | CCCTCAATGA | TGACGAATTC | AAACAATTGG | TTCGTGATTC | AATTAAAGAT | 240
| TTCACTGACG | ATCAAGCACA | AGCTGAGGCG | TTCATCGAAC | ATTTCTCATA | CCGTGCACAC | 300
| GACGTAACAG | ATGCTGCTTC | ATACGCTGTT | TTAAAAGAGG | CGATTGAAGA | AGCTGCCGAC | 360
| AAATTTGATA | TCGATGGCAA | CCGCATTTTC | TATATGTCAG | TTGCGCCACG | TTTCTTTGGT | 420
| ACAATTGCCA | AATATCTTAA | GTCAGAAGGC | CTACTAGCTG | ACACTGGTTA | CAACCGTTTG | 480
| ATGATTGAAA | AGCCTTTCGG | TACATCATAT | GACACAGCTG | CCGAACTCCA | AAATGACTTG | 540
| GAAAACGCAT | TTGATGATAA | CCAACTATTC | CGTATTGACC | ACTACCTTGG | TAAGGAAATG | 600
| GTTCAAAACA | TTGCTGCCCT | TCGCTTTGGT | AACCCAATTT | CGATGCTGC | TTGGAACAAG | 660
| GATTACATCA | GAACGTTCA | AGTAACATTG | TCAGAAGTCT | TGGGTGTCGA | AGAACGTGCC | 720
| GGCTACTATG | ACACAGCCGG | TGCATTGCTC | GACATGATTC | AAAACCACAC | CATGCAAATT | 780
| GTTGGTTGGT | TAGCCATGGA | AAAACCAGAA | TCATTCACTG | ACAAAGACAT | TCGTGCCGCT | 840
| AAAAACGCAG | CCTTTAATGC | TTTGAAGATC | TATGATGAAG | CAGAAGTTAA | CAAATACTTT | 900
| GTTCGTGCAC | AATATGGTGC | CGGTGATTCA | GCTGACTTCA | AGCCATACCT | TGAAGAATTA | 960
| GACGTACCTG | CTGATTCTAA | AAACAATACC | TTCATCGCCG | GCGAATTGCA | ATTTGATTTG | 1020
| CCACGTTGGG | AGGGTGTCCC | ATTCTATGTC | CGTTCAGGTA | AGCGCTTAGC | TGCTAAACAG | 1080
| ACACGGGTTG | ATATCGTCTT | TAAGGCTGGC | ACGTTAACT | TTGGTTCAGA | ACAAGAAGCA | 1140
| CAAGAAGCTG | TCTTGTCAAT | TATCATTGAT | CCAAAGGGTG | CTATCGAATT | GAAGTTGAAC | 1200
| GCTAAGTCAG | TTGAAGATGC | TTTCAACACA | CGTACAATTG | ACTTAGGTTG | GACTGTATCT | 1260
| GACGAAGATA | AGAAGAACAC | GCCAGAACCA | TACGAACGTA | TGATTCACGA | CACTATGAAT | 1320
| GGTGATGGCT | CTAACTTCGC | TGACTGGAAT | GGCGTTTCAA | TCGCTTGGAA | GTTCGTTGAT | 1380
| GCTATTTCAG | CCGTTTATAC | CGCAGATAAA | GCACCACTTG | AAACTTACAA | GTCGGGCTCA | 1440
| ATGGGTCCTG | AAGCATCCGA | TAAATTATTG | GCTGCCAATG | GTGATGCTTG | GGTGTTTAAA | 1500
| GGTTAA | | | | | | 1506

FIG. 1

```
Val Ser Glu Ile Lys Thr Leu Val Thr Phe Phe Gly Gly Thr Gly Asp
 1           5               10                  15
Leu Ala Lys Arg Lys Leu Tyr Pro Ser Val Phe Asn Leu Tyr Lys Lys
            20              25                  30
Gly Tyr Leu Gln Lys His Phe Ala Ile Val Gly Thr Ala Arg Gln Ala
            35              40                  45
Leu Asn Asp Asp Glu Phe Lys Gln Leu Val Arg Asp Ser Ile Lys Asp
 50                  55                  60
Phe Thr Asp Asp Gln Ala Gln Ala Glu Ala Phe Ile Glu His Phe Ser
 65                  70                  75                  80
Tyr Arg Ala His Asp Val Thr Asp Ala Ala Ser Tyr Ala Val Leu Lys
            85                  90                  95
Glu Ala Ile Glu Glu Ala Ala Asp Lys Phe Asp Ile Asp Gly Asn Arg
            100                 105                 110
Ile Phe Tyr Met Ser Val Ala Pro Arg Phe Phe Gly Thr Ile Ala Lys
        115                 120                 125
Tyr Leu Lys Ser Glu Gly Leu Leu Ala Asp Thr Gly Tyr Asn Arg Leu
        130                 135                 140
Met Ile Glu Lys Pro Phe Gly Thr Ser Tyr Asp Thr Ala Ala Glu Leu
 145                150                 155                 160
Gln Asn Asp Leu Glu Asn Ala Phe Asp Asp Asn Gln Leu Phe Arg Ile
            165                 170                 175
Asp His Tyr Leu Gly Lys Glu Met Val Gln Asn Ile Ala Ala Leu Arg
            180                 185                 190
Phe Gly Asn Pro Ile Phe Asp Ala Ala Trp Asn Lys Asp Tyr Ile Lys
        195                 200                 205
Asn Val Gln Val Thr Leu Ser Glu Val Leu Gly Val Glu Glu Arg Ala
 210                 215                 220
Gly Tyr Tyr Asp Thr Ala Gly Ala Leu Leu Asp Met Ile Gln Asn His
 225                 230                 235                 240
Thr Met Gln Ile Val Gly Trp Leu Ala Met Glu Lys Pro Glu Ser Phe
            245                 250                 255
Thr Asp Lys Asp Ile Arg Ala Ala Lys Asn Ala Ala Phe Asn Ala Leu
        260                 265                 270
Lys Ile Tyr Asp Glu Ala Glu Val Asn Lys Tyr Phe Val Arg Ala Gln
        275                 280                 285
```

FIG. 2A

```
Tyr Gly Ala Gly Asp Ser Ala Asp Phe Lys Pro Tyr Leu Glu Glu Leu
    290             295             300
Asp Val Pro Ala Asp Ser Lys Asn Asn Thr Phe Ile Ala Gly Glu Leu
305             310             315             320
Gln Phe Asp Leu Pro Arg Trp Glu Gly Val Pro Phe Tyr Val Arg Ser
            325             330             335
Gly Lys Arg Leu Ala Ala Lys Gln Thr Arg Val Asp Ile Val Phe Lys
            340             345             350
Ala Gly Thr Phe Asn Phe Gly Ser Glu Gln Glu Ala Gln Glu Ala Val
        355             360             365
Leu Ser Ile Ile Ile Asp Pro Lys Gly Ala Ile Glu Leu Lys Leu Asn
    370             375             380
Ala Lys Ser Val Glu Asp Ala Phe Asn Thr Arg Thr Ile Asp Leu Gly
385             390             395             400
Trp Thr Val Ser Asp Glu Asp Lys Lys Asn Thr Pro Glu Pro Tyr Glu
            405             410             415
Arg Met Ile His Asp Thr Met Asn Gly Asp Gly Ser Asn Phe Ala Asp
            420             425             430
Trp Asn Gly Val Ser Ile Ala Trp Lys Phe Val Asp Ala Ile Ser Ala
        435             440             445
Val Tyr Thr Ala Asp Lys Ala Pro Leu Glu Thr Tyr Lys Ser Gly Ser
    450             455             460
Met Gly Pro Glu Ala Ser Asp Lys Leu Leu Ala Ala Asn Gly Asp Ala
465             470             475             480
Trp Val Phe Lys Gly
            485
```

FIG. 2B

| | |
|---|---:|
| AATCCGTTTG TGAAAATAGG TACTTTTTAA ATGATTTTGC GTTATAATGG TAAATGAATT | 60 |
| TAATTATAGT ATTAAGGGGA ACATCATGGT TGCAGAAATC AAAACATTAG TTACTTTTTT | 120 |
| TGGTGGAACT GGTGATTTAG CAAAGCGTAA GCTTTATCCT TCAGTTTTTA ACCTTTACAA | 180 |
| GAAAGGTTAC TTACAAGAAC ATTTTGCCAT TGTTGGTACA GCACGTCAGG ATTTGACTGA | 240 |
| TGCTGAATTC AAGCAATTGG TTCGCGAATC AATCGCTGAC TTTACTGAAG ATAAAGCCCA | 300 |
| AGCCGAGGCC TTCATCGCAC ACTTTTCATA CCGTGCACAT GATGTAACCG ATGCAGCTTC | 360 |
| ATACAACATC TTAAAACAAG CAATTGAAGA AGCAGCCGAA AAGTTCGATA TTCAAGGTAA | 420 |
| TCGTATTTTC TACATGTCTG TGGCACCACG ATTCTTTGGG ACAATTGCAA ATATCTCAA | 480 |
| GTCAGAGGGT TTGCTAGCTG ATAGTGGTTA CAACCGTTTG ATGATTGAAA AGCCTTTTGG | 540 |
| TACATCATAC GCCACTGCCG AAGAGCTACA AAAAGACTTA GAAAACGCTT TTGACGATAA | 600 |
| TCAATTATTC CGTATTGATC ATTATCTTGG TAAAGAAATG GTCCAAAATA TTGCTGCCCT | 660 |
| TCGTTTTGGT AACCCCATCT TTGATGCCGC TTGGAACAAA GATTACATTA AAAACGTCCA | 720 |
| AGTTACTTTG TCTGAAGTGC TTGGTGTTGA AGAACGTGCC GGTTATTACG ATACAGCCGG | 780 |
| TGCATTATTA GATATGATTC AAAACCACAC TATGCAAATT GTTGGTTGGC TTGCTATGGA | 840 |
| AAAGCCAGAT TCATTTACTG ATAAGGATAT CCGTGCGGCT AAGAATGCGG CTTTTAATGC | 900 |
| TCTTAAAATT TATGATGAAG CCGAAGTCAA CAAGTATTTC GTCCGTGCAC AGTATGGTGC | 960 |
| CGGAGACACT GCTGATTTCA AGCCATATCT TGAAGAAATG GACGTACCCG CTGACTCAAA | 1020 |
| GAACAATACA TTCATCGCTG GTGAATTACA GTTTGATTTG CCACGTTGGG AAGGTGTGCC | 1080 |
| ATTCTACGTG CGTTCAGGCA AGCGTTTAGC TGCTAAACAA ACACGTGTCG ATATCGTCTT | 1140 |
| CAAGGCTGGT ACCTTTGCCT TTGGTTCTGA ACAAGAAGCG CAAGAAGCTG TGTTATCAAT | 1200 |
| TTTGATTGAT CCTAAGGGTG GTATCGAATT CAAGATTAAT TCAAAGTCAG TTGAAGATGC | 1260 |
| TTTCAATACA CGTATGATTA ATCTTGATTG GTCAATTTCT GATGAAGATA AGCAAAATAC | 1320 |
| ACCTGAGCCA TACGAACGTA TGATTCACGA CACAATGAAT GGTGACGGAT CAAACTTCGC | 1380 |
| TGACTGGAAC GGTGTTGCTA TTGCTTGGAA GTTTGTGGAT GCTATTTCAG CTGTCTACAC | 1440 |
| TGCTGATAAA GCACCACTTG AAACATACAA GTCAGGTTCC ATGGGACCTG AAGCATCTGA | 1500 |
| CAAGCTGTTA GCCGAAAACG GTGACGCTTG GGTATTTAAG GGTTAATAAA ATAAAAAAAG | 1560 |
| AAGACTAGCT T | 1571 |

FIG. 3

```
Val Ala Glu Ile Lys Thr Leu Val Thr Phe Phe Gly Gly Thr Gly Asp
1                5                    10                  15

Leu Ala Lys Arg Lys Leu Tyr Pro Ser Val Phe Asn Leu Tyr Lys Lys
            20                  25                  30

Gly Tyr Leu Gln Glu His Phe Ala Ile Val Gly Thr Ala Arg Gln Asp
        35                  40                  45

Leu Thr Asp Ala Glu Phe Lys Gln Leu Val Arg Glu Ser Ile Ala Asp
    50                  55                  60

Phe Thr Glu Asp Lys Ala Gln Ala Glu Ala Phe Ile Ala His Phe Ser
65                  70                  75                  80

Tyr Arg Ala His Asp Val Thr Asp Ala Ala Ser Tyr Asn Ile Leu Lys
            85                  90                  95

Gln Ala Ile Glu Glu Ala Ala Glu Lys Phe Asp Ile Gln Gly Asn Arg
            100                 105                 110

Ile Phe Tyr Met Ser Val Ala Pro Arg Phe Phe Gly Thr Ile Ala Lys
        115                 120                 125

Tyr Leu Lys Ser Glu Gly Leu Leu Ala Asp Ser Gly Tyr Asn Arg Leu
    130                 135                 140

Met Ile Glu Lys Pro Phe Gly Thr Ser Tyr Ala Thr Ala Glu Glu Leu
145                 150                 155                 160

Gln Lys Asp Leu Glu Asn Ala Phe Asp Asp Asn Gln Leu Phe Arg Ile
            165                 170                 175

Asp His Tyr Leu Gly Lys Glu Met Val Gln Asn Ile Ala Ala Leu Arg
            180                 185                 190

Phe Gly Asn Pro Ile Phe Asp Ala Ala Trp Asn Lys Asp Tyr Ile Lys
            195                 200                 205

Asn Val Gln Val Thr Leu Ser Glu Val Leu Gly Val Glu Glu Arg Ala
    210                 215                 220

Gly Tyr Tyr Asp Thr Ala Gly Ala Leu Leu Asp Met Ile Gln Asn His
225                 230                 235                 240

Thr Met Gln Ile Val Gly Trp Leu Ala Met Glu Lys Pro Asp Ser Phe
            245                 250                 255

Thr Asp Lys Asp Ile Arg Ala Ala Lys Asn Ala Ala Phe Asn Ala Leu
        260                 265                 270

Lys Ile Tyr Asp Glu Ala Glu Val Asn Lys Tyr Phe Val Arg Ala Gln
    275                 280                 285
```

FIG. 4A

```
Tyr Gly Ala Gly Asp Thr Ala Asp Phe Lys Pro Tyr Leu Glu Glu Met
    290             295             300
Asp Val Pro Ala Asp Ser Lys Asn Asn Thr Phe Ile Ala Gly Glu Leu
305             310             315                         320
Gln Phe Asp Leu Pro Arg Trp Glu Gly Val Pro Phe Tyr Val Arg Ser
            325             330             335
Gly Lys Arg Leu Ala Ala Lys Gln Thr Arg Val Asp Ile Val Phe Lys
            340             345             350
Ala Gly Thr Phe Ala Phe Gly Ser Glu Gln Glu Ala Gln Glu Ala Val
        355             360             365
Leu Ser Ile Leu Ile Asp Pro Lys Gly Gly Ile Glu Phe Lys Ile Asn
    370             375             380
Ser Lys Ser Val Glu Asp Ala Phe Asn Thr Arg Met Ile Asn Leu Asp
385             390             395                         400
Trp Ser Ile Ser Asp Glu Asp Lys Gln Asn Thr Pro Glu Pro Tyr Glu
            405             410             415
Arg Met Ile His Asp Thr Met Asn Gly Asp Gly Ser Asn Phe Ala Asp
            420             425             430
Trp Asn Gly Val Ala Ile Ala Trp Lys Phe Val Asp Ala Ile Ser Ala
        435             440             445
Val Tyr Thr Ala Asp Lys Ala Pro Leu Glu Thr Tyr Lys Ser Gly Ser
    450             455             460
Met Gly Pro Glu Ala Ser Asp Lys Leu Leu Ala Glu Asn Gly Asp Ala
465             470             475                         480
Trp Val Phe Lys Gly
            485
```

FIG. 4B

```
ATGGTTGCAG AAATCAAGAC GTTAGTCACA TTTTTCGGTG CTACTGGTGA TTTGGCAAAG      60
CGTAAGCTTT ACCCATCAGT TTTTAACCTC TTCAAGAAAG GTTATTTGCA AGAACATTTC     120
GCCATTGTTG AACAGCCCG TCAAGACTTG ACTGAAGATG AATTCAAGCA ACTTGTGCGA     180
GACTCANNNN NNNNNNNNNN NNNNNNNNNN NNNCAAGCCG AAGCATTCAT TGAACACTTC     240
TCATATCGTG CCCATGACGT TACGGATGCA GCGTCATACA GCGTTTTGAA GTCAGCAATC     300
GAAGAAGCTT CTGACAAGTT TGGCATTGAT GGTAACCGTA TCTTCTATAT GTCTGTTGCT     360
CCACGTTTCT TTGGGACGAT TGCAAAGTAT TTGAAGTCAG AAGGTTTGTT GGCCACAACT     420
GGTTACAACC GTTTGATGAT CGAAAAGCCA TTTGGGACAT CATACGAAAC AGCTGAAAAG     480
TTGCAAAACG AATTGGAAAA CGCCTTTGAT GATGACCAAT TGTTCCGTAT TGACCACTAC     540
CTTGGTAAGG AAATGGTCCA AAATATTGCG GCTTTGCGTT TTGGTAACCC AATCTTTGAT     600
GCAGCCTGGA ACAAGGACTA CATCAAGAAC GTGCAAGTGA CATTGTCAGA AGTCTTGGGT     660
GTTGAAGAAC GTGCCGGTTA CTATGATACA GCCGGTGCTT TGCTCGACAT GATTCAAAAC     720
CACACGATGC AAATCGTCGG TTGGTTGGCC ATGGAAAAAC CTGACTCATT CACTGACAAG     780
GATATCCGTG CCGCTAAGAA CGCTGCCTTC AACGCTTTGA AGATTTACAA CGAAGAAGAA     840
GTTAACAAGT ACTTCGTTCG TGGCCAATAT GCAGGTGGTG ATTCTGCTGA ATTCAAGCCA     900
TATCTTGAAG AAATGGACGT ACCTGCTGAC TCAAAGAACA ACACGTACAT CGCTGGTGAA     960
TTGCAATTTG ATTTGCCACG TTGGGAAGGT GTGCCATTCT ACGTGCGTTC AGGTAAGCGC    1020
CTAGCTGCTA AGCAAACACG TATTGATATC NNNNNNNNNN NNNNNNNNNN NNNNNNNNNN    1080
NNNNNNNNNG AAGCCCAAGA AGCTATCTTG TCAATTTTGG TTGATCCAAC AGGTGGTATC    1140
GAATTCAAGA TCAATTCAAA GTCAGTTGAA NNNNNNNNNN NNNNNCGTCT CATCGGCCTT    1200
GATTGGCAAG TGTCAGAAGA AGACAAGCTT AACACACCTG AACCATACGA ACGTATGATT    1260
CATGACACGA TGAACGGTGA TGGTTCAAAC TTCGCCGATT GGAACGGTGT TGCCATTGCT    1320
TGGAAGTTCG TTGATGCGAT TTCAGCTGTT TACACCGCTG ATAAGGCACC ACTTGAAACT    1380
TACAAGTCTG GTTCAATGGG ACCAGCCGCA GCTGACAAGT TGTTGGCAAA TAACGGTGAT    1440
GCTTGGGTGT TTAAAGGTTA A                                              1461
```

FIG. 5

```
Val Ala Glu Ile Lys Thr Leu Val Thr Phe Phe Gly Ala Thr Gly Asp
1               5                   10                  15

Leu Ala Lys Arg Lys Leu Tyr Pro Ser Val Phe Asn Leu Phe Lys Lys
                20                  25                  30

Gly Tyr Leu Gln Glu His Phe Ala Ile Val Gly Thr Ala Arg Gln Asp
            35                  40                  45

Leu Thr Glu Asp Glu Phe Lys Gln Leu Val Arg Asp Ser Ile Ala Asp
        50                  55                  60

Ala Ala Asp Asp Lys Ala Gln Ala Glu Ala Phe Ile Glu His Phe Ser
65                  70                  75                  80

Tyr Arg Ala His Asp Val Thr Asp Ala Ala Ser Tyr Ser Val Leu Lys
                85                  90                  95

Ser Ala Ile Glu Glu Ala Ser Asp Lys Phe Gly Ile Asp Gly Asn Arg
            100                 105                 110

Ile Phe Tyr Met Ser Val Ala Pro Arg Phe Phe Gly Thr Ile Ala Lys
        115                 120                 125

Tyr Leu Lys Ser Glu Gly Leu Leu Ala Thr Thr Gly Tyr Asn Arg Leu
    130                 135                 140

Met Ile Glu Lys Pro Phe Gly Thr Ser Tyr Glu Thr Ala Glu Lys Leu
145                 150                 155                 160

Gln Asn Glu Leu Glu Asn Ala Phe Asp Asp Gln Leu Phe Arg Ile
                165                 170                 175

Asp His Tyr Leu Gly Lys Glu Met Val Gln Asn Ile Ala Ala Leu Arg
                180                 185                 190

Phe Gly Asn Pro Ile Phe Asp Ala Ala Trp Asn Lys Asp Tyr Ile Lys
            195                 200                 205

Asn Val Gln Val Thr Leu Ser Glu Val Leu Gly Val Glu Glu Arg Ala
    210                 215                 220

Gly Tyr Tyr Asp Thr Ala Gly Ala Leu Leu Asp Met Ile Gln Asn His
225                 230                 235                 240

Thr Met Gln Ile Val Gly Trp Leu Ala Met Glu Lys Pro Asp Ser Phe
                245                 250                 255

Thr Asp Lys Asp Ile Arg Ala Ala Lys Asn Ala Ala Phe Asn Ala Leu
            260                 265                 270

Lys Ile Tyr Asn Glu Glu Glu Val Asn Lys Tyr Phe Val Arg Gly Gln
        275                 280                 285
```

FIG. 6A

```
Tyr Ala Gly Gly Asp Ser Ala Glu Phe Lys Pro Tyr Leu Glu Glu Met
        290                 295                 300
Asp Val Pro Ala Asp Ser Lys Asn Asn Thr Tyr Ile Ala Gly Glu Leu
305                 310                 315                 320
Gln Phe Asp Leu Pro Arg Trp Glu Gly Val Pro Phe Tyr Val Arg Ser
                325                 330                 335
Gly Lys Arg Leu Ala Ala Lys Gln Thr Arg Ile Asp Ile Val Phe Lys
                340                 345                 350
Ala Gly Thr Phe Gln Phe Gly Ala Ala Gln Glu Ala Gln Glu Ala Ile
            355                 360                 365
Leu Ser Ile Leu Val Asp Pro Thr Gly Gly Ile Glu Phe Lys Ile Asn
        370                 375                 380
Ser Lys Ser Val Glu Asp Asp Phe Asn Thr Arg Leu Ile Gly Leu Asp
385                 390                 395                 400
Trp Gln Val Ser Glu Glu Asp Lys Leu Asn Thr Pro Glu Pro Tyr Glu
                405                 410                 415
Arg Met Ile His Asp Thr Met Asn Gly Asp Gly Ser Asn Phe Ala Asp
                420                 425                 430
Trp Asn Gly Val Ala Ile Ala Trp Lys Phe Val Asp Ala Ile Ser Ala
            435                 440                 445
Val Tyr Thr Ala Asp Lys Ala Pro Leu Glu Thr Tyr Lys Ser Gly Ser
        450                 455                 460
Met Gly Pro Ala Ala Ala Asp Lys Leu Leu Ala Asn Asn Gly Asp Ala
465                 470                 475                 480
Trp Val Phe Lys Gly
                485
```

FIG. 6B

```
TCTAGTCATT TAATCAATTT TTGACTTGTT CAACGCTTAA TATGTTTGTG AATCCCGTAC    60
TTTTCCAGAC CTTTTTGCGT TATAATGGAG AGTGAATTTA ATTATAATAT AAGGGGAACA   120
TCATGGTTTC AGAAATCAAA ACGTTGGTAA CTTTCTTTGG CGGAACTGGT GATTTAGCAA   180
AGCGTAAGCT TTACCCATCA GTTTTCAACC TCTACAAAAA AGGATACTTA CAAGAACACT   240
TTGCCATTGT TGGGACAGCA CGTCAACAAT TAAGTGATGA CGAGTTTAAG CAATTGGTTC   300
GTGATTCAAT TAAAGACTTT ACTGAAGATC AAGCACAAGC CGAAGCGTTT ATTGCGCATT   360
TTTCTTACCG TGCGCACGAT GTCACAGATG CCGCTTCTTA TGGTATCTTG AAGTCAGCGA   420
TCGAAGAAGC AGCAACCAAA TTTGACATTG ATGGCAATCG TATTTTCTAT ATGTCAGTTG   480
CCCCTCGTTT CTTCGGTACA ATCGCTAAAT ATTTGAAATC AGAAGGTTTG CTAGCTGAGA   540
CTGGCTACAA TCGTTTGATG ATTGAAAAGC CTTTTGGTAC ATCATACGCC ACCGCAGAAG   600
AATTGCAAAG TGATTTGGAA AATGCATTTG ATGATGACCA ACTGTTCCGT ATTGACCACT   660
ATCTTGGAAA AGAAATGGTA CAAAATATTG CAGCATTACG TTTTGGTAAC CCAATCTTTG   720
ATGCCGCTTG GAATAAGGAC TATATCAAAA ACGTACAAGT AACTTTGGCT GAAGTTCTAG   780
GTGTTGAAGA GCGTGCTGGT TACTACGATA CCACTGGCGC CCTTTTGGAT ATGATTCAAA   840
ACCACACAAT GCAAATTGTT GGTTGGTTAG CAATGGAAAA ACCTGAATCA TTCAATGATA   900
AGGATATCCG TGCAGCTAAA AACGCCGCCT TCAATGCATT AAAGATTTAT AACGAAGAAG   960
AAGTGAATAA GTACTTCGTT CGTGCACAAT ATGGTGCTGG TGATACAGCT GATTACAAGC  1020
CATATTTGGA AGAAGCAGAT GTCCCTGCTG ACTCAAAGAA CAACACATTC ATTGCTGGTG  1080
AATTGCAGTT CGATTTGCCA CGTTGGGAAG GTGTTCCTTT CTATGTTCGT TCAGGTAAGC  1140
GTTTGGCTGC CAAGCAAACA CGTGTTGATA TTGTATTTAA GGCTGGCACA TTCAACTTTG  1200
GTTCAGAACA AGAAGCACAA GAATCAGTAC TCTCAATCAT CATTGATCCA AAGGGTGCTA  1260
TTGAATTGAA GCTTAACGCT AAGTCAGTTG AAGATGCCTT CAACACCCGC ACAATCAACT  1320
TGGATTGGGC AGTATCTGAT GAAGACAAGA AGAACACACC AGAACCATAC GAACGTATGA  1380
TTCACGATAC AATGAATGGT GACGGATCAA ACTTTGCTGA TTGGAACGGT GTATCAATTG  1440
CTTGGAAGTT TGTTGACGCA ATTACTGCCG TTTACGATGC AGATAAAGCA CCATTGGAGA  1500
CATATAAGTC AGGTTCAATG GGTCCTGAAG CATCAGACAA GCTATTAGCT GAAAATGGCG  1560
ATGCTTGGGT ATTTAAAGGA TAAGCACATT TAAAAGACC ATCAAACAAA TCTTTGTTTG  1620
ACGGTCTTTT TATATTGTCT GATTTAAGAT GCGTTTGGTT TCACGGAAAA CGGCTGACAA  1680
ATTGGTGTAT TGATCC                                                  1696
```

FIG. 7

| | | | | | | | | | | | | | | |
|---|---|---|---|---|---|---|---|---|---|---|---|---|---|---|
| Met 1 | Val | Ser | Glu | Ile 5 | Lys | Thr | Leu | Val | Phe 10 | Phe | Gly | Gly | Thr 15 | Gly |
| Asp | Leu | Ala | Lys 20 | Arg | Lys | Leu | Tyr | Pro 25 | Ser | Val | Phe | Asn | Leu 30 | Tyr | Lys |
| Lys | Gly | Tyr 35 | Leu | Gln | Glu | His | Phe 40 | Ala | Ile | Val | Gly | Thr 45 | Ala | Arg | Gln |
| Gln | Leu 50 | Ser | Asp | Asp | Glu | Phe 55 | Lys | Gln | Leu | Val | Arg 60 | Asp | Ser | Ile | Lys |
| Asp 65 | Phe | Thr | Glu | Asp | Gln 70 | Ala | Gln | Ala | Glu | Ala 75 | Phe | Ile | Ala | His | Phe 80 |
| Ser | Tyr | Arg | Ala | His 85 | Asp | Val | Thr | Asp | Ala 90 | Ala | Ser | Tyr | Gly | Ile 95 | Leu |
| Lys | Ser | Ala | Ile | Glu 100 | Glu | Ala | Ala | Thr 105 | Lys | Phe | Asp | Ile | Asp 110 | Gly | Asn |
| Arg | Ile | Phe 115 | Tyr | Met | Ser | Val | Ala 120 | Pro | Arg | Phe | Phe | Gly 125 | Thr | Ile | Ala |
| Lys | Tyr 130 | Leu | Lys | Ser | Glu | Gly 135 | Leu | Leu | Ala | Glu | Thr 140 | Gly | Tyr | Asn | Arg |
| Leu 145 | Met | Ile | Glu | Lys | Pro 150 | Phe | Gly | Thr | Ser | Tyr 155 | Ala | Thr | Ala | Glu | Glu 160 |
| Leu | Gln | Ser | Asp | Leu 165 | Glu | Asn | Ala | Phe | Asp 170 | Asp | Gln | Leu | Phe 175 | Arg |
| Ile | Asp | His | Tyr 180 | Leu | Gly | Lys | Glu | Met 185 | Val | Gln | Asn | Ile | Ala 190 | Ala | Leu |
| Arg | Phe | Gly 195 | Asn | Pro | Ile | Phe | Asp 200 | Ala | Ala | Trp | Asn | Lys 205 | Asp | Tyr | Ile |
| Lys | Asn 210 | Val | Gln | Val | Thr | Leu 215 | Ala | Glu | Val | Leu | Gly 220 | Val | Glu | Glu | Arg |
| Ala 225 | Gly | Tyr | Tyr | Asp | Thr 230 | Thr | Gly | Ala | Leu | Leu 235 | Asp | Met | Ile | Gln | Asn 240 |
| His | Thr | Met | Gln | Ile 245 | Val | Gly | Trp | Leu | Ala 250 | Met | Glu | Lys | Pro | Glu 255 | Ser |
| Phe | Asn | Asp | Lys 260 | Asp | Ile | Arg | Ala | Ala 265 | Lys | Asn | Ala | Ala | Phe 270 | Asn | Ala |
| Leu | Lys | Ile 275 | Tyr | Asn | Glu | Glu | Glu 280 | Val | Asn | Lys | Tyr | Phe 285 | Val | Arg | Ala |

FIG. 8A

```
    Gln Tyr Gly Ala Gly Asp Thr Ala Asp Tyr Lys Pro Tyr Leu Glu Glu
            290                 295                 300

Ala Asp Val Pro Ala Asp Ser Lys Asn Asn Thr Phe Ile Ala Gly Glu
    305                 310                 315                 320

Leu Gln Phe Asp Leu Pro Arg Trp Glu Gly Val Pro Phe Tyr Val Arg
                    325                 330                 335

Ser Gly Lys Arg Leu Ala Ala Lys Gln Thr Arg Val Asp Ile Val Phe
                    340                 345                 350

Lys Ala Gly Thr Phe Asn Phe Gly Ser Glu Gln Glu Ala Gln Glu Ser
                    355                 360                 365

Val Leu Ser Ile Ile Ile Asp Pro Lys Gly Ala Ile Glu Leu Lys Leu
            370                 375                 380

Asn Ala Lys Ser Val Glu Asp Ala Phe Asn Thr Arg Thr Ile Asn Leu
    385                 390                 395                 400

Asp Trp Ala Val Ser Asp Glu Asp Lys Lys Asn Thr Pro Glu Pro Tyr
                    405                 410                 415

Glu Arg Met Ile His Asp Thr Met Asn Gly Asp Gly Ser Asn Phe Ala
                    420                 425                 430

Asp Trp Asn Gly Val Ser Ile Ala Trp Lys Phe Val Asp Ala Ile Thr
                    435                 440                 445

Ala Val Tyr Asp Ala Asp Lys Ala Pro Leu Glu Thr Tyr Lys Ser Gly
            450                 455                 460

Ser Met Gly Pro Glu Ala Ser Asp Lys Leu Leu Ala Glu Asn Gly Asp
    465                 470                 475                 480

Ala Trp Val Phe Lys Gly
                    485
```

FIG. 8B

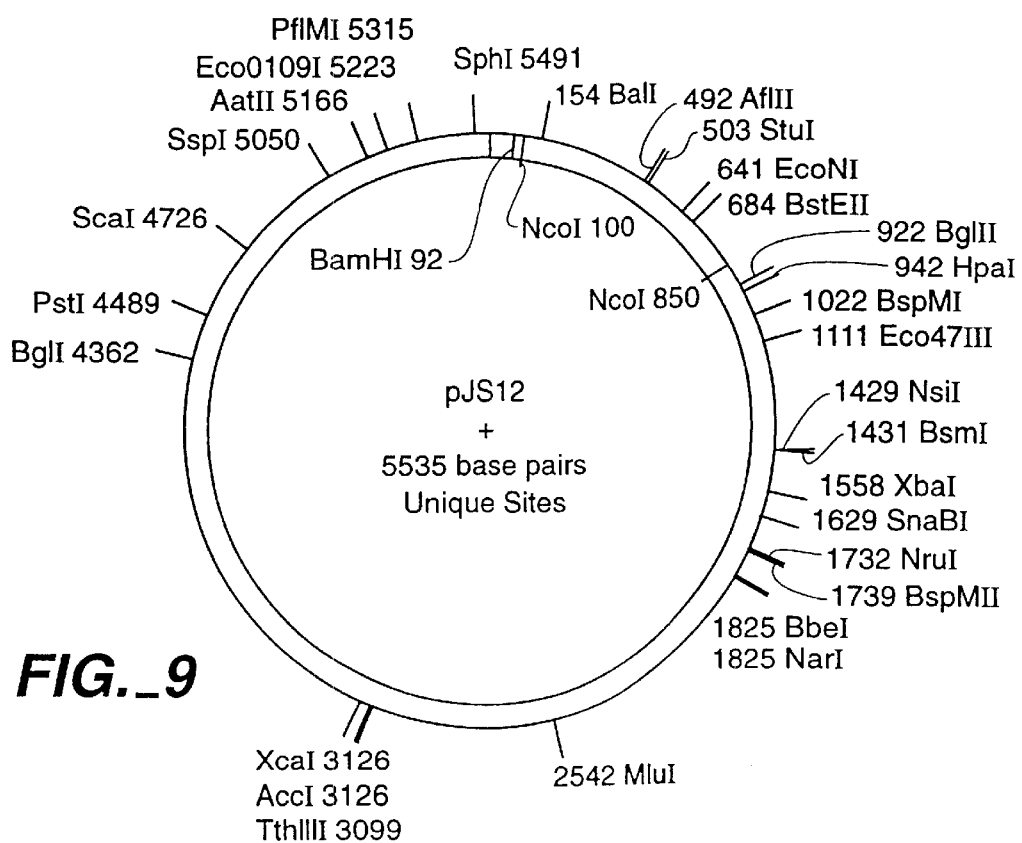
FIG._9

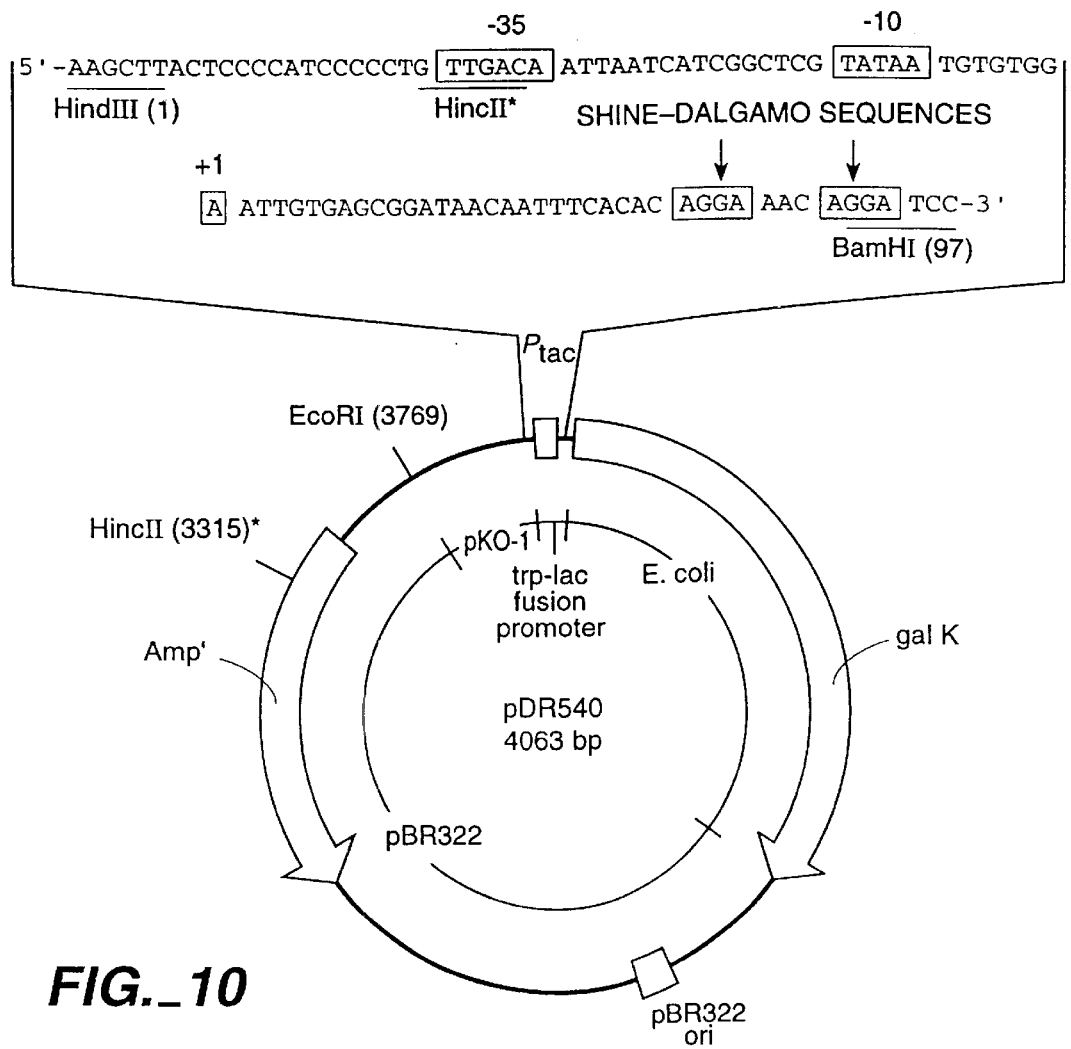
FIG._10

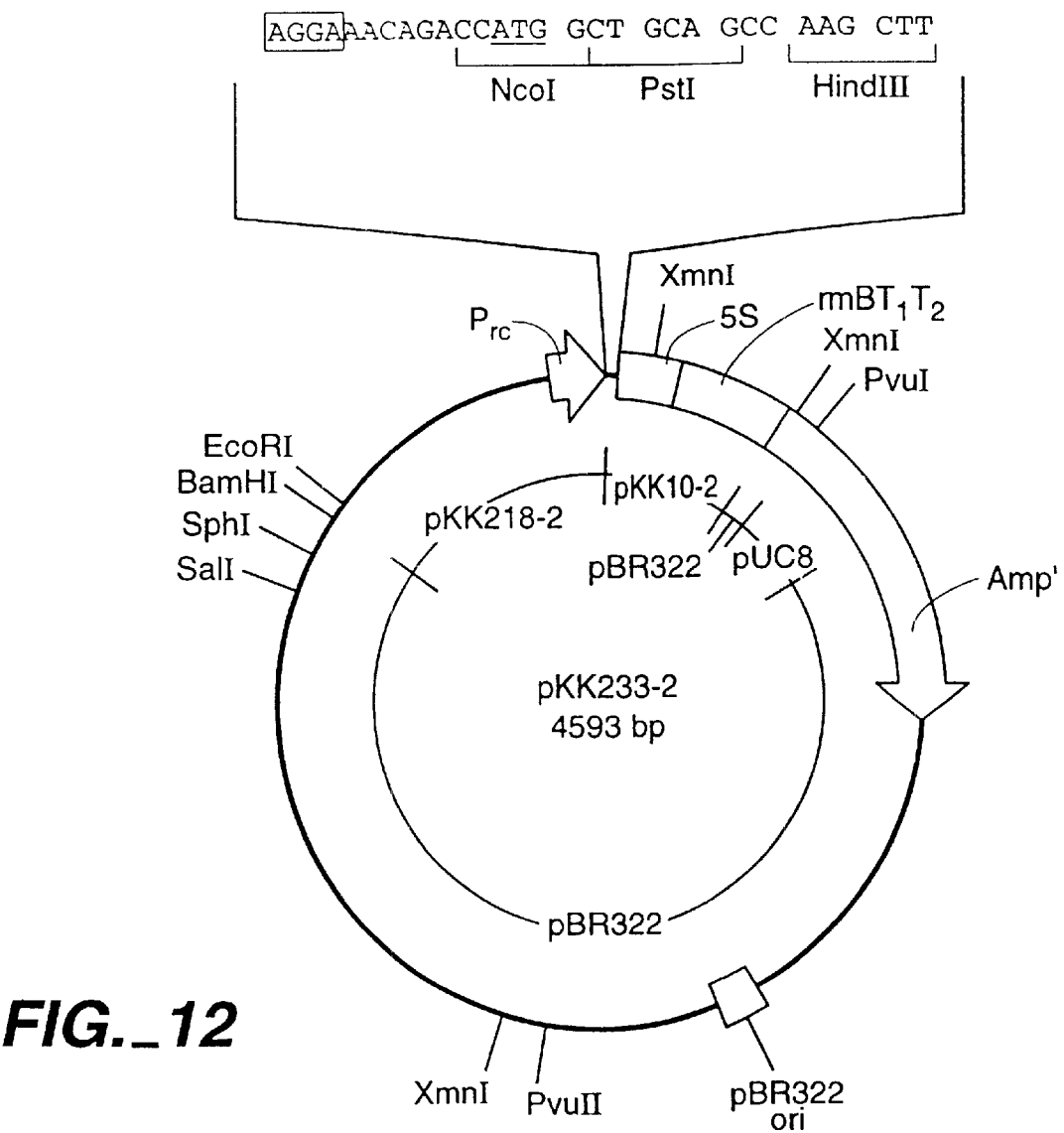
FIG._12

SEQUENCE LISTING (1) GENERAL INFORMATION:

(iii) NUMBER OF SEQUENCES: 124

(2) INFORMATION FOR SEQ ID NO:1:

(i) SEQUENCE CHARACTERISTICS:
      (A) LENGTH: 65 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Leuconostoc citreum
      (B) STRAIN: ATCC 3351

(xi) SEQUENCE DESCRIPTION: SEQ ID NO:1:

CATGGTTGCA GAAATCAAAA CATTAGTTAC TTTTTTTGGT GGAACTGGTG ATTTAGCAAA     60

GCGTA     65

(2) INFORMATION FOR SEQ ID NO:2:

(i) SEQUENCE CHARACTERISTICS:
      (A) LENGTH: 485 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Leuconostoc mesenteroides
      (B) STRAIN: ATCC 12291

(xi) SEQUENCE DESCRIPTION: SEQ ID NO:2:

```
Val Ser Glu Ile Lys Thr Leu Val Thr Phe Phe Gly Gly Thr Gly Asp
 1               5                  10                  15

Leu Ala Lys Arg Lys Leu Tyr Pro Ser Val Phe Asn Leu Tyr Lys Lys
            20                  25                  30

Gly Tyr Leu Gln Lys His Phe Ala Ile Val Gly Thr Ala Arg Gln Ala
        35                  40                  45

Leu Asn Asp Asp Glu Phe Lys Gln Leu Val Arg Asp Ser Ile Lys Asp
    50                  55                  60

Phe Thr Asp Asp Gln Ala Gln Ala Glu Ala Phe Ile Glu His Phe Ser
65                  70                  75                  80

Tyr Arg Ala His Asp Val Thr Asp Ala Ala Ser Tyr Ala Val Leu Lys
                85                  90                  95

Glu Ala Ile Glu Glu Ala Ala Asp Lys Phe Asp Ile Asp Gly Asn Arg
            100                 105                 110

Ile Phe Tyr Met Ser Val Ala Pro Arg Phe Phe Gly Thr Ile Ala Lys
        115                 120                 125

Tyr Leu Lys Ser Glu Gly Leu Leu Ala Asp Thr Gly Tyr Asn Arg Leu
    130                 135                 140
```

```
Met Ile Glu Lys Pro Phe Gly Thr Ser Tyr Asp Thr Ala Ala Glu Leu
145                 150                 155                 160

Gln Asn Asp Leu Glu Asn Ala Phe Asp Asn Gln Leu Phe Arg Ile
            165                 170                 175

Asp His Tyr Leu Gly Lys Glu Met Val Gln Asn Ile Ala Ala Leu Arg
            180                 185                 190

Phe Gly Asn Pro Ile Phe Asp Ala Ala Trp Asn Lys Asp Tyr Ile Lys
            195                 200                 205

Asn Val Gln Val Thr Leu Ser Glu Val Leu Gly Val Glu Glu Arg Ala
            210                 215                 220

Gly Tyr Tyr Asp Thr Ala Gly Ala Leu Leu Asp Met Ile Gln Asn His
225                 230                 235                 240

Thr Met Gln Ile Val Gly Trp Leu Ala Met Glu Lys Pro Glu Ser Phe
                245                 250                 255

Thr Asp Lys Asp Ile Arg Ala Ala Lys Asn Ala Ala Phe Asn Ala Leu
            260                 265                 270

Lys Ile Tyr Asp Glu Ala Glu Val Asn Lys Tyr Phe Val Arg Ala Gln
            275                 280                 285

Tyr Gly Ala Gly Asp Ser Ala Asp Phe Lys Pro Tyr Leu Glu Glu Leu
290                 295                 300

Asp Val Pro Ala Asp Ser Lys Asn Asn Thr Phe Ile Ala Gly Glu Leu
305                 310                 315                 320

Gln Phe Asp Leu Pro Arg Trp Glu Gly Val Pro Phe Tyr Val Arg Ser
            325                 330                 335

Gly Lys Arg Leu Ala Ala Lys Gln Thr Arg Val Asp Ile Val Phe Lys
            340                 345                 350

Ala Gly Thr Phe Asn Phe Gly Ser Glu Gln Glu Ala Gln Glu Ala Val
            355                 360                 365

Leu Ser Ile Ile Ile Asp Pro Lys Gly Ala Ile Glu Leu Lys Leu Asn
            370                 375                 380

Ala Lys Ser Val Glu Asp Ala Phe Asn Thr Arg Thr Ile Asp Leu Gly
385                 390                 395                 400

Trp Thr Val Ser Asp Glu Asp Lys Lys Asn Thr Pro Glu Pro Tyr Glu
                405                 410                 415

Arg Met Ile His Asp Thr Met Asn Gly Asp Gly Ser Asn Phe Ala Asp
            420                 425                 430

Trp Asn Gly Val Ser Ile Ala Trp Lys Phe Val Asp Ala Ile Ser Ala
            435                 440                 445

Val Tyr Thr Ala Asp Lys Ala Pro Leu Glu Thr Tyr Lys Ser Gly Ser
450                 455                 460

Met Gly Pro Glu Ala Ser Asp Lys Leu Leu Ala Ala Asn Gly Asp Ala
465                 470                 475                 480

Trp Val Phe Lys Gly
            485

(2) INFORMATION FOR SEQ ID NO:3:

(i) SEQUENCE CHARACTERISTICS:
        (A) LENGTH: 1458 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (vi) ORIGINAL SOURCE:
        (A) ORGANISM: Leuconostoc citreum
        (B) STRAIN: NCIMB 3351

(xi) SEQUENCE DESCRIPTION: SEQ ID NO:3:

| | | | | | |
|---|---|---|---|---|---|
| GTTGCAGAAA | TCAAAACATT | AGTTACTTTT | TTTGGTGGAA | CTGGTGATTT | AGCAAAGCGT | 60 |
| AAGCTTTATC | CTTCAGTTTT | TAACCTTTAC | AAGAAAGGTT | ACTTACAAGA | ACATTTTGCC | 120 |
| ATTGTTGGTA | CAGCACGTCA | GGATTTGACT | GATGCTGAAT | TCAAGCAATT | GGTTCGCGAA | 180 |
| TCAATCGCTG | ACTTTACTGA | AGATAAAGCC | AAGCCGAGG | CCTTCATCGC | ACACTTTTCA | 240 |
| TACCGTGCAC | ATGATGTAAC | CGATGCAGCT | TCATACAACA | TCTTAAAACA | AGCAATTGAA | 300 |
| GAAGCAGCCG | AAAAGTTCGA | TATTCAAGGT | AATCGTATTT | CTACATGTC | TGTGGCACCA | 360 |
| CGATTCTTTG | GGACAATTGC | AAAATATCTC | AAGTCAGAGG | GTTTGCTAGC | TGATAGTGGT | 420 |
| TACAACCGTT | TGATGATTGA | AAAGCCTTTT | GGTACATCAT | ACGCCACTGC | CGAAGAGCTA | 480 |
| CAAAAAGACT | TAGAAAACGC | TTTTGAGCAT | AATCAATTAT | TCCGTATTGA | TCATTATCTT | 540 |
| GGTAAAGAAA | TGGTCCAAAA | TATTGCTGCC | CTTCGTTTTG | GTAACCCCAT | CTTTGATGCC | 600 |
| GCTTGGAACA | AAGATTACAT | TAAAAACGTC | CAAGTTACTT | TGTCTGAAGT | GCTTGGTGTT | 660 |
| GAAGAACGTG | CCGGTTATTA | CGATACAGCC | GGTGCATTAT | TAGATATGAT | TCAAAACCAC | 720 |
| ACTATGCAAA | TTGTTGGTTG | GCTTGCTATG | GAAAAGCCAG | ATTCATTTAC | TGATAAGGAT | 780 |
| ATCCGTGCGG | CTAAGAATGC | GGCTTTTAAT | GCTCTTAAAA | TTTATGATGA | AGCCGAAGTC | 840 |
| AACAAGTATT | TCGTCCGTGC | ACAGTATGGT | GCCGGAGACA | CTGCTGATTT | CAAGCCATAT | 900 |
| CTTGAAGAAA | TGGACGTACC | CGCTGACTCA | AGAACAATA | CATTCATCGC | TGGTGAATTA | 960 |
| CAGTTTGATT | TGCCACGTTG | GGAAGGTGTG | CCATTCTACG | TGCGTTCAGG | CAAGCGTTTA | 1020 |
| GCTGCTAAAC | AAACACGTGT | CGATATCGTC | TTCAAGGCTG | GTACCTTTGC | CTTTGGTTCT | 1080 |
| GAACAAGAAG | CGCAAGAAGC | TGTGTTATCA | ATTTTGATTG | ATCCTAAGGG | TGGTATCGAA | 1140 |
| TTCAAGATTA | ATTCAAAGTC | AGTTGAAGAT | GCTTTCAATA | CACGTATGAT | TAATCTTGAT | 1200 |
| TGGTCAATTT | CTGATGAAGA | TAACGAAAAT | ACACCTGAGC | CATACGAACG | TATGATTCAC | 1260 |
| GACACAATGA | ATGGTGACGG | ATCAAACTTC | GCTGACTGGA | ACGGTGTTGC | TATTGCTTGG | 1320 |
| AAGTTTGTGG | ATGCTATTTC | AGCTGTCTAC | ACTGCTGATA | AGCACCACT | TGAAACATAC | 1380 |
| AAGTCAGGTT | CCATGGGACC | TGAAGCATCT | GACAAGCTGT | TAGCCGAAAA | CGGTGACGCT | 1440 |
| TGGGTATTTA | AGGGTTAA | | | | | 1458 |

(2) INFORMATION FOR SEQ ID NO:4:

(i) SEQUENCE CHARACTERISTICS:
        (A) LENGTH: 485 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Leuconostoc citreum
        (B) STRAIN: NCIMB 3351

(xi) SEQUENCE DESCRIPTION: SEQ ID NO:4:

-continued

```
Val Ala Glu Ile Lys Thr Leu Val Thr Phe Phe Gly Gly Thr Gly Asp
1               5                   10                  15

Leu Ala Lys Arg Lys Leu Tyr Pro Ser Val Phe Asn Leu Tyr Lys Lys
                20                  25                  30

Gly Tyr Leu Gln Glu His Phe Ala Ile Val Gly Thr Ala Arg Gln Asp
            35                  40                  45

Leu Thr Asp Ala Glu Phe Lys Gln Leu Val Arg Glu Ser Ile Ala Asp
        50                  55                  60

Phe Thr Glu Asp Lys Ala Gln Ala Glu Ala Phe Ile Ala His Phe Ser
65                  70                  75                  80

Tyr Arg Ala His Asp Val Thr Asp Ala Ala Ser Tyr Asn Ile Leu Lys
                85                  90                  95

Gln Ala Ile Glu Glu Ala Ala Glu Lys Phe Asp Ile Gln Gly Asn Arg
            100                 105                 110

Ile Phe Tyr Met Ser Val Ala Pro Arg Phe Phe Gly Thr Ile Ala Lys
            115                 120                 125

Tyr Leu Lys Ser Glu Gly Leu Leu Ala Asp Ser Gly Tyr Asn Arg Leu
        130                 135                 140

Met Ile Glu Lys Pro Phe Gly Thr Ser Tyr Ala Thr Ala Glu Glu Leu
145                 150                 155                 160

Gln Lys Asp Leu Glu Asn Ala Phe Asp Asp Asn Gln Leu Phe Arg Ile
                165                 170                 175

Asp His Tyr Leu Gly Lys Glu Met Val Gln Asn Ile Ala Ala Leu Arg
            180                 185                 190

Phe Gly Asn Pro Ile Phe Asp Ala Ala Trp Asn Lys Asp Tyr Ile Leu
            195                 200                 205

Asn Val Gln Val Thr Leu Ser Glu Val Leu Gly Val Glu Glu Arg Ala
210                 215                 220

Gly Tyr Tyr Asp Thr Ala Gly Ala Leu Leu Asp Met Ile Gln Asn His
225                 230                 235                 240

Thr Met Gln Ile Val Gly Trp Leu Ala Met Glu Lys Pro Asp Ser Phe
                245                 250                 255

Thr Asp Lys Asp Ile Arg Ala Ala Lys Asn Ala Ala Phe Asn Ala Leu
            260                 265                 270

Leu Ile Tyr Asp Glu Ala Glu Val Asn Leu Tyr Phe Val Arg Ala Gln
        275                 280                 285

Tyr Gly Ala Gly Asp Thr Ala Asp Phe Lys Pro Tyr Leu Glu Glu Met
        290                 295                 300

Asp Val Pro Ala Asp Ser Leu Asn Asn Thr Phe Ile Ala Gly Glu Leu
305                 310                 315                 320

Glu Phe Asp Leu Pro Arg Trp Glu Gly Val Pro Phe Tyr Val Arg Ser
                325                 330                 335

Gly Lys Arg Leu Ala Ala Lys Gln Thr Arg Val Asp Ile Val Phe Lys
            340                 345                 350

Ala Gly Thr Phe Ala Phe Gly Ser Glu Gln Glu Ala Gln Glu Ala Val
        355                 360                 365

Leu Ser Ile Leu Ile Asp Pro Lys Gly Gly Ile Glu Phe Lys Ile Asn
        370                 375                 380

Ser Lys Ser Val Glu Asp Ala Phe Asn Thr Arg Met Ile Asn Leu Asp
385                 390                 395                 400

Trp Ser Ile Ser Asp Glu Asp Lys Gln Asn Thr Pro Glu Pro Tyr Glu
                405                 410                 415
```

```
Arg Met Ile His Asp Thr Met Asn Gly Asp Gly Ser Asn Phe Ala Asp
        420                 425                 430

Trp Asn Gly Val Ala Ile Ala Trp Lys Phe Val Asp Ala Ile Ser Ala
        435                 440                 445

Val Tyr Thr Ala Asp Lys Ala Pro Leu Glu Thr Tyr Lys Ser Gly Ser
450                 455                 460

Met Gly Pro Glu Ala Ser Asp Lys Leu Leu Ala Glu Asn Gly Asp Ala
465                 470                 475                 480

Trp Val Phe Lys Gly
            485

(2) INFORMATION FOR SEQ ID NO:5:

(i) SEQUENCE CHARACTERISTICS:
        (A) LENGTH: 1458 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc lactis
         (B) STRAIN: NCDO 546

(xi) SEQUENCE DESCRIPTION: SEQ ID NO:5:

GTTGCAGAAA TCAAGACGTT AGTCACATTT TTCGGTGCTA CTGGTGATTT GGCAAAGCGT      60

AAGCTTTACC CATCAGTTTT TAACCTCTTC AAGAAAGGTT ATTTGCAAGA ACATTTCGCC     120

ATTGTTGGAA CAGCCCGTCA AGACTTGACT GAAGATGAAT TCAAGCAACT TCTGCGAGAC     180

TCANNNNNNN NNNNNNNNNN NNNNNNNNNN CAAGCCGAAG CATTCATTGA ACACTTCTCA     240

TATCGTGCCC ATGACGTTAC GGATGCAGCG TCATACAGCG TTTTGAAGTC AGCAATCGAA     300

GAAGCTTCTG ACAAGTTTGG CATTGATGGT AACCGTATCT CTATATGTC TGTTGCTCCA      360

CGTTTCTTTG GGACGATTGC AAAGTATTTG AAGTCAGAAG GTTTGTTGGC ACAACTGGT      420

TACAACCGTT TGATGATCGA AAAGCCATTT GGGACATCAT ACGAAACAGC TGAAAAGTTG     480

CAAAACGAAT TGGAAAACGC CTTTGATGAT GACCAATTGT TCCGTATTGA CCACTACCTT     540

GGTAAGGAAA TGGTCCCAAA TATTGCGGCT TTGCGTTTTG GTAACCCAAT CTTTGATGCA     600

GCCTGGAACA AGGACTACAT CAAGAACGTG CAAGTGACAT TGTCAGAAGT CTTGGGTGTT     660

GAAGAACGTG CCGGTTACTA TGATACAGCC GGTGCTTTGC TCGACATGAT TCAAAACCAC     720

ACGATGCAAA TCGTCGGTGG GTTGGCCATG GAAAAACCTG ACTCATTCAC TGACAAGGAT     780

ATCCGTGCCG CTAAGAACGC TGCCTTCAAC GCTTTGAAGA TTTACAACGA AGAAGAAGTT     840

AACAAGTACT TCCTTCGTGG CCAATATGCA GGTGGTGATT CTGCTGAATT CAAGCCATAT     900

CTTGAAGAAA TGGACGTACC TGCTGACTCA AGAACAACA CGTACATCGC TGGTGAATTG      960

CAATTTGATT TGCCACGTTG GGAAGGTGTG CCATTCTACG TGCGTTCAGG TAAGCGCCTA    1020

GCTGCTAAGC AAACACGTAT TGATATCNNN NNNNNNNNNN NNNNNNNNNN NNNNNNNNNN    1080

NNNNNNGAAG CCCAAGAAGC TATCTTGTCA ATTTTGGTTG ATCCAACAGG TGGTATCGAA    1140

TTCAAGATCA ATTCAAAGTC AGTTGAANNN NNNNNNNNNN NNCGTCTCAT CGGCCTTGAT    1200

TGGCAAGTGT CAGAAGAAGA CAAGCTTAAC ACACCTGAAC CATACGAACG TATGATTCAT    1260

GACACGATGA ACGGTGATGG TTCAAACTTC GCCGATTGGA ACGGTGTTGC CATTGCTTGG    1320
```

```
AAGTTCGTTG ATGCGATTTC AGCTGTTTAC ACCGCTGATA AGGCACCACT TGAAACTTAC      1380

AAGTCTGGTT CAATGGGACC AGCCGCAGCT GACAAGTTGT TGGCAAATAA CGGTGATGCT      1440

TGGGTGTTTA AAGGTTAA                                                    1458
```

(2) INFORMATION FOR SEQ ID NO:6:

(i) SEQUENCE CHARACTERISTICS:
        (A) LENGTH: 485 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Leuconostoc lactis
        (B) STRAIN: NCDO 546

(xi) SEQUENCE DESCRIPTION: SEQ ID NO:6:

```
Val Ala Glu Ile Lys Thr Leu Val Thr Phe Phe Gly Ala Thr Gly Asp
1               5                   10                  15

Leu Ala Lys Arg Lys Leu Thr Pro Ser Val Phe Asn Leu Phe Lys Lys
            20                  25                  30

Gly Tyr Leu Gln Glu His Phe Ala Ile Val Gly Thr Ala Arg Gln Asp
        35                  40                  45

Leu Thr Glu Asp Glu Phe Lys Gln Leu Val Arg Asp Ser Ile Ala Asp
    50                  55                  60

Ala Ala Asp Asp Lys Ala Gln Ala Glu Ala Phe Ile Glu His Phe Ser
65                  70                  75                  80

Tyr Arg Ala His Asp Val Thr Asp Ala Ala Ser Tyr Ser Val Leu Lys
                85                  90                  95

Ser Ala Ile Glu Glu Ala Ser Asp Lys Phe Gly Ile Asp Gly Asn Arg
            100                 105                 110

Ile Phe Tyr Met Ser Val Ala Pro Arg Phe Gly Thr Ile Ala Lys
        115                 120                 125

Tyr Leu Lys Ser Glu Gly Leu Leu Ala Thr Thr Gly Tyr Asn Arg Leu
    130                 135                 140

Met Ile Glu Lys Pro Phe Gly Thr Ser Tyr Glu Thr Ala Glu Lys Leu
145                 150                 155                 160

Gln Asn Glu Leu Glu Asn Ala Phe Asp Asp Asn Leu Phe Arg Ile
                165                 170                 175

Asp His Tyr Leu Gly Leu Glu Met Val Gln Asn Ile Ala Ala Leu Arg
            180                 185                 190

Phe Gly Asn Pro Ile Phe Asp Ala Ala Trp Asn Leu Asp Tyr Ile Leu
        195                 200                 205

Asn Val Gln Val Thr Leu Ser Glu Val Leu Gly Val Glu Glu Arg Ala
    210                 215                 220

Gly Tyr Tyr Asp Thr Ala Gly Ala Leu Leu Asp Met Ile Gln Asn His
225                 230                 235                 240

Thr Met Gln Ile Val Gly Trp Leu Ala Met Glu Lys Pro Asp Ser Phe
                245                 250                 255

Thr Asp Lys Asp Ile Arg Ala Ala Lys Asn Ala Ala Phe Asn Ala Leu
            260                 265                 270
```

```
Leu Ile Tyr Asn Glu Glu Val Asn Leu Tyr Phe Val Arg Gly Gln
        275                 280                 285

Tyr Ala Gly Gly Asp Ser Ala Glu Phe Leu Pro Tyr Leu Glu Glu Met
        290                 295                 300

Asp Val Pro Ala Asp Ser Lys Asn Asn Thr Tyr Ile Ala Gly Gly Leu
305                 310                 315                 320

Gln Phe Asp Leu Pro Arg Trp Glu Gly Val Pro Phe Tyr Val Arg Ser
                325                 330                 335

Gly Lys Arg Leu Ala Ala Lys Gln Thr Arg Ile Asp Ile Val Phe Leu
            340                 345                 350

Ala Gly Thr Phe Gln Phe Gly Ala Ala Gln Glu Ala Gln Glu Ala Ile
        355                 360                 365

Leu Ser Ile Leu Val Asp Pro Thr Gly Gly Ile Glu Phe Lys Ile Asn
        370                 375                 380

Ser Leu Ser Val Glu Asp Asp Phe Asn Thr Arg Leu Ile Gly Leu Asp
385                 390                 395                 400

Trp Gln Val Ser Glu Glu Asp Lys Leu Asn Thr Pro Glu Pro Tyr Gly
                405                 410                 415

Arg Met Ile His Asp Thr Met Asn Gly Asp Gly Ser Asn Phe Ala Asp
                420                 425                 430

Trp Asn Gly Val Ala Ile Ala Trp Lys Phe Val Asp Ala Ile Ser Ala
            435                 440                 445

Val Tyr Thr Ala Asp Lys Ala Pro Leu Glu Thr Tyr Lys Ser Gly Ser
        450                 455                 460

Met Gly Pro Ala Ala Ala Asp Lys Leu Leu Ala Asn Asn Gly Asp Ala
465                 470                 475                 480

Trp Val Phe Lys Gly
            485

(2) INFORMATION FOR SEQ ID NO:7:

(i) SEQUENCE CHARACTERISTICS:
        (A) LENGTH: 1458 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc dextranicum
        (B) STRAIN: ATCC 19255

(xi) SEQUENCE DESCRIPTION: SEQ ID NO:7:

ATGGTTTCAG AAATCAAAAC GTTGGTAACT TTCTTTGGCG AACTGGTGA TTTAGCAAAG      60

CGTAAGCTTT ACCCATCAGT TTTCAACCTC TACAAAAAAG GATACTTACA AGAACACTTT    120

GCCATTGTTG GGACAGCACG TCAACAATTA AGTGATGACG AGTTTAAGCA ATTGGTTCGT    180

GATTCAATTA AAGACTTTAC TGAAGATCAA GCACAAGCCG AAGCGTTTAT TGCGCATTTT    240

TCTTACCGTG CGCACGATGT CACAGATGCC GCTTCTTATG GTATCTTGAA GTCAGCGATC    300

GAAGAAGCAG CAACCAAATT TGACATTGAT GGCAATCGTA TTTTCTATAT GTCAGTTGCC    360

CCTCGTTTCT TCGGTACAAT CGCTAAATAT TTGAAATCAG AAGGTTTGCT AGCTGAGACT    420

GGCTACAATC GTTTGATGAT TGAAAAGCCT TTTGGTACAT CATACGCCAC CGCAGAAGAA    480
```

-continued

```
TTGCAAAGTG ATTTGGAAAA TGCATTTGAT GATGACCAAC TGTTCCGTAT TGACCACTAT    540

CTTGGAAAAG AAATGGTACA AAATATTGCA GCATTACGTT TTGGTAACCC AATCTTTGAT    600

GCCGCTTGGA ATAAGGACTA TATCAAAAAC GTACAAGTAA CTTTGGCTGA AGTTCTAGGT    660

GTTGAAGAGC GTGCTGGTTA CTACGATACC ACTGGCGCCC TTTTGGATAT GATTCAAAAC    720

CACACAATGC AAATTGTTGG TTGGTTAGCA ATGGAAAAAC CTGAATCATT CAATGATAAG    780

GATATCCGTG CAGCTAAAAA CGCCGCCTTC AATGCATTAA AGATTTATAA CGAAGAAGAA    840

GTGAATAAGT ACTTCGTTCG TGCACAATAT GGTGCTGGGG ATACAGCTGA TTACAAGCCA    900

TATTTGGAAG AAGCAGATGT CCCTGCTGAC TCAAAGAACA ACACATTCAT TGCTGGGGAA    960

TTGCAGTTCG ATTTGCCACG TTGGGAAGGT GTTCCTTTCT ATGTTCGTTC AGGTAAGCGT   1020

TTGGCTGCCA AGCAAACACG TGTTGATATT GTATTTAAGG CTGGCACATT CAACTTTGGT   1080

TCAGAACAAG AAGCACAAGA ATCAGTACTC TCAATCATCA TTGATCCAAA GGGTGCTATT   1140

GAATTGAAGC TTAACGCTAA GTCAGTTGAA GATGCCTTCA ACACCCGCAC AATCAACTTG   1200

GATTGGGCAG TATCTGATGA AGACAAGAAG AACACACCAG AACCATACGA ACGTATGATT   1260

CACGATACAA TGAATGGTGA CGGATCAAAC TTTGCTGATT GGAACGGTGT ATCAATTGCT   1320

TGGAAGTTTG TTGACGCAAT TACTGCCGTT TACGATGCAG ATAAAGCACC ATTGGAGACA   1380

TATAAGTCAG GTTCAATGGG TCCTGAAGCA TCAGACAAGC TATTAGCTGA AAATGGCGAT   1440

GCTTGGGGAT TTAAAGGA                                                 1458
```

(2) INFORMATION FOR SEQ ID NO:8:

(i) SEQUENCE CHARACTERISTICS:
        (A) LENGTH: 486 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Leuconostoc dextranicum
        (B) STRAIN: ATCC 19255

(xi) SEQUENCE DESCRIPTION: SEQ ID NO:8:

```
Met Val Ser Glu Ile Lys Thr Leu Val Thr Phe Phe Gly Gly Thr Gly
  1               5                  10                  15

Asp Leu Ala Lys Arg Lys Leu Tyr Pro Ser Val Phe Asn Leu Tyr Lys
             20                  25                  30

Lys Gly Tyr Leu Gln Glu His Phe Ala Ile Val Gly Thr Ala Arg Gln
         35                  40                  45

Gln Leu Ser Asp Asp Glu Phe Lys Gln Leu Val Arg Asp Ser Ile Lys
     50                  55                  60

Asp Phe Thr Glu Asp Gln Ala Gln Ala Glu Ala Phe Ile Ala His Ile
 65                  70                  75                  80

Ser Tyr Arg Ala His Asp Val Thr Asp Ala Ala Ser Tyr Gly Ile Leu
                 85                  90                  95

Lys Ser Ala Ile Glu Glu Ala Ala Thr Lys Phe Asp Ile Asp Gly Asn
            100                 105                 110

Arg Ile Phe Tyr Met Ser Val Ala Pro Arg Phe Phe Gly Thr Ile Ala
        115                 120                 125
```

```
Lys Tyr Leu Lys Ser Glu Gly Leu Leu Ala Glu Thr Gly Tyr Asn Arg
    130                 135                 140

Leu Met Ile Glu Lys Pro Phe Gly Thr Ser Tyr Ala Thr Ala Glu Glu
145                 150                 155                 160

Leu Gln Ser Asp Leu Glu Asn Ala Phe Asp Asp Gln Leu Phe Arg
                165                 170                 175

Ile Asp His Tyr Leu Gly Lys Glu Met Val Gln Asn Ile Ala Ala Leu
                180                 185                 190

Arg Phe Gly Asn Pro Ile Phe Asp Ala Ala Trp Asn Lys Asp Tyr Ile
            195                 200                 205

Lys Asn Val Gln Val Thr Leu Ala Glu Val Leu Gly Val Glu Glu Arg
    210                 215                 220

Ala Gly Tyr Tyr Asp Thr Tyr Gly Ala Leu Leu Asp Met Ile Gln Asn
225                 230                 235                 240

His Thr Met Gln Ile Val Gly Trp Leu Ala Met Glu Lys Pro Glu Ser
                245                 250                 255

Phe Asn Asp Lys Asp Ile Arg Ala Ala Lys Asn Ala Ala Phe Asn Ala
                260                 265                 270

Leu Lys Ile Thr Asn Glu Glu Glu Val Asn Lys Tyr Phe Val Arg Ala
    275                 280                 285

Gln Tyr Gly Ala Gly Asp Thr Ala Asp Thr Lys Pro Tyr Leu Glu Glu
    290                 295                 300

Ala Asp Val Pro Ala Asp Ser Lys Asn Asn Thr Phe Ile Ala Gly Glu
305                 310                 315                 320

Leu Gln Phe Asp Leu Pro Arg Trp Glu Gly Val Pro Phe Tyr Val Arg
                325                 330                 335

Ser Gly Lys Arg Leu Ala Ala Lys Gln Thr Arg Val Asp Ile Val Phe
            340                 345                 350

Lys Ala Gly Thr Phe Asn Phe Gly Ser Glu Glu Glu Ala Gln Gln Ser
            355                 360                 365

Val Leu Ser Ile Ile Ile Asp Pro Lys Gly Ala Ile Glu Leu Lys Leu
    370                 375                 380

Asn Ala Lys Ser Val Glu Asp Ala Phe Asn Thr Arg Thr Ile Asn Leu
385                 390                 395                 400

Asp Trp Ala Val Ser Asp Glu Asp Lys Lys Asn Thr Pro Glu Pro Tyr
                405                 410                 415

Glu Arg Met Ile Asn Asp Thr Met Asn Gly Asp Gly Ser Asn Phe Ala
            420                 425                 430

Asp Trp Asn Gly Val Ser Ile Ala Trp Lys Phe Val Asp Ala Ile Thr
        435                 440                 445

Ala Val Tyr Asp Ala Asp Lys Ala Pro Leu Glu Thr Tyr Lys Ser Gly
    450                 455                 460

Ser Met Gly Pro Glu Ala Ser Asp Lys Leu Leu Ala Glu Asn Gly Asp
465                 470                 475                 480

Ala Trp Val Phe Lys Gly
                485
```

(2) INFORMATION FOR SEQ ID NO:9:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Leuconostoc mesenteroides
    (B) STRAIN: ATCC 12291

(xi) SEQUENCE DESCRIPTION: SEQ ID NO:9:

```
AGGTAGTGGT CAATACGGAA TAGTTGGTTA TCATCAAATG CGTTTT           46
```

(2) INFORMATION FOR SEQ ID NO:10:

(i) SEQUENCE CHARACTERISTICS:
        (A) LENGTH: 1458 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:10:

```
GTTTCAGAAA TCAAAACTTT GGTTACATTC TTCGGCGGCA CTGGTGACTT GGCCAAGCGT      60

AAGCTTTACC CATCAGTTTT CAATCTTTAT AAAAAAGGCT ACTTCGAAAA GCATTTTGCC     120

ATTGTTGGAA CGGCCCGTCA AGCCCTCAAT GATGACGAAT TCAAACAATT GGTTCGTGAT     180

TCAATTAAAG ATTTCACTGA CGATCAAGCA CAAGCTGAGG CGTTCACCGA ACATTTCTCA     240

TACCGTGCAC ACGACGTAAC AGATGCTGCT TCATACGCTG TTTTAAAAGA GGCGATTGAA     300

GAAGCTGCCG ACAAATTTGA TATCGATGGC AACCGCATTT TCTATATGTC AGTTGCGCCA     360

CGTTTCTTTG GTACAATTGC CAAATATCTT AAGTCAGAAG GCCTACTAGC TGACACTGGT     420

TACAACCGTT TGATGATTGA AAAGCCTTTC GGTACATCAT ATGACACAGC TGCCGAACTC     480

CAAAATGACT TGGAAAACGC ATTTGATGAT AACCAACTAT TCCGTATTGA CCACTACCTT     540

GGTAAGGAAA TGGTTCAAAA CATTGCTGCC CTTCGCTTTG GTAACCCAAT TTTCGATGCT     600

GCTTGGAACA AGGATTACAT CAAGAACGTT CAAGTAACAT TGTCAGAAGT CTTGGGTGTC     660

GAAGAACGTG CCGGCTACTA TGACACAGCC GGTGCATTGC TCGACATGAT TCAAAACCAC     720

ACCATGCAAA TTGTTGGTTG GTTAGCCATG GAAAAACCAG AATCATTCAC TGACAAAGAC     780

ATTCGTCCGC TAAAAAACGC AGCCTTTAAT GCTTTGAAGA TCTATGATGA AGCAGAAGTT     840

AACAAATACT TGGTTCGTGC ACAATATGGT GCCGGTGATT CAGCTGACTT CAAGCCATAC     900

CTTGAAGAAT TAGACGTACC TGCTGATTCT AAAAACAATA CCTTCATCGC CGGCGAATTG     960

CAATTTGATT TGCCACGTTG GGAGGGTGTC CCATTCTATG TCCGTTCAGG TAAGCGCTTA    1020

GCTGCTAAAC AGACACGGGT TGATATCGTC TTTAAGGCTG GCACGTTTAA CTTTGGTTCA    1080

GAACAAGAAG CACAAGAAGC TGTCTTGTCA ATTATCATTG ATCCAAAGGG TGCTATCGAA    1140

TTGAAGTTGA ACGCTAAGTC AGTTGAAGAT GCTTTCAACA CACGTACAAT TGACTTAGGT    1200

TGGACTGTAT CTGACGAAGA TAAGAAGAAC ACGCCAGAAC CATACGAACG TATGATTCAC    1260

GACATAATGA ATGGTGATGG CTCTAACTTC GCTGACTGGA ATGGCGTTTC AATCGCTTGG    1320

AAGTTCGTTG ATGCTATTTC AGCCGTTTAT ACCGCAGATA AGCACCACT TGAAACTTAC    1380
```

```
AAGTCGGGCT CAATGGGTCC TGAAGCATCC GATAAATTAT TGGCTGCCAA TGGTGATGCT      1440

TGGGTGTTTA AAGGTTAA                                                    1458
```

(2) INFORMATION FOR SEQ ID NO:11:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc citreum
        (B) STRAIN: ATCC 3351

(xi) SEQUENCE DESCRIPTION: SEQ ID NO:11:

```
AGCTTACGCT TTGCTAAATC ACCAGTTCCA CCAAAAAAAG TAACTAATGT TTTGATTTCT      60

GCAAC                                                                  65
```

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:12:

```
TTTTTGGGAT CCATCCATGG TTTCAGAAAT CAAGACGTTA GTAACTTTCT TTGG            54
```

(2) INFORMATION FOR SEQ ID NO:13:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:13:

```
TTTTTTCTAG ATTAAGTTAA CCTTTAAACA CCCAAGCATC ACCATTGGCA GCCAATAATT      60

TATCGGATG                                                              69
```

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:14:

GAACGCCTCA GCTTGTGC                                        18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:15:

GACACAGCCG GTGCATTG                                        18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:16:

GCTAGTAGGC CTTCTGAC                                        18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

-continued (iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:17:

GTGGTGCTTT ATCTGCGG                                                 18

(2) INFORMATION FOR SEQ ID NO:18:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:18:

CGTCAGATAC AGTCCAACC                                                19

(2) INFORMATION FOR SEQ ID NO:19:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:19:

CCGCAGATAA AGCACCAC                                                 18

(2) INFORMATION FOR SEQ ID NO:20:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:20:

```
CACGTTCTTC GACACCCA                                              18
```

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:21:

```
GCGCTTACCT GAACGGAC                                              18
```

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:22:

```
GCACCATATT GTGCACGAAC                                            20
```

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:23:

```
CCTTCATCGC CGGCGAATT                                             19
```

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:24:

CCAAAGGGTG CTATCGAA                                                           18

(2) INFORMATION FOR SEQ ID NO:25:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:25:

GACACAGCTG CCGAACTC                                                           18

(2) INFORMATION FOR SEQ ID NO:26:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:26:

GACGTAACAG ATGCTGCT                                                           18

(2) INFORMATION FOR SEQ ID NO:27:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:27:

GGTGGCACTG GTGACTTG                                                         18

(2) INFORMATION FOR SEQ ID NO:28:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:28:

GAAAACTGAT GGGTAAAGC                                                        19

(2) INFORMATION FOR SEQ ID NO:29:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:29:

TCAGTTGCGC CACGTTTC                                                         18

(2) INFORMATION FOR SEQ ID NO:30:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:30:

CGCAGCCTTT AATGCTTTG                                                        19

(2) INFORMATION FOR SEQ ID NO:31:

(i) SEQUENCE CHARACTERISTICS:
         (A) LENGTH: 18 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:31:

GCTGACTGGA ATGGCGTT                                                    18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:32:

ACGCCAGAAC CATACGAA                                                    18

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:33:

CTTAGCTGCT CGTCAGACAC G                                                21

(2) INFORMATION FOR SEQ ID NO:34:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO

```
    (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:34:

GGTTGATATC GTCTTTAAGG CTGGTACCTT TAACTTTG                              38

(2) INFORMATION FOR SEQ ID NO:35:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:35:

GTCCCATTCT ACGTACGTTC AGGTCGTCGC TTAGCTG                               37

(2) INFORMATION FOR SEQ ID NO:36:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:36:

GAAGTTAACC GTTACTTTGT TAGAGCTCAA TATGGTG                               37

(2) INFORMATION FOR SEQ ID NO:37:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:37:

AAGCACCACT CGAGACTTAC CGTTCGGGCT CAA                                   33

(2) INFORMATION FOR SEQ ID NO:38:
```

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:38:

GCATCCGATC GTTTATTGGC TG                                                    22

(2) INFORMATION FOR SEQ ID NO:39:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:39:

GTTCGAGAAA TCCGTACACT AGTTACTTT                                             29

(2) INFORMATION FOR SEQ ID NO:40:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:40:

CGTTTATACT GCAGATCGTG CACCACTTG                                             29

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:41:

CTACGTGGGT TGCGAAATGG TTC                                          23

(2) INFORMATION FOR SEQ ID NO:42:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: NCIMB 3351

(xi) SEQUENCE DESCRIPTION: SEQ ID NO:42:

GATCATTACC TGGGTTGCGA AATGGTCC                                     28

(2) INFORMATION FOR SEQ ID NO:43:

(i) SEQUENCE CHARACTERISTICS:
            (A) LENGTH: 55 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:43:

CTATTCCGTA TTGACCACTA CTGTGGTAAG GAAATGGTTC AAAACATTGC TGCCC        55

(2) INFORMATION FOR SEQ ID NO:44:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: NCIMB 3351

(xi) SEQUENCE DESCRIPTION: SEQ ID NO:44:

CTTGCTATGG AACGTCCAGA TTCA                                         24

(2) INFORMATION FOR SEQ ID NO:45:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:45:

CTTGCTATGG AATGCCCAGA TTCA                                              24

(2) INFORMATION FOR SEQ ID NO:46:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:46:

ATTTGACTGA TAAGGAATTC AAGCA                                             25

(2) INFORMATION FOR SEQ ID NO:47:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:47:

CTGTGGCACC GCGGTTCTTT GGGACAATTG CACGTTATCT CAAG                         44

(2) INFORMATION FOR SEQ ID NO:48:

(i) SEQUENCE CHARACTERISTICS:
        (A) LENGTH: 31 base pairs
        (B) TYPE: nucleic acid
        (C) STRANDEDNESS: single
        (D) TOPOLOGY: linear

```
    (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:48:

GACAATTGCA CGTTATCTCC GTTCAGAGGG T                                31

(2) INFORMATION FOR SEQ ID NO:49:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:49:

TGAAAAGTGT TCGATGAATG CCTCGGC                                    27

(2) INFORMATION FOR SEQ ID NO:50:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:50:

TATAAAAAAG GATATCTGCA ATGCCATTTT GCCATT                          36

(2) INFORMATION FOR SEQ ID NO:51:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351
```

(xi) SEQUENCE DESCRIPTION: SEQ ID NO:51:

GACCATGGTT TGCGAAATCA AAACATTAG                                29

(2) INFORMATION FOR SEQ ID NO:52:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:52:

AGCTAGTAGG CCTTCTGACT TAAGATAACG GCAATTGTA CC                  42

(2) INFORMATION FOR SEQ ID NO:53:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:53:

AGCTAGTAGG CCTTCTGAAC GAAGATATTT GGC                           33

(2) INFORMATION FOR SEQ ID NO:54:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:54:

GAATGATTCT GGACGTTCCA TCGCTAA                                  27

(2) INFORMATION FOR SEQ ID NO:55:

(i) SEQUENCE CHARACTERISTICS:
        (A) LENGTH: 27 base pairs
        (B) TYPE: nucleic acid

```
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:55:

TTAGCGATGG AACGTCCAGA ATCATTC                                            27

(2) INFORMATION FOR SEQ ID NO:56:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:56:

GAGGTACCGA AAGGACGTTC AATC                                               24

(2) INFORMATION FOR SEQ ID NO:57:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:57:

GATTGAACGT CCTTTCGGTA CCTC                                               24

(2) INFORMATION FOR SEQ ID NO:58:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
```

```
        (A) ORGANISM: Leuconostoc mesenteroides
        (B) STRAIN: ATCC 12291

(xi) SEQUENCE DESCRIPTION: SEQ ID NO:58:

TCATTCACTG ACCGTGATAT CCGTGCC                                          27

(2) INFORMATION FOR SEQ ID NO:59:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:59:

GGCACGGATA TCACGGTCAG TGAATGA                                          27

(2) INFORMATION FOR SEQ ID NO:60:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:60:

ATTCGTGCCG CGCGCAACGC AGCCTTT                                          27

(2) INFORMATION FOR SEQ ID NO:61:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:61:

AAAGGCTGCG TTGCGCGCGG CACGAAT                                          27

(2) INFORMATION FOR SEQ ID NO:62:
```

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Leuconostoc mesenteroides
    (B) STRAIN: NCIMB 3351

(xi) SEQUENCE DESCRIPTION: SEQ ID NO:62:

ACTATCAGCT AGCAAACCCT CTGACTTGAG ATAACGTGCA ATTGT                45

(2) INFORMATION FOR SEQ ID NO:63:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:63:

ACTATCAGCT AGCAAACCCT CTGAACTGAG ATATTT                          36

(2) INFORMATION FOR SEQ ID NO:64:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:64:

GCCGAAGTCA ACCGTTATTT CCTCCGT                                    27

(2) INFORMATION FOR SEQ ID NO:65:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: NCIMB 3351

(xi) SEQUENCE DESCRIPTION: SEQ ID NO:65:

GATATCGACA CGTGTTTGTT TAGCAGCTAA ACGACGGCCT GAACG                45

(2) INFORMATION FOR SEQ ID NO:66:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: NCIMB 3351

(xi) SEQUENCE DESCRIPTION: SEQ ID NO:66:

GATATCGACA CGTGTTTGAC GAGCAGCTAA ACG                             33

(2) INFORMATION FOR SEQ ID NO:67:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: NCIMB 3351

(xi) SEQUENCE DESCRIPTION: SEQ ID NO:67:

AAACAAACAC GTGTCGATAT CGTCTTCCGT GCTGGTACC                       39

(2) INFORMATION FOR SEQ ID NO:68:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: NCIMB 3351

(xi) SEQUENCE DESCRIPTION: SEQ ID NO:68:

ATTTCAGCTG TCTACACTGC TGATCGTGCA CCACTT                          36

(2) INFORMATION FOR SEQ ID NO:69:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:69:

TGCTTCAGGT CCCATGGAAC CTGAACGGTA TGTTTC                                    36

(2) INFORMATION FOR SEQ ID NO:70:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:70:

ACTAACTAAT GTACGGATAT CTGCAAC                                              27

(2) INFORMATION FOR SEQ ID NO:71:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:71:

GTTGCAGATA TCCGTACATT AGTTACT                                              27

(2) INFORMATION FOR SEQ ID NO:72:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

```
    (iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:72:

CCGAAGAGCT CCAACGTGAC TTAGAA                                              26

(2) INFORMATION FOR SEQ ID NO:73:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:73:

TTCTAACTCA CGTTGGAGCT CTTCGG                                              26

(2) INFORMATION FOR SEQ ID NO:74:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:74:

TGAAAAGTGT TCGATGAATG CCTCGGC                                             27

(2) INFORMATION FOR SEQ ID NO:75:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:75:
```

```
GCCGAGGCAT TCATCGAACA CTTTTCA                                          27
```

(2) INFORMATION FOR SEQ ID NO:76:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:76:

```
GATTTGACTG ATGATGAGTT CAAGCAA                                          27
```

(2) INFORMATION FOR SEQ ID NO:77:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:77:

```
TTGCTTGAAC TCATCATCAG TCAAATC                                          27
```

(2) INFORMATION FOR SEQ ID NO:78:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:78:

```
TAACTCGTTT TGGAGCTCTT CGGCAGTGTC GTATGA                                36
```

(2) INFORMATION FOR SEQ ID NO:79:

(i) SEQUENCE CHARACTERISTICS:
        (A) LENGTH: 36 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:79:

TCATACGACA CTGCCGAAGA GCTCCAAAAC GACTTA                              36

(2) INFORMATION FOR SEQ ID NO:80:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:80:

GTTCGTGAAT CAATCAAGGA CTTTACTGAA G                                   31

(2) INFORMATION FOR SEQ ID NO:81:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: NCIMB 3351

(xi) SEQUENCE DESCRIPTION: SEQ ID NO:81:

CTTCAGTAAA GTCCTTAATT AATTCACGAA C                                   31

(2) INFORMATION FOR SEQ ID NO:82:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides (B) STRAIN: NCIMB 3351

(xi) SEQUENCE DESCRIPTION: SEQ ID NO:82:

CAGCGTTTGA CTGATTGTGA GTTCAAGCAA                                    30

(2) INFORMATION FOR SEQ ID NO:83:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:83:

TGCTTGAACT CACAATCAGT CAAATC                                        26

(2) INFORMATION FOR SEQ ID NO:84:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:84:

ACAGCACGTC AGGCTTTGAC TGATTGTGAC TTCAAGCAA                           39

(2) INFORMATION FOR SEQ ID NO:85:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:85:

TGCTTGAACT CACAATCAGT CAAAGCCTGA CGTGC                               35

(2) INFORMATION FOR SEQ ID NO:86:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:86:

GGAACGGCCC GTGCATGCCT CAATCA                                              26

(2) INFORMATION FOR SEQ ID NO:87:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:87:

TCATTGAGGC ATGCACGGGC CGTTCC                                              26

(2) INFORMATION FOR SEQ ID NO:88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:88:

CAATGATTGC AGGTTCAAAC AA                                                  22

(2) INFORMATION FOR SEQ ID NO:89:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:89:

TTGTTTGAAC TCGCAATCAT TG                                              22

(2) INFORMATION FOR SEQ ID NO:90:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:90:

GATGACGAGT TCTGCCAATT GGTTCG                                          26

(2) INFORMATION FOR SEQ ID NO:91:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:91:

CGAACCAATT GGCAGAACTC GTCATC                                          26

(2) INFORMATION FOR SEQ ID NO:92:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: ATCC 12291

(xi) SEQUENCE DESCRIPTION: SEQ ID NO:92:

GATGACGAGT TCAAATGCTT GGTTCATG                                        28

(2) INFORMATION FOR SEQ ID NO:93:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:93:

CACGAACCAA GCATTTGAAC TCGTCATC                                           28

(2) INFORMATION FOR SEQ ID NO:94:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:94:

CAATGATGAC TGCTTCAAAC A                                                  21

(2) INFORMATION FOR SEQ ID NO:95:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:95:

TGTTTGAAGC AGTCATCATT G                                                  21

(2) INFORMATION FOR SEQ ID NO:96:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:96:

GGAACGGCCC GTTGCGCCCT CAATGATGAC GAGTTC                                      36

(2) INFORMATION FOR SEQ ID NO:97:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:97:

GAACTCGTCA TCATTGAGGG CGCAACGGGC CGTTCC                                      36

(2) INFORMATION FOR SEQ ID NO:98:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:98:

GGAACGGCCC GTCAAGCCTG CAATGATGAC GAGTTC                                      36

(2) INFORMATION FOR SEQ ID NO:99:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:99:

```
GAACTCGTCA TCATTGGAGG CTTGACGGGC CGTTCC                                         36
```

(2) INFORMATION FOR SEQ ID NO:100:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:100:

```
GGAACGGCCT GCCAAGCCCT CAATGATGAC GAGTTC                                         36
```

(2) INFORMATION FOR SEQ ID NO:101:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:101:

```
GAACTCGTCA TCATTGAGGG CTTGGCAGGC CGTTCC                                         36
```

(2) INFORMATION FOR SEQ ID NO:102:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:102:

```
CAAGCCCTCT GCGATGACGA GTTCAAACA                                                 29
```

(2) INFORMATION FOR SEQ ID NO:103:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:103:

TGTTTGAACT CGTCATCGCA GAGGGCTTG                                              29

(2) INFORMATION FOR SEQ ID NO:104:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:104:

CAAGCCCTCA ATTGCGACGA GTTCAAACA                                              29

(2) INFORMATION FOR SEQ ID NO:105:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:105:

TGTTTGAACT CGTCGCAATT GAGGGCTTG                                              29

(2) INFORMATION FOR SEQ ID NO:106:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Leuconostoc mesenteroides
             (B) STRAIN: ATCC 12291

(xi) SEQUENCE DESCRIPTION: SEQ ID NO:106:

GATGACGAAT GCAAACAATT GGTTCGTG                                                28

(2) INFORMATION FOR SEQ ID NO:107:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:107:

CACGAACCAA TTGTTTGCAT TCGTCATC                                                28

(2) INFORMATION FOR SEQ ID NO:108:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:108:

ACAATTGCCT GCTATCTTAA GTCAGAAGGT CTACT                                        35

(2) INFORMATION FOR SEQ ID NO:109:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:109:

AGTAGACCTT CTGACTTAAG ATAGCAGGCA ATTGT                                        35

(2) INFORMATION FOR SEQ ID NO:110:

(i) SEQUENCE CHARACTERISTICS:
        (A) LENGTH: 34 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:110:

GCCAAATATC TTTGCTCAGA AGGTCTACTA GCTG                                      34

(2) INFORMATION FOR SEQ ID NO:111:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:111:

CAGCTAGTAG ACCTTCTGAG CAAAGATAAT TGGC                                      34

(2) INFORMATION FOR SEQ ID NO:112:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:112:

GATGACGAGT TCAAACAATG CGTTCGTG                                             28

(2) INFORMATION FOR SEQ ID NO:113:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO

```
    (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:113:

CACGAACGCA TTGTTTGAAC TCGTCATC                                              28

(2) INFORMATION FOR SEQ ID NO:114:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:114:

GATGACGAGT TCAAACAATT GTGCCGTG                                              28

(2) INFORMATION FOR SEQ ID NO:115:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:115:

CACGGCACAA TTGTTTGAAC TCGTCATC                                              28

(2) INFORMATION FOR SEQ ID NO:116:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Leuconostoc mesenteroides
         (B) STRAIN: ATCC 12291

(xi) SEQUENCE DESCRIPTION: SEQ ID NO:116:

GACGAGTTCA AACAATTGGT TTGCGATTCA                                            30

(2) INFORMATION FOR SEQ ID NO:117:
```

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:117:

TGAATCGACA ACCAATTGTT TGAACTCGTC                                              30

(2) INFORMATION FOR SEQ ID NO:118:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:118:

GACGAGTTCA AACAATTGGT TCGTTGCTCA ATT                                          33

(2) INFORMATION FOR SEQ ID NO:119:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: ATCC 12291

(xi) SEQUENCE DESCRIPTION: SEQ ID NO:119:

AATTGAGCAA CGAACCAATT GTTTGAACTC GTC                                          33

(2) INFORMATION FOR SEQ ID NO:120:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: NCIMB 3351

(xi) SEQUENCE DESCRIPTION: SEQ ID NO:120:

TGAAGGATAA AGTCGACGCT TTGCT                                              25

(2) INFORMATION FOR SEQ ID NO:121:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: NCIMB 3351

(xi) SEQUENCE DESCRIPTION: SEQ ID NO:121:

TGAAGGATAA AGCTTACGAC GTGCTAAATC A                                       31

(2) INFORMATION FOR SEQ ID NO:122:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: NCIMB 3351

(xi) SEQUENCE DESCRIPTION: SEQ ID NO:122:

GGCACCATAC TGAGCTCTGA CGAAATAACG GTTGACTTCG                               40

(2) INFORMATION FOR SEQ ID NO:123:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Leuconostoc mesenteroides
            (B) STRAIN: NCIMB 3351

(xi) SEQUENCE DESCRIPTION: SEQ ID NO:123:

CTTGTATGTT TCTAGAGGTG CACGATCTGC AGTGTAGA                                 38

```
(2) INFORMATION FOR SEQ ID NO:124:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Leuconostoc mesenteroides
        (B) STRAIN: NCIMB 3351

(xi) SEQUENCE DESCRIPTION: SEQ ID NO:124:

TTCGGCTAAC AGACGGTCAG ATGCTTCAGG GCCCATGGAA C                              41
```

HOMOGENEOUS IMMUNOASSAYS USING MUTANT GLUCOSE-6-PHOSPHATE DEHYDROGENASES

BACKGROUND OF THE INVENTION

1. Field of the Invention

The present invention relates to homogeneous immunoassays for analytes and compositions of matter that are useful in conducting such immunoassays. Homogeneous immunoassays have the advantage of not requiring separation steps. Such assays, however, are limited by the difficulty of selecting antibodies which will modulate the activity of a label that is normally bound to the antibodies or an analog of the analyte.

The present invention relates to methods for immunoassay of analytes employing mutant glucose-6-phosphate dehydrogenase (G6PDH) enzymes as labels. In particular, the invention relates to the use of conjugates of an analyte and a mutant $NAD^+$ dependent G6PDH of bacterial origin differing from any precursor G6PDH by the deletion, substitution, or insertion, or any combination thereof of at least one amino acid per subunit. The invention also involves the construction of several mutations in a precursor glucose-6-phosphate dehydrogenase (G6PDH) enzymes. Typically, the mutations involve deletion or substitution of one or more lysine residues, or introduction of one or more cysteine residues by insertion of cysteine to a precursor G6PDH or substitution of precursor G6PDH amino acid residues with cysteine. The present invention also relates to conjugates of the subject enzymes and specific binding pair members, cell lines producing the subject enzymes, DNA sequences encoding the subject enzymes, and plasmids containing DNA encoding the subject enzymes and designed to allow a host cell to produce the subject enzymes.

2. Brief Description of the Related Art

Adams, M. J., H. R. Levy, and K. Moffat; 1983; Crystallization and preliminary X-ray data for glucose-6-phosphate dehydrogenase from *Leuconostoc mesenteroides*; J. Bio. Chem. 258:5867–5868; discloses the crystallization and preliminary X-ray data for glucose-6-phosphate dehydrogenase from *Leuconostoc mesenteroides*.

Barnell, W. O., K. C. Yi, and T. Conway; 1990; Sequence and genetic organization of a *Zymomonas mobilis* gene cluster that encodes several enzymes of glucose metabolism; J. Bacteriology 172:7227–7240; discloses cloning, sequence and organization of Zymomonas mobilis genes encoding glycolytic pathway enzymes, including glucose-6-phosphate dehydrogenase. The information is said to be useful as a tool for studying the contribution of gene expression to flux control at each step of the pathway.

Bhadbhade, M. M., M. J. Adams, T. G. Flynn, and H. R. Levy; 1987; Sequence identity between a lysine-containing peptide from *Leuconostoc mesenteroides* glucose-6-phosphate dehydrogenase and an active site peptide from human erythrocyte glucose-6-phosphate dehydrogenase; FEBS Lett. 211:243–246; discloses the sequence identity between a lysine-containing peptide from *Leuconostoc mesenteroides* glucose-6-phosphate dehydrogenase and an active site peptide from human erythrocyte glucose-6-phosphate dehydrogenase.

Gasser, F., and M. Hontebeyrie; 1977; Immunological relationships of glucose-6-phosphate dehydrogenase of *Leuconostoc mesenteroides* NCDO 768 (=ATCC 12291); Int. J. Systematic Bact. 27:6–8; discloses the immunological cross-reactivity patterns of antibodies capable of recognizing *Leuconostoc mesenteroides* with various Leuconostoc strains Haghighi, B., T. G. Flynn, and H. R. Levy; 1982; Glucose-6-phosphate dehydrogenase from *Leuconostoc mesenteroides*; Isolation and sequence of a peptide containing an essential lysine; Biochemistry 21:6415–6420; discloses the interaction of glucose-6-phosphate dehydrogenase from *Leuconostoc mesenteroides* with pyridoxal 5'-phosphate and sodium borohydride.

Heilmann, H. J., H. J. Migert, and H. G. Gassen; 1988; Identification and isolation of glucose-6-phosphate dehydrogenase genes of *Bacillus megaterium* M1286 and their expression in *Escherichia coli*; Eur. J. Biochem. 174:485–490; discloses the identification and isolation of glucose dehydrogenase genes of *Bacillus megaterium*M1286 and their expression in *Escherichia coli*.

Hey, Y., and P. D. G. Dean; 1983; Tandem dye-ligand chromatography and biospecific elution applied to the purification of glucose-6-phosphate dehydrogenase from *Leuconostoc mesenteroides*; Biochem. J. 209:363–371; discloses the purification of glucose-6-phosphate dehydrogenase from *Leuconostoc mesenteroides*.

Hontebeyrie, M.; and F. Gasser; 1975; Comparative immunological relationships of two distinct sets of isofunctional dehydrogenases in the genus Leuconostoc; Int. J. Systematic Bact. 25:1–6; discloses the immunological cross-reactivity patterns of antibodies capable of recognizing *Leuconostoc lactis* with various Leuconostoc strains and heterofermentative lactobacilli.

Ishaque, A., M. Milhausen, and H. R. Levy; 1974; On the absence of cysteine in glucose-6-phosphate dehydrogenase from *Leuconostoc mesenteroides*; Biochem. Biophys. Res. Commn. 59:894–901; discloses the complete lack of cysteine in *Leuconostoc mesenteroides*.

Jarsch, M., and G. Lang; Cloning and overexpression of glucose-6-phosphate dehydrogenase from *Leuconostoc dextranicus*; Canadian Patent Application Number 2,045,838 A1 (published Jan. 31, 1992); discloses recombinant glucose-6-phosphate dehydrogenase enzymes derived from *Leuconostoc dextranicus* having improved temperature stability.

Jeffery, J., L. Hobbs, and H. Jörnvall; 1985; Glucose-6-phosphate dehydrogenase from *Saccharomyces cerevisiae*: characterization of a reactive lysine residue labeled with acetylsalicylic acid; Biochem. 24:666–671: discloses the characterization of a reactive lysine residue that reacts with acetylsalicylic acid.

Jeffery, J., I. Wood, A. Macleod, R. Jeffery, and H. Jörnvall; 1989; Glucose-6-phosphate dehydrogenase; Biochem. Biophys. Res. Commn. 160:1290–1295; discloses the characterization of a reactive lysine residue in the *Pichia jadirnii* glucose-6-phosphate dehydrogenase enzyme. The information is said to reveal a limited structural variation in a functionally significant segment of the enzyme.

Lee, W. T., T. G. Flynn, C. Lyons, and H. R. Levy; 1991; Cloning of the gene and amino acid sequence for glucose-6-phosphate dehydrogenase from *Leuconostoc mesenteroides*; J. Bio. Chem. 266:13028–13034; discloses the cloning of the *Leuconostoc mesenteroides* glucose-6-phosphate dehydrogenase gene and the amino acid sequence of the enzyme, derived from partial sequencing of the DNA. The information is said to be useful for site-directed mutagenesis studies of those structural features of *Leuconostoc mesenteroides* glucose-6-phosphate dehydrogenase that allow for $NAD^+$ binding and utilization.

Lee, W. T., and H. R. Levy; 1992; Lysine-21 of *Leuconostoc mesenteroides* glucose 6-phosphate dehydrogenase participates in substrate binding through charge-charge interaction; Protein Science 1:329–353; discloses the purification and kinetic characterization of Lys-21-Arg and Lys-21-Gln mutants of glucose-6-phosphate dehydrogenase in order to determine the function of Lys-21.

Levy, H. R.; 1979; glucose-6-phosphate dehydrogenases; Advances in Enzymology 48:97–192; discloses the isolation, structure, and catalytic activity of glucose-6-phosphate dehydrogenases.

Levy, H. R., and W. T. Lee; Cloned *Leuconostoc mesenteroides* glucose-6-phosphate dehydrogenase genes and methods of making same; International Patent Application Number PCT/US91/07715 (International publication WO 92/07078, Apr. 30, 1992) discloses the isolation, PCR amplification and cloning of a gene for glucose-6-phosphate dehydrogenase from *Leuconostoc mesenteroides* into plasmid pUC19 for expression in *E. coli*.

Murphy, N. B., D. J. McConnell, and T. F. R. Schwarz; 1987; Expression of the gene for NAD$^+$-dependent glucose-6-phosphate dehydrogenase from *Leuconostoc mesenteroides* cloned in *Escherichia coli* K-12; J. Bacteriology 169:334–339; discloses the expression of the gene for NAD$^+$-dependent glucose-6-phosphate dehydrogenase from *Leuconostoc mesenteroides* cloned in *Escherichia coli* K-12.

Olive, C., and H. R. Levy; 1967; The preparation and some properties of crystalline glucose 6-phosphate dehydrogenase from *Leuconostoc mesenteroides*; Biochemistry 6:730–736; discloses the purification of glucose-6-phosphate dehydrogenase from extracts of *Leuconostoc mesenteroides*.

Rowley, D. L., and R. E. Wolf; 1991; Molecular characterization of the *Escherichia coli* K-12 zwf gene encoding glucose-6-phosphate dehydrogenase; J. Bacteriology 173:968–977; discloses cloning and sequencing of *Escherichia coli* K-12 glucose-6-phosphate dehydrogenase. The information is said to be useful in the search for an internal complementary sequence that functions as a cis-acting antisense RNA by forming a long-range secondary structure that sequesters the ribosome binding site.

Rubenstein, K. E., and R. K. Leute; Antibody Steric Hindrance Immunoassay with Two Antibodies; U.S. Pat. No. 3,935,074, Jan. 27, 1976 (filed Dec. 17, 1973); discloses an antibody steric hindrance immunoassay using two antibodies.

Rubenstein, K. E., and E. F. Ullman; Enzyme amplification Assay; U.S. Pat. No. 3,817,837, Jun. 18, 1974 (filed Nov. 6, 1972); discloses homogeneous immunoassays.

Skold, C., I. Gibbons, D. Gould, and E. F. Ullman; 1987; Monoclonal antibodies to glucose-6-phosphate dehydrogenase (G6PDH) form cyclic 1:1 complexes with G6PDH and act as regulatory subunits; J. Immunology 138:3408–3414; and Skold, C., D. R. Gould, and E. F. Ullman; Methods for modulating ligand-receptor interactions and their application; U.S. Pat. No. 4,727,022, Feb. 23, 1988 (filed Mar. 14, 1984); discloses the preparation of inhibitory antibodies to G6PDH from *L. mesenteroides*.

Yoshida, R. A., and E. T. Maggio; Antienzyme Homogeneous Competitive Binding Assay; U.S. Pat. No. 4,233,401, Nov. 11, 1980 (filed Jul. 14, 1977); discloses a protein binding assay for a member of an immunological pair whereby an enzyme-ligand conjugate is employed in combination with an enzyme inhibitor that can be an antibody.

SUMMARY OF THE INVENTION

One aspect of the present invention relates to methods for homogeneous immunoassay of an analyte in a sample suspected of containing the analyte. The methods comprise the steps of: (1) combining in a liquid medium: (a) the sample to be assayed, (b) a conjugate of (i) an analyte analog and (ii) a mutant NAD$^+$ dependent G6PDH differing from any precursor G6PDH by the deletion, substitution, or insertion or any combination thereof of at least one amino acid per subunit, (c) a receptor for the analyte, and (d) substrates for the G6PDH; (2) determining the enzymatic activity of the G6PDH in the medium; and (3) comparing the enzymatic activity to the enzymatic activity observed with a sample containing the analyte.

Another aspect of the present invention relates to methods for determining the amount of a specific binding pair (sbp) member in a sample suspected of containing the sbp member. The methods comprise the steps of: (a) combining in an assay medium: (1) the sample, (2) a conjugate of an enzyme and an analog of the sbp member, wherein the enzyme is a mutant bacterial glucose-6-phosphate dehydrogenase (G6PDH) having at least two amino acid mutations per subunit as compared to precursor G6PDH, and (3) an sbp partner of the sbp member capable of binding the conjugate, and (b) determining the activity of the enzyme.

Another aspect of the present invention relates to methods for determining the presence or amount of an analyte in a sample suspected of containing the analyte. The methods comprise the steps of: a) combining in an assay medium: 1) the sample, 2) a conjugate of an analyte analog and an enzyme, wherein the enzyme is a mutant glucose-6-phosphate dehydrogenase (G6PDH) derived from an organism selected from the group consisting of *Leuconostoc mesenteroides, Leuconostoc citreum, Leuconostoc lactis*, and *Leuconostoc dextranicus* wherein the G6PDH has at least one amino acid mutation per subunit as compared to precursor G6PDH wherein at least one of the mutations comprises the introduction of a cysteine residue proximate to an epitope recognized by an inhibitory anti-G6PDH antibody capable of simultaneously binding to two of the subunits within the same G6PDH molecule, 3) an antibody capable of binding the analyte and the analyte analog conjugate, and 4) substrates for the enzyme; and b) measuring the activity of the enzyme.

Another aspect of the present invention relates to improved methods for determining the presence of a ligand in a sample suspected of containing the ligand. The assay to be improved includes the steps of: a) bringing together in an aqueous medium: 1) the sample, 2) enzyme-bound-ligand, and 3) receptor capable of binding to the ligand and the enzyme-bound-ligand, wherein the receptor is at a concentration sufficient to substantially change the enzymatic activity of the enzyme-bound-ligand in the absence of the ligand; b) determining the enzymatic activity of the enzyme-bound-ligand in the medium; and the improvement comprises employing as the enzyme a mutant glucose-6-phosphate dehydrogenase (G6PDH) having at least two amino acid mutations as compared to a precursor G6PDH.

Another aspect of the present invention relates to compositions comprising a specific binding pair member conjugated to a mutant NAD$^+$ dependent bacterial glucose-6-phosphate dehydrogenase (G6PDH) having at least one amino acid mutation per subunit as compared to precursor G6PDH.

Another aspect of the present invention relates to a mutant glucose-6-phosphate dehydrogenase (G6PDH) enzyme that is the expression product of a mutated DNA sequence encoding a glucose-6-phosphate dehydrogenase, the mutant DNA sequence being derived from a precursor glucose-6- phosphate dehydrogenase by the deletion, insertion or substitution of one or more amino acids in the precursor glucose-6-phosphate dehydrogenase. Preferably, the G6PDH is an NAD$^+$ dependent bacterial G6PDH, more preferably the mutant DNA sequence is derived from a precursor glucose-6-phosphate dehydrogenase by the deletion, insertion or substitution of two or more amino acids in the precursor glucose-6-phosphate dehydrogenase.

Another aspect of the present invention relates to mutant glucose-6-phosphate dehydrogenase (G6PDH) enzymes having at least one mutation per subunit as compared to precursor G6PDH wherein the mutation is proximate to an epitopic site recognized by an anti-G6PDH antibody capable of inhibiting the activity of the precursor G6PDH.

Another aspect of the present invention relates to mutant DNA sequences encoding such glucose-6-phosphate dehydrogenase (G6PDH) enzymes. These mutant DNA sequences are derived from a precursor DNA sequence which encodes a naturally-occurring or recombinant precursor enzyme. The mutant DNA sequences are derived by modifying the precursor DNA sequence to encode the substitution, deletion or insertion of at least one amino acid residue encoded by the precursor DNA sequence. These recombinant DNA sequences encode glucose-6-phosphate dehydrogenase mutant enzymes having a novel amino acid sequence.

Further the invention relates to expression vectors containing such mutant glucose-6-phosphate dehydrogenase DNA sequences as well as host cells transformed with such vectors which are capable or producing such mutant enzymes.

Another aspect of the present invention relates to improved assay reagents for use in the determination of an analyte in a sample suspected of containing the analyte. The assay reagents include an analyte-label conjugate. The improvement comprises employing as the label mutant NAD$^+$ dependent glucose-6-phosphate dehydrogenase (G6PDH) enzymes having at least one mutation per subunit as compared to precursor G6PDH wherein the mutations are proximate to an epitopic site recognized by an anti-G6PDH antibody capable of inhibiting the activity of the precursor G6PDH.

Another aspect of the present invention relates to kits for conducting an assay for the determination of a specific binding pair (sbp) member. The kits comprise in packaged combination an sbp partner of the sbp member and a composition which comprises the sbp member or an analog of the sbp member conjugated to a mutant NAD$^+$ dependent bacterial glucose-6-phosphate dehydrogenase (G6PDH) having at least one amino acid mutation per subunit as compared to precursor G6PDH.

BRIEF DESCRIPTION OF THE DRAWINGS

FIG. 1 is the DNA sequence of the gene encoding G6PDH from L. mesenteroides strain ATCC 12291 (SEQ ID NO:1).

FIG. 2 is the amino acid sequence of the G6PDH from L. mesenteroides strain ATCC 12291 (SEQ ID NO:2).

FIG. 3 is the DNA sequence of the gene encoding G6PDH from L. citreum strain NCIMB 3351 (SEQ ID NO:3).

FIG. 4 is the amino acid sequence of the G6PDH from L. citreum strain NCIMB 3351 (SEQ ID NO:4).

FIG. 5 is the DNA sequence of the gene encoding G6PDH from L. lactis strain NCDO 546 (SEQ ID NO:5).

FIG. 6 is the amino acid sequence of the G6PDH from L. lactis strain NCDO 546 (SEQ ID NO:6).

FIG. 7 is the DNA sequence of the gene encoding G6PDH from L. dextranicus strain ATCC 19255 (SEQ ID NO:7).

FIG. 8 is the amino acid sequence of the G6PDH from L. dextranicus strain ATCC 19255 (SEQ ID NO:8).

FIG. 9 is plasmid pJS12.

FIG. 10 is vector pDR540.

FIG. 12 is plasmid pKK233-2

DESCRIPTION OF THE SPECIFIC EMBODIMENTS

Figure 11:
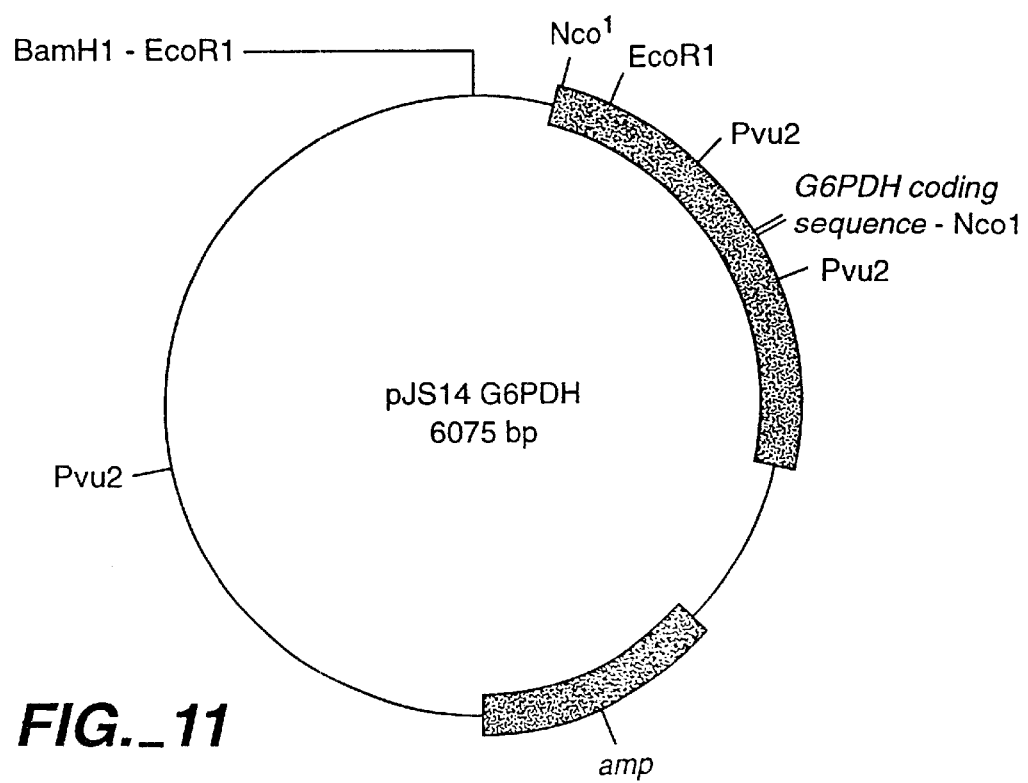
FIG. 11 is plasmid pJS14.

The present invention relates to methods for immunoassay of analytes employing mutant glucose-6-phosphate dehydrogenase (G6PDH) enzymes as labels. In particular, the invention relates to the use of conjugates of an analog of an analyte to be determined and a mutant NAD$^+$ dependent G6PDH differing from any precursor G6PDH by the deletion, substitution, or insertion, or any combination thereof of at least one amino acid per subunit. The invention also involves the construction of multiple mutations in precursor glucose-6-phosphate dehydrogenase (G6PDH) genes. Typically, the mutations involve deletion or substitution of one or more lysine residues, or introduction of one or more cysteine residues by insertion of cysteine to precursor G6PDH or substitution of precursor G6PDH amino acid residues with cysteine. The present invention also relates to conjugates of the subject enzymes and specific binding pair members, cell lines producing the subject enzymes, DNA and amino acid sequences encoding the subject enzymes, and plasmids (vectors) containing DNA encoding the subject enzymes and designed to allow a host cell to produce the subject enzymes.

Before proceeding further with the description of the specific embodiments of the invention, a number of terms will be defined.

DEFINITIONS

Analyte * * * The compound or composition to be measured, the material of interest. The analyte is a member of a specific binding pair (sbp) and may be a ligand, which is mono- or polyvalent, usually antigenic or haptenic, and is a single compound or plurality of compounds which share at least one common epitopic or determinant site.

The polyvalent ligand analytes will normally be poly (amino acids), i.e., polypeptides and proteins, polysaccharides, nucleic acids, and combinations thereof.

The precise nature of some of the analytes together with numerous examples thereof are disclosed in U.S. Pat. No. 4,299,916 to Litman, et al., particularly at columns 16 to 23, the disclosure of which is incorporated herein by reference.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 5,000 molecular weight, more usually from 125 to 2,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextroamphetamine, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantoin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, cotinine, lidocaine, procainamide, n-acetylprocainamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamycin, tobramycin, and amikacin.

Among pesticides of interest are polyhalogenated biphenyls, phosphate esters, thiophosphates, carbamates, polyhalogenated sulfenamides, their metabolites and derivatives.

Also included are hormones such as progesterone, testosterone, thyroid hormones, and so forth.

For receptor analytes, the molecular weights will generally range from 10,000 to $2\times10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

A particularly preferred group of analytes are drugs including, by way of example and not limitation, drugs selected from the group consisting of digoxin, vancomycin, thyroxine, cyclosporin, folate, rapamycin, vitamin B12, mycophenolate, FK506 and tetrahydrocannabinol.

Sample Suspected of Containing Analyte * * * Any sample which is reasonably suspected of containing analyte can be analyzed by the method of the present invention. Such samples can include human, animal or man-made samples. The sample can be prepared in any convenient medium which does not interfere with the assay. Typically, the sample is an aqueous solution or a natural fluid, preferably, urine, whole blood, serum, plasma, cerebral-spinal fluid, or saliva more preferably, serum.

Measuring the Amount of Analyte * * * Quantitative, semiquantitative, and qualitative methods as well as all other methods for determining analyte are considered to be methods of measuring the amount of analyte. For example, a method which merely detects the presence or absence of analyte in a sample suspected of containing an analyte is considered to be included within the scope of the present invention.

Synonyms for the phrase "measuring the amount of analyte" which are contemplated within the scope of the present invention include, but are not limited to, detecting, measuring, or determining analyte; detecting, measuring, or determining the presence of analyte; and detecting, or determining the amount of analyte.

Member of a Specific Binding Pair * * * A member of a specific binding pair (sbp member) is one of two different molecules, having an area on the surface or in a cavity which specifically binds to and is thereby defined as complementary with a particular spatial and polar organization of the other molecule. The members of the specific binding pair are referred to as ligand and receptor (antiligand), sbp member and sbp partner, or the like. These will usually be members of an immunological pair such as antigen-antibody, although other specific binding pairs, such as biotin-avidin, hormones-hormone receptors, nucleic acid duplexes, IgG-protein A, DNA-DNA, DNA-RNA, and the like, are not immunological pairs but are specific binding pairs.

Ligand * * * Any organic compound for which a receptor naturally exists or can be prepared. For example, in one context of the present invention, the analyte is a ligand and the present invention provides methods for determining the concentration of the analyte which is a ligand.

Receptor * * * A receptor is any compound or composition capable of recognizing a particular spatial and polar organization of a molecule. These organized areas of a molecule are referred to as epitopic or determinant sites. Illustrative naturally occurring receptors include: antibodies, enzymes, Fab fragments, poly(nucleic acids), complement component Clq, thyroxine binding globulin, lectins, protein A, and the like. Receptors are also referred to as antiligands.

Ligand, analyte or sbp member analog * * * A modified ligand or ligand surrogate, modified analyte or analyte surrogate, or modified sbp member or sbp member surrogate which can compete with the analogous ligand, analyte or sbp member for a receptor, antiligand, sbp partner, or the like, the modification providing means to join a ligand analog, analyte analog, or sbp member analog to another molecule. The ligand analog, analyte analog, or sbp member analog will usually differ from the ligand, analyte, or sbp member by more than replacement of a hydrogen with a bond which links the ligand analog, analyte analog, or sbp member analog to a hub or label, but need not. The term ligand surrogate, analyte surrogate, or sbp member surrogate refers to a compound having the capability of specifically binding a receptor complementary to the ligand, analyte or sbp member. Thus, the ligand surrogate, analyte surrogate, or sbp member surrogate can bind to the receptor in a manner similar to the ligand, analyte, or sbp member. The surrogate could be, for example, an antibody directed against the idiotype of an antibody to the ligand or analyte.

Linking Group * * * A linking group is a portion of a structure which connects 2 or more substructures. A linking group has at least 1 uninterrupted chain of atoms extending between the substructures. The atoms of a linking group are themselves connected by chemical bonds. The number of atoms in a linking group is determined by counting the atoms other than hydrogen.

Conjugate * * * A conjugate is a molecule comprised of two or more substructures bound together, optionally through a linking group, to form a single structure. The binding can be made either by a direct connection (e.g. a chemical bond) between the subunits or by use of a linking group. Within the context of the present invention, a conjugate is a G6PDH enzyme attached to a hapten, sbp member or analyte analog.

Conjugation * * * Conjugation is any process wherein two subunits are linked together to form a conjugate. The conjugation process can be comprised of any number of steps.

Hapten * * * Haptens are capable of binding specifically to corresponding antibodies, but usually do not themselves act as immunogens for preparation of the antibodies. Antibodies which recognize a hapten can be prepared against compounds comprised of the hapten linked to an immunogenic carrier. Haptens are a subset of ligands.

Signal Producing System * * * The signal producing system is utilized in assays for analytes and may have one or more components, at least one component being a mutant G6PDH of the invention. The signal producing system generates a signal that relates to the presence or amount of analyte in a sample. The signal producing system includes all of the reagents required to produce a measurable signal.

For purposes of the present invention, the signal-producing system includes at least one enzyme and at least one substrate, and may include two or more enzymes and a plurality of substrates, and may include a combination of enzymes, where the substrate of one enzyme is the product of the other enzyme; provided throughout that at least one enzyme of the signal producing system is a mutant G6PDH of the invention.

Typically, the mutant G6PDH is conjugated to an sbp member analogous to the analyte. When the label is not conjugated to an sbp member analogous to the analyte, the label is normally bound to an sbp member complementary to the analyte.

Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, other enzymes and catalysts, and the like.

The signal producing system provides a signal detectable by external means, normally by measurement of electromagnetic radiation, desirably by visual examination. For the most part, the signal producing system includes a chromophoric substrate and mutant G6PDH enzyme of the invention, where chromophoric substrates are enzymatically converted to dyes which absorb light in the ultraviolet or visible region, phosphors or fluorescers.

Ancillary Materials * * * Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Sensitivity * * * Is used in the sense of detection limit, i.e., the smallest amount of an analyte giving a signal that is distinguishable from the signal obtained in the absence of analyte.

Substantial Change in Enzyme Activity * * * A change in activity of an enzyme sufficient to allow detection of an analyte when the enzyme is used as a label in an assay for the analyte. Typically, the enzyme's activity is reduced 10–1000% preferably 20–990%, more preferably 30–950%.

Inhibitory Antibody * * * An antibody capable of inhibiting the activity of an enzyme or an enzyme-ligand conjugate upon bindin an epitope present on the enzyme. Such antibodies are distinguished from anti-ligand antibodies capable of inhibiting the enzyme activity of enzyme-ligand conjugates upon binding to the ligand.

Expression Vector * * * A DNA construct containing a DNA sequence which is operably linked to a suitable control sequence capable of effecting the expression of said DNA in a suitable host. Such control sequences may include a promoter to effect transcription, an optional operator sequence to control such transcription, a sequence encoding suitable MtRNA ribosome-binding sites, and sequences which control termination of transcription and translation. The vector may be a plasmid, a phage particle, or simply a potential genomic insert.

Recombinant or Mutant G6PDH * * * G6PDH in which the DNA sequence encoding the naturally occurring G6PDH is modified to produce a mutant DNA sequence which encodes the substitution, insertion or deletion of one or more amino acids in the G6PDH sequence.

G6PDH * * * A naturally occurring G6PDH or a recombinant G6PDH. Preferably an bacterial or fungal G6PDH, more preferably a bacterial G6PDH. Particularly preferred G6PDHs are bacterial $NAD^+$ dependent G6PDHs.

Precursor G6PDH * * * A naturally occurring G6PDH enzyme as well as a recombinant G6PDH enzyme having a sequence substantially identical to a naturally occurring G6PDH. The amino acid sequence of a G6PDH mutant is derived from the precursor G6PDH amino acid sequence by the substitution or deletion of one or more amino acids of the precursor amino acid sequence or the insertion of one or more amino acids into the precursor amino acid sequence. Such modification is of the precursor DNA sequence which encodes the amino acid sequence of the precursor G6PDH rather than manipulation of the precursor G6PDH enzyme per se.

Host Strains or Cells * * * Generally procaryotic or eucaryotic hosts and include any transformable microorganism in which the expression of G6PDH can be achieved.

SPECIFIC EMBODIMENTS

Homogeneous enzyme immunoassays depend on the availability of enzyme-sbp member conjugates whose enzyme activity can be strongly modulated on binding of the sbp partner. The present invention provides methods, enzymes, enzyme-sbp member conjugates, reagents and kits of reagents for conducting assays that are useful in immunoassays, especially homogeneous immunoassays.

One aspect of the present invention relates to methods for homogeneous immunoassay of an analyte in a sample suspected of containing the analyte. The methods comprise the steps of: (1) combining in a liquid medium: (a) the sample to be assayed, (b) a conjugate of the analyte or an analyte analog with a mutant $NAD^+$ dependent G6PDH differing from any precursor G6PDH by the deletion, substitution, or insertion or any combination thereof of at least one amino acid per subunit, (c) a receptor for the analyte, and (d) substrates for the G6PDH; (2) determining the enzymatic activity of the G6PDH in the medium; and (3) comparing the activity to the enzymatic activity observed with a sample containing the analyte.

Accordingly, the present invention includes a mutant G6PDH differing from any precursor G6PDH by the deletion, substitution, or insertion or any combination thereof of at least one amino acid per subunit as well as a conjugate of such a mutant G6PDH and an analog of the analyte or a receptor for the analyte. The mutations are selected to improve the properties of G6PDH conjugate. Typically, the improvement involves the performance of the G6PDH as a detectable label in binding assays, particularly, immunoassays. Frequently, the immunoassay to be improved is a homogeneous immunoassay wherein the G6PDH is conjugated to a specific binding pair (sbp) member and the improvement comprises an increase in stability or modulation of enzyme activity upon binding of the sbp partner or a higher activity of the enzyme conjugate relative to precursor enzyme.

The DNA encoding any $NAD^+$ utilizing G6PDH is suitable for performing the mutations of the present invention. The encoded enzyme may be capable of using both $NADP^+$ and $NAD^+$ such as L. mesenteroides, A. suboxydans, P. aeruginosa, Pseudomonas W6, H. eutropha H-16, Hydrogenomonas facilis, Arthrobacter 7C, A. beijerickii, T. ferrooxidans, B. licheniformis, P. denitrificans, C. crescentus, L. lactis, and R. spheroides. Alternatively, the encoded enzyme may be capable of using $NAD^+$ as a preferred cofactor such as P. fluorescens and one of the G6PDHs from P. multivorans, or may be $NAD^+$ specific such as one of the G6PDHs from A. xylinum.

For example, Leuconostoc mesenteroides glucose-6-phosphate dehydrogenases (G6PDH) are dimeric enzymes that have the ability to catalyze the oxidation of D-glucose-6-phosphate to D-glucono-δ-lactone-6-phosphate by utilizing either $NAD^+$ or $NADP^+$. This property of using $NAD^+$ differentiates these enzymes from human G6PDH, which utilizes only $NADP^+$ effectively, and allows L. mesenteroides-specific G6PDH activity to be measured in the presence of human G6PDH, as for example in human samples. Glucose-6-phosphate dehydrogenases from L. mesenteroides are used in current EMIT homogeneous immunoassays (EMIT is a Trademark of Syva Company, Palo Alto, Calif., U.S.A.).

Two preferred genera of bacteria from which to select DNA encoding G6PDH are Leuconostoc and Zymomonas. Within these genera L. mesenteroides, L. citreum, L. lactis, L. dextranicum, and Z. mobilis are preferred, L. mesenteroides, L. citreum, L. lactis being particularly preferred. Because G6PDH from Leuconostoc does not contain cysteine residues, it is preferred for mutation strategies wherein one or more cysteine residues are introduced.

Table 1 describes exemplary strains of a variety of Leuconostoc species. Such strains are purely exemplary and do not limit the selection of DNA suitable for use within the context of the present invention to that of any particular genus, species or strain. Among the most preferred strains from which to select DNA encoding G6PDH are Leuconostoc mesenteroides strain ATCC 12291, Leuconostoc citreum strain NCIMB 3351, Leuconostoc lactis strain NCDO 546, and Leuconostoc dextranicum strain ATCC 19255.

TABLE 1

Organisms from the American Type Culture Collection (ATCC)[1]

Leuconostoc amelibiosum: ATCC 10882, and ATCC 13146.
Leuconostoc carnosum: ATCC 49367.
Leuconostoc citreum: ATCC 49370.
Leuconostoc gelidum: ATCC 49366.
Leuconostoc lactis: ATCC 15520, and ATCC 19256.
Leuconostoc mesenteroides subsp. cremoris: ATCC 19254.
Leuconostoc mesenteroides subsp. dextranicum: ATCC 8086, ATCC 17071, ATCC 17072, and ATCC 19255.
Leuconostoc mesenteroides subsp. mesenteroides: ATCC 8293, ATCC 9135, ATCC 10830, ATCC 10830a, ATCC 10877, ATCC 10878, ATCC 10879, ATCC 10880, ATCC 10883, ATCC 11449, ATCC 12291, ATCC 14430, ATCC 14935, ATCC 23386, ATCC 27258.
Leuconostoc oenos: ATCC 23277, ATCC 23278, ATCC 23279, ATCC 27307, ATCC 27308, ATCC 27309, ATCC 27310, ATCC 27311, ATCC 39401, and ATCC 39402.
Leuconostoc paramesenteroides: ATCC 33313.
Leuconostoc pseudomesenteroides: ATCC 49371.
Leuconostoc sp.: ATCC 21435, ATCC 21436, and ATCC 21437.

Organism from the National Collections of Industrial and Marine Bacteria (NCIMB)[2]

Leuconostoc carnosum: NCIMB 12898.
Leuconostoc citreum: NCIMB 3351.
Leuconostoc gelidum: NCIMB 12897.
Leuconostoc mesenteroides subsp. cremoris AL: NCIMB 12008.
Leuconostoc mesenteroides subsp. dextranicum AL: NCIMB 2706, NCIMB 3355, NCIMB 3356, NCIMB 3740, NCIMB 8189, NCIMB 8723, NCIMB 9312, NCIMB 9313, and NCIMB 12007.
Leuconostoc mesenteroides subsp. mesenteroides AL: NCIMB 3352, NCIMB 3354, NCIMB 3739, NCIMB 6109, NCIMB 6992, NCIMB 8013, NCIMB 8015, NCIMB 8023, NCIMB 8029, NCIMB 8172, NCIMB 8590, NCIMB 8710, NCIMB 8724, NCIMB 9260, NCIMB 9314, NCIMB 9315, NCIMB 9316, NCIMB 9319, and NCIMB 10488.
Leuconostoc oenos AL: NCIMB 11648.
Leuconostoc pseudomesenteroides: NCIMB 8699.

[1]Data format and abbreviations as in American Type Culture Collection, Catalogue of Bacteria and Phages, Eighteenth edition, 1992, American Type Culture Collection, 12301 Parklawn Drive, Rockville, Maryland 20852-1776.
[2]Data format and abbreviations as in The National Collections of Industrial and Marine Bacteria Limited, Catalogue of Strains, 1990, NCIMB Ltd., 23 St., Machar Drive, Aberdeen, Scotland, U.K. AB2 1RY.

The DNA sequence of the G6PDH gene from L. mesenteroides strain ATCC 12291, determined as described below, is provided as FIG. 1 (SEQ ID NO:1) and the amino acid sequence for the corresponding G6PDH is provided as FIG. 2 (SEQ ID NO:2). The DNA sequence of the G6PDH gene from L. citreum strain NCIMB 3351, determined as described below, is provided as FIG. 3 (SEQ ID NO:3) and the amino acid sequence for the corresponding G6PDH is provided as FIG. 4 (SEQ ID NO:4). The DNA sequence of the G6PDH gene from L. lactis strain NCDO 546, determined as described below, is provided as FIG. 5 (SEQ ID NO:5) and the amino acid sequence for the corresponding G6PDH is provided as FIG. 6 (SEQ ID NO:6). The DNA sequence of the G6PDH gene from *L. dextranicum* strain ATCC 19255, as described in Canadian Patent Application Number 2,045,838 A1, is provided as FIG. 7 (SEQ ID NO:7) and the amino acid sequence for the corresponding G6PDH is provided as FIG. 8 (SEQ ID NO:8). Exemplary mutations are described below. These are exemplary approaches and in no way limit the scope of the present invention. For example, mutations, other than those set forth below, could provide increased stability, modulability or specific activity of the mutant G6PDH as compared to the precursor G6PDH by inserting, deleting, or substituting amino acids at sites affecting such properties.

First Mutation Scheme

The immunoassay to be improved by the present invention is one wherein the label enzyme (G6PDH), is conjugated to a specific binding pair (sbp) member. As described below, the enzymatic activity of such a conjugate is modulated, usually inhibited, by binding of an sbp partner to the conjugate. G6PDH-sbp member conjugates are generally formed by covalently binding or conjugating an sbp member to a G6PDH through a linker to a reactive amino acid such as tyrosine, lysine, cysteine, histidine and the like.

However, not all reactive amino acids will react with an sbp member to form a conjugate that is readily modulatable in a homogeneous immunoassay. For example, linking of a hapten to *Leuconostoc mesenteroides* wild type G6PDH through a carboxyl or tyrosine gives poorly modulatable conjugates. If a hapten is linked to G6PDH through the free primary amino group of lysine residues and/or the N-terminus of the enzyme, the resulting conjugate mixture usually has reduced activity and may have limited ability to be modulated by anti-hapten antibody because binding of the sbp member to different groups on the enzyme can result in deactivation, destabilization, reduced modulability, or no affect depending on the particular group or set of groups that becomes bound.

Accordingly, one mutation scheme for improving the performance of G6PDH as a label in homogeneous immunoassays provides enzymes that form conjugates having higher enzymatic activity when the sbp member is not bound to its sbp partner and having a greater reduction in enzymatic activity when the sbp member is bound to its sbp partner relative to the corresponding properties of a precursor enzyme conjugated to a like number of sbp members.

Exemplary of such a scheme is the elimination of lysine residues that, when conjugated to sbp members, contribute little to the modulability by an sbp partner. These lysines can be eliminated by deleting them from the protein sequence or, preferably, by substituting them with other amino acids that have no detrimental effect on the protein stability. The replacement amino acids are any amino acids that do not substantially, adversely affect the activity or stability of the enzyme and preferably an amino acid that preserves the charge of the enzyme such as arginine or histidine.

The mutations of this scheme involve deletion or substitution of one, preferably two, more preferably at least four lysine amino acid residues per subunit. The mutations preferably further involve substitution of the lysines by a different amino acid residue.

Lysines to be deleted or substituted can be selected in any manner. For example, they can be replaced one at a time, examining the enzyme activity of the conjugate with and without sbp partner, to determine suitable mutants. Preferably, if it is known which lysines upon conjugation produce inactive conjugates or do not contribute to modulation, then these lysines are candidates for deletion or substitution. Lysines of this type can be identified, for example, by systematically deleting lysines that react during conjugation of a precursor enzyme where these lysines can be identified for example by sequencing tryptic digestion fragments of the conjugate to determine which amino acids are linked to sbp members.

One class of mutant G6PDH enzymes having such mutations are those mutant G6PDH enzymes having lysines deleted or substitution in one or more amino acid residue positions selected from the group consisting of positions 5, 19, 31, 32, 37, 55, 63, 96, 105, 128, 131, 148, 204, 208, 252, 259, 265, 273, 282, 298, 311, 338, 343, 352, 376, 382, 386, 408, 409, 441, 454, 461, 472, and 484 in G6PDH from *L. mesenteroides* strain ATCC 12291, preferably from positions 5, 19, 37, 128, 131, 204, 252, 265, 282, 338, 343, 454, 461, and 472. Preferably, at least two lysines are deleted or substituted, more preferably at least 4, most preferably 6 or more lysines are deleted or substituted wherein at least 1 and preferably at least 4 of the lysines substituted are selected from the above group of positions.

Another class of mutant G6PDH enzymes having such mutations are those mutant G6PDH enzymes having lysines deleted or substituted from one or more positions selected from the group consisting of positions 5 19, 31, 32, 55, 69, 96, 105, 128, 131, 148, 162, 204, 208, 252, 259, 265, 273, 282, 298, 311, 338, 343, 352, 376, 382, 386, 408, 441, 454, 461, 472, and 484 in G6PDH from *L. citreum* strain NCIMB 3351, preferably from positions 5, 19, 69, 128, 131, 204, 252, 265, 282, 338, 343, 454, 461, and 472. Preferably, at least two lysines are deleted or substituted, more preferably at least 4, most preferably 6 or more lysines are deleted or substituted wherein at least 1 and preferably at least 4 of the lysines substituted are selected from the above group of positions.

Another class of G6PDH enzymes having such mutations are those mutant G6PDH enzymes having lysines deleted or substituted from one or more positions selected from the group consisting of positions 5, 19, 31, 32, 55, 69, 96, 105, 128, 131, 148, 159, 204, 208, 252, 259, 265, 273, 282, 298, 311, 338, 343, 352, 382, 386, 408, 441, 454, 461, 472, and 484 in G6PDH from *L. lactis* strain NCDO 546, preferably from positions 5, 19, 128, 131, 204, 252, 265, 282, 338, 343, 454, 461, and 472. Preferably, at least two lysines are deleted or substituted, more preferably at least 4, most preferably 6 or more lysines are deleted or substituted wherein at least 1 and preferably at least 4 of the lysines substituted are selected from the above group of positions.

Another class of G6PDH enzymes having such mutations are those mutant G6PDH enzymes having lysines deleted or substituted from one or more positions selected from the group consisting of positions 5, 19, 31, 32, 55, 63, 96, 128, 131, 148, 204, 208, 252, 259, 265, 273, 282, 298, 311, 338, 343, 352, 376, 382, 386, 408, 409, 441, 454, 461, 472, and 484 in G6PDH from *L. dextranicum* strain ATCC 19255, preferably from positions 5, 19, 128, 131, 204, 252, 265, 282, 338, 343, 454, 461, and 472. Preferably, at least two lysines are deleted or substituted, more preferably at least 4, most preferably 6 or more lysines are deleted or substituted wherein at least 1 and preferably at least 4 of the lysines substituted are selected from the above group of positions.

Generally, any precursor G6PDH having a high degree of homology with the exemplary strains listed above is a candidate for the above exemplary mutations. Such homology is not a requirement of the first mutation strategy. However, homology is one method of identifying candidate strains. The degree of homology may be 50–80%, preferably 80–850%, more preferably >85%.

Second Mutation Scheme

In homogeneous binding assays using sbp member-enzyme conjugates, it is sometimes difficult to attach a given sbp member to a label enzyme so that the resulting conjugate has substantial enzyme activity when not bound to an sbp partner but has substantially reduced enzyme activity (is inhibited) when bound to an sbp partner. One reason for this difficulty may be that there are no sites on the enzyme to which an sbp member can be attached that will provide the desired inhibition. This can occur when all sites that have functional groups to which an sbp member can be bound to the enzyme are incapable of providing inhibition or when binding of an sbp member to a functional group capable of providing inhibition leads to substantial loss of enzyme activity. Exemplary functional groups to which an sbp member may be bound include by way of example and not limitation, hydroxyl, carboxyl, amino, sulfhydryl, and the like. Exemplary of such functional groups to which an sbp member may be bound are the hydroxy group of tyrosine, serine, and threonine; the carboxy group of aspartic acid and glutamic acid; the amine group of lysine; and the sulfhydryl group of cysteine.

Accordingly another exemplary mutation scheme of the present invention results in improving the inhibitability of enzyme-sbp member conjugates by providing one or more sbp member attachment sites at locations on the enzyme not otherwise having such attachment sites. Providing attachment sites can involve adding one or more new residues (having such a functional group) to a protein sequence or substituting one or more existing residues (not having such a functional group) with new residues (having such a functional group).

For example, because G6PDH from many strains of *L. mesenteroides* lack cysteine residues, cysteine residues can be provided (by insertion or substitution) that allow sbp members to be bound (through free sulfhydryl of the new cysteine residues) to sites on the enzyme not otherwise available. The number of cysteine residues introduced depends on the nature of the assay to be performed. Generally, a small number of cysteines at sites selected to allow for the formation of conjugates that are inhibitable upon binding of the sbp member is preferred. Accordingly, the mutations of this scheme preferably involve introduction of cysteine residues, usually up to 8 cysteines, per subunit, preferably up to 4 cysteines and most preferably, a single cysteine residue per subunit.

One class of preferred mutant G6PDH enzymes are those mutant G6PDH enzymes having at least one cysteine residue introduced between amino acids 35 and 70, preferably, 45 and 60, more preferably, 45 and 57 in G6PDH from *Leuconostoc mesenteroides* strain ATCC 12291, *Leuconostoc citreum* strain NCIMB 3351, *Leuconostoc lactis* strain NCDO 546, or *Leuconostoc dextranicum* strain ATCC 19255 wherein the cysteine preferably replaces one of these amino acids, but need not.

Table 2 lists exemplary cysteine introductions consistent with this mutation scheme. Such mutations are purely exemplary and do not limit suitable mutations within the context of the present invention.

TABLE 2

Cysteine Introduction Mutations

*Leuconostoc mesenteroides* ATCC 12291

Ala-45-Cys
Arg-46-Cys

TABLE 2-continued

Cysteine Introduction Mutations

Gln-47-Cys
Ala-48-Cys
Leu-49-Cys
Asn-50-Cys
Asp-51-Cys
Asp-52-Cys
Glu-53-Cys
Phe-54-Cys
Lys-55-Cys
Gln-56-Cys
Leu-57-Cys
Val-58-Cys
Arg-59-Cys
Asp-60-Cys
Lys-128-Cys
Lys-182-Cys

*Leuconostoc citreum* NCIMB 3351

Lys-21-Cys
Ala-45-Cys
Arg-46-Cys
Gln-47-Cys
Asp-48-Cys
Leu-49-Cys
Thr-50-Cys
Asp-51-Cys
Ala-52-Cys
Glu-53-Cys
Phe-54-Cys
Lys-55-Cys
Gln-56-Cys
Leu-57-Cys
Val-58-Cys
Arg-59-Cys
Glu-60-Cys
Asp-48-Ala, and Ala-52-Cys

*Leuconostoc lactis* NCDO 546

Ala-45-Cys
Arg-46-Cys
Gln-47-Cys
Asp-48-Cys
Leu-49-Cys
Thr-50-Cys
Glu-51-Cys
Asp-52-Cys
Glu-53-Cys
Phe-54-Cys
Lys-55-Cys
Gln-56-Cys
Leu-57-Cys
Val-58-Cys
Arg-59-Cys
Asp-60-Cys

*Leuconostoc dextranicus* ATCC 19255

Ala-45-Cys
Arg-46-Cys
Gln-47-Cys
Asp-48-Cys
Leu-49-Cys
Thr-50-Cys
Glu-51-Cys
Asp-52-Cys
Glu-53-Cys
Phe-54-Cys
Lys-55-Cys
Gln-56-Cys
Leu-57-Cys
Val-58-Cys
Arg-59-Cys
Asp-60-Cys

Third Mutation Scheme

Another exemplary mutation scheme involves inhibitory epitopic sites (IES) present on a given enzyme. Suitable inhibitory epitopic sites as well as methods for using such sites in assays is contained in Skold, C., D. R. Gould, and E. F. Ullman (Methods for modulating ligand-receptor interactions and their application; U.S. Pat. No. 4,727,022, Feb. 23, 1988; filed Mar. 14, 1984) which is incorporated in its entirety herein by reference, particularly, column 1, lines 40–59, and column 2, lines 26–38. An IES is a site on an enzyme that binds an inhibitory antibody (IA) such that, when the IA is bound, the activity of the enzyme is substantially reduced but, when the IA is not bound, the enzyme is active. There may be one or a plurality of IES's present on a given enzyme. Normally G6PDH will have at least two IES's. In some cases the IA may have to bind two IES's simultaneously to substantially reduce the enzyme activity. Often the enzyme will be a multiunit enzyme having a number of identical subunits, each bearing one or more IES's.

In this third mutation scheme, an enzyme having an IES is modified to provide sbp member attachment sites at one or more locations proximate to the IES so that when an sbp partner of the sbp member is bound to the enzyme-sbp member conjugate, the inhibitory antibodies will be inhibited from binding to the IES. In this scheme, an immunoassay is available which utilizes the enzyme conjugate; an sbp partner, usually an antibody capable of binding both the analyte and the conjugate; an inhibitory anti-G6PDH antibody; the G6PDH substrates glucose-6-phosphate (G6P) and $NAD^+$ or analogs thereof; and ancillary reagents. The activity of the enzyme conjugate is substantially inhibited in the presence of analyte (an sbp member), and active in the absence of analyte. When analyte is present, it competes with enzyme-sbp member conjugate for binding to the sbp partner (an antibody capable of binding analyte), and less sbp partner is then available to bind the conjugate. Inhibitory antibody also competes with sbp partner for binding to the enzyme sbp conjugate. Because binding of the sbp partner to the conjugate does not substantially inhibit the enzyme activity, the enzyme is active when the sbp partner binds. However, when the sbp partner is bound to analyte it cannot compete with the inhibitory antibody for binding to the conjugate, and the enzyme activity is reduced.

An IES can be naturally present on a precursor enzyme or can be created by modification of a precursor enzyme. A site for specific attachment of a ligand proximate to an IES will frequently not be available on a precursor enzyme but may be introduced by a mutation. Usually there will be at least one, frequently two or more IES's per subunit. Because G6PDH's are typically comprised of at least 2 identical subunits, a given G6PDH may have one or more pairs of identical inhibitory epitopic sites. Certain antibodies are capable of binding simultaneously to each member of such a pair. In such a case the inhibitory antibody may be able to bridge the subunits when bound to the inhibitory epitopic sites.

Inhibitory monoclonal antibodies can be obtained by the process discussed by Milstein and Kohler and reported in *Nature* 1975, 256, 495–7. The details of this process are well known and will not be repeated here. However, basically it involves injecting a host, usually a mouse or other suitable animal, with an immunogen. Generally, the immunogen is the enzyme against which inhibitory antibodies are to be prepared. However, fragments of the enzyme or synthetic poly(peptides) mimicking the IES of the enzyme may also be used as the immunogen. Such enzyme fragment or synthetic poly(peptide) immunogens may incorporate one of the immunogenic carriers common in the art. Cells are then taken from the spleen of the animal. Alternatively, the host may be unsensitized spleen cells, which are sensitized to the immunogen in vitro. The resulting cells are fused with myeloma cells. The result is a hybrid cell, referred to as a "hybridoma" that can be cultured in vitro. The population of hybridomas is screened and manipulated so as to isolate individual clones, each of which secretes a single antibody to the antigen.

Skold, C., I. Gibbons, D. Gould, and E. F. Ullman (1987; Monoclonal antibodies to glucose-6-phosphate dehydrogenase (G6PDH) form cyclic 1:1 complexes with G6PDH and act as regulatory subunits; *J. Immunology* 138:3408–3414; which is incorporated herein by reference) describes the preparation of inhibitory antibodies to G6PDH from *L. mesenteroides*. In particular, the "Materials and Methods" section beginning at page 3408, column 2, paragraph 3, and ending after page 3409, column 1, paragraph 8, and the "Results" section beginning at page 3409, column 1, paragraph 8, and ending after page 3412, column 1, last paragraph, are incorporated herein by reference. Further, the above incorporated U.S. Pat. No. 4,727,002 discloses the preparation of such antibodies, in particular Example 5, column 11, line 1, to column 12, line 17, and Example 1, column 7, line 36, to column 8, line 14, are incorporated herein by reference.

For a given enzyme/inhibitory antibody pair, the IES can be located in a variety of ways, For example, epitope mapping such as described by Geysen, E. M., S. J. Rodda, T. J. Manson, G. Tribbick, and P. G. Schoofs (1987; Strategies for epitope analysis using peptide synthesis; *J. Immunol. Methods* 102:259–274) can be performed. Alternatively, the binding of IAs to various differing strains of G6PDH, such as described below, with known amino acid sequences can be determined. By comparing amino acid sequences among the binders and non-binders of the particular IA a number of possible binding sites can usually be determined. The exact site can subsequently be determined either by mutagenizing a binding enzyme to incorporate a non-binding amino acid sequence in a region suspected of being an IES and subsequently checking whether IA binding has been prevented or by splicing regions of a binding enzyme into a non-binding enzyme and determining whether an IES has been created.

Once the IES has been located, an sbp member attachment site can be added by introducing an amino acid residue proximate to the IES having a side chain bearing a functional group capable of reacting to form an enzyme-sbp member conjugate. Preferably the side chain will have a sulfhydryl group or a disulfide but side chains having other groups such as amino, imidazole and indole and hydroxyl can be used. Frequently the amino acid that is introduced will replace an amino acid that is normally found in the precursor enzyme.

The location of the new sbp member attachment site is selected so that, when sbp partner is bound to an enzyme-sbp member conjugate, an inhibitory antibody is substantially incapable of binding the conjugate. The new sbp member attachment site is also located so that the inhibitory antibody is capable of binding and inhibiting the conjugate when sbp partner is absent.

The new sbp member attachment site is preferably proximate to the IES. It may be characterized as proximate in 3-dimensional space or proximate along the amino acid sequence of the enzyme. If the attachment site is characterized as proximate in a spacial sense, it is usually within about 35 Å of an amino acid residue of the IES, preferably within about 30 to 3 Å, most preferably, 15 to 3 Å. If the attachment site is characterized as proximate in a sequence sense, it is preferably within about 10 amino acid residues of an amino acid residue of the IES, more preferably, within about 6 to 1, most preferably, 4 to 1.

A mutation of this scheme is any mutation proximate to an epitopic site which is recognized by an anti-G6PDH antibody capable of inhibiting the activity of the precursor G6PDH. The antibody may but need not be capable of simultaneously binding to two of the subunits within the same G6PDH molecule. One preferred mutation is the introduction (or insertion) of at least one cysteine residue per subunit.

Representative precursor G6PDH enzymes suitable for introducing such mutations include L. mesenteroides strain ATCC 12291, L. lactis strain NCDO 546 and L. dextranicus strain ATCC 19255. Four or more cysteine residues can be introduced by insertion or substitution between amino acids 45 and 60, and preferably, no more than 2, more preferably, a single cysteine can be introduced. Preferably, a single cysteine is introduced by substitution of the naturally present amino acid at position 51–56, most preferably position 52.

The mutant G6PDH conjugates of the present invention can be utilized in an assay of an analyte in a sample suspected of containing analyte. In one embodiment the assay comprises the steps of contacting the sample with antibodies capable of binding the analyte and an enzyme conjugate of the analyte and measuring the activity of the enzyme which relates to the amount of analyte in the sample. The improvement provided in this aspect of the invention is the utilization of the mutant G6PDH conjugates of the invention. The enzyme activity is determined by adding glucose-6-phosphate and $NAD^+$ or $NADP^+$, usually $NAD^+$ to the assay medium and detecting either the disappearance of one of these substrates or the appearance of NADH, NADPH or D-glucono-δ-lactone-6-phosphate.

In another configuration of an assay for the determination of analyte in an optionally pretreated sample suspected of containing analyte, the sample is contacted with antibodies for analyte inhibitory antibodies for G6PDH and a mutant G6PDH-analyte conjugate of the invention recognized by the antibodies for the analyte and the inhibitory antibodies for G6PDH. The method further includes measuring the enzyme activity in relation to the amount of analyte present in the sample. Analyte or analyte analog is conjugated, optionally through a linking group that will usually be less than about 50, preferably less than 20, more preferably less than about 6 atoms other than hydrogen having a chain of usually not more than about 35, preferably less than 15, more preferably less than 4 atoms in length, to a mutant G6PDH of the invention may be employed as the G6PDH conjugate.

The compositions of the invention have special application to homogeneous immunoassays for analytes exemplified by enzyme multiplied immunoassay techniques (e.g. see U.S. Pat. No. 3,817,837), and enzyme protection immunoassays (e.g. see U.S. Pat. No. 4,233,401) other homogeneous enzyme immunoassays are discussed in "Enzyme-Immunoassay" by Edward T. Maggio, CRC Press Incorporated, Boca Raton, Fla., 1980. Assays using inhibitory antibodies as described above are described in the above incorporated U.S. Pat. No. 4,727,022, in particular, column 5, line 16, to column 6, line 51, are incorporated herein by reference. The disclosures of the above patents not otherwise incorporated are incorporated herein by reference in their entirety as to the description of the particular assay methods mentioned.

The assay is preferably homogeneous and will normally be carried out in an aqueous buffered medium at a moderate pH, generally that which provides optimum assay sensitivity.

The aqueous medium may be solely water or may include from 0 to 40 volume percent of a cosolvent. The pH for the medium will usually be in the range of about 4 to 11, more usually in the range of about 5 to 10, and preferably in the range of about 6.5 to 9.5. The pH will usually be a compromise between optimum binding of the binding members of any specific binding pairs and the pH optimum for other reagents of the assay such as members of the signal producing system.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from about 5° to 45° C., more usually from about 150 to 40° C. Temperatures during measurements will generally range from about 100 to 500, more usually from about 15° to 40° C.

The concentration of analyte that may be assayed will generally vary from about $10^{-5}$ to $10^{-13}$ M, more usually from about $10^{-6}$ to $10^{-8}$ M. Considerations such as whether the assay is qualitative, semiquantitative or quantitative (relative to the amount of analyte present in the sample), the particular detection technique and the concentration of the analyte will normally determine the concentrations of the various reagents.

While the concentrations of the various reagents in the assay medium will generally be determined by the concentration range of interest of analyte, the final concentration of each of the reagents will normally be determined empirically to optimize the sensitivity of the assay over the range. That is, a variation in concentration of analyte which is of significance should provide an accurately measurable signal difference.

While the order of addition may be varied widely, there will be certain preferences depending on the nature of the assay. The simplest order of addition is to add all the materials simultaneously and determine the effect that the assay medium has on the signal. Alternatively, the reagents are combined sequentially. Optionally, an incubation step is involved subsequent to each addition, generally ranging from about 10 seconds to 6 hours, more usually from about 30 seconds to 1 hour.

In a homogeneous assay after all of the reagents have been combined either simultaneously or sequentially, the signal is determined. The signal is related to the amount of analyte in the sample tested. For example, when carrying out the enzyme multiplied immunoassay technique, as described in U.S. Pat. No. 3,817,837 (1974) the disclosure of which is incorporated by reference, for the detection of analyte by means of the present invention, a sample suspected of containing analyte is combined in an aqueous medium either simultaneously or sequentially with an antibody and a mutant G6PDH-analyte analog conjugate of the present invention.

Generally, substrates for the mutant G6PDH such as glucose-6-phosphate and $NAD^+$, $NADP^+$ or a derivative thereof are added which result in the formation of a chromogenic or fluorogenic product upon enzyme catalyzed reaction. The analyte in the sample and the mutant G6PDH-analyte analog conjugate compete for sites on the antibody. The enzyme activity in the medium is then determined, usually by spectrophotometric means, and is compared to the enzyme activity determined when a calibrator or reference sample is tested in which a known amount of analyte is present. Typically, the calibrator or reference sample is tested in a manner substantially the same as the sample suspected of containing analyte. Generally, a comparison can be made of the result from an unknown sample with the results of assay runs on several standard samples. The standard samples will typically contain differing, but known, concentrations of the analyte to be determined. Preferably, the concentration ranges present in the standard samples will span the range of suspected analyte concentrations in the unknown samples.

A similar procedure is employed for carrying out enzyme protection assays as described in U.S. Pat. No. 4,233,401 except that the mutant G6PDH analyte analog conjugate is capable of inhibition by an anti-G6PDH antibody which is included in the assay mixture.

Another aspect of the present invention relates to compositions comprising a specific binding pair member conjugated to a mutant $NAD^+$ dependent bacterial glucose-6-phosphate dehydrogenase (G6PDH) having at least one amino acid mutation per subunit as compared to precursor G6PDH. Analyte or analyte analog conjugated, optionally through a linking group of less than about 50, preferably less than 20, more preferably less than about 6 atoms other than hydrogen having a chain of usually not more than about 35, preferably less than 15, more preferably less than 4 atoms in length, to a mutant G6PDH of the invention may be employed as the conjugate.

One embodiment of such a conjugate is illustrated by the formula:

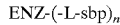

wherein ENZ is a mutant bacterial glucose-6-phosphate dehydrogenase (G6PDH) having at least one cysteine residue per subunit, L is a bond to the sulfur atom of the cysteine or a linking group having a chain of 1 to 20 atoms bonded to the sulfur atom of the cysteine, sbp is a specific binding pair member, and n is a number from 1 to 8. Preferably, L is a bond or linking group having a chain of less than 15 atoms, more preferably, L is a linking group having a chain of less than 4 atoms.

Conjugates of the invention are prepared by linking a hapten to a mutant G6PDH. When a functional group suitable for linking the hapten is not available a linking group will be introduced that contains a suitable functional group. The linking group may comprise a chain of atoms of 0 to 50 usually less than 15, more usually less than 6 in length. The length of the linking group will normally be determined empirically so as to provide G6PDH conjugates that have high modulation of activity by antibodies, low loss of activity upon conjugation, and high stability. The functional groups suitable for attaching the hapten to the enzyme will usually be an activated ester or alkylating agent when the amino acid(s) that are to be conjugated on the G6PDH have amino or hydroxyl groups and will usually be alkylating agents or desulfurizes when the amino acid(s) that are to be conjugated on the G6PDH are cysteine. A large number of suitable functional groups are available for attaching to aminos and alcohols such as activated esters including imidic esters, sulfonic esters and phosphate esters, activated nitrites, aldehydes, ketones, alkylating agents and the like.

Conjugation of haptens to proteins using these and other attaching groups are well known in the art and are described in reviews such as for example, Maggio, E. T. "Enzyme-Immunoassay" (CRC Press, Boca Raton, Fla., 1980), Chapter 4, contains an assortment of conjugation techniques; pages 81–88 of which are incorporated herein by reference.

Following reaction of mutant G6PDH with a hapten to form a conjugate the product is then optionally purified as may be required. The purification and characterization of poly(amino acid)-hapten conjugates has been described in detail Maggio, et. al; "enzyme-immunoassay" (CRC Press, Boca Raton, Fla., 1980), Chapter 4, pages 86–88 of which are incorporated herein by reference. For example, if the conjugate is a mutant G6PDH-hapten conjugate, the purification can be by dialysis against aqueous/organic and aqueous solutions such as water/DMF or water, or by gel filtration chromatography on supports such as Sephadex, and the like.

Alternatively, the conjugation can involve binding of a hapten to a free thio group present on an amino acid side chain of the enzyme (e.g. cysteine). Such conjugation involves alkylation of the thio sulfur atom by treatment with an electrophilic compound such as an $\alpha,\beta$-unsaturated amide, ketone, ester, or the like, or an alkylating agent such as a reactive halide or sulfonate or the like or reaction with an active disulfide such as a 2-nitro-4-carboxyphenyl disulfide. Specific examples by way of illustration and not limitation include $\alpha$-bromoamides, maleimides, vinyl sulfones, $\alpha$-iodoketones, triflates and the like.

Conjugation reactions with G6PDH can be affected by a number of factors. These include, but are not confined to, pH, temperature, buffer, ionic strength, substances which may protect the enzyme active site, amount and type of cosolvent, reaction time, and activation chemistry. For each enzyme-hapten combination, appropriate manipulation of these variables can lead to conjugates which are improved in one or more of the following properties: 1) reduced deactivation for a given amount of inhibition; 2) larger standard curve; 3) improved assay precision; 4) enhanced thermal stability. Keeping in mind that these variables are not independent, the following observations can be made. A range of pH values from 5.0 to 9.5 can usually be used for conjugation reactions. These reactions are generally carried out at 0–40° C., preferably 4–20° C. A number of buffers and salts, both alone and in combination, can be used for such reactions. These include Tris, bicarbonate, phosphate, pyrophosphate, EDTA, KCl, NaCl, and many others. The active site may be protected by substrates (i.e. G6P), cofactors ($NAD^+$, NADH, $NADP^+$, NADPH) and cofactor analogs (thio-$NAD^+$,thio-NADH,thio-$NADP^+$, or thio-NADPH), and compounds which react reversibly with lysine (i.e. pyridoxal) to reduce deactivation of the enzyme during conjugation. Cosolvents which may enhance hapten solubility include, but are not limited to, dimethylformamide, carbitol, dimethyl sulfoxide, 1-Methyl-2-pyrrolidinone, and 1,3-Dimethyl-3,4,5,6-tetrahydro 2(1H)-pyrimidinone. These may be useful as 1–30% of the reaction volume. Reactions can vary from 15 minutes to many days, depending on the activation chemistry. Carboxylic compounds may be activated to form esters with N-Hydroxysuccinimide or its sulfo-analog, or to mixed anhydrides through reaction with carbitol chloroformate or t-butylchloroformate, or may be coupled directly using carbodiimides such as EDAC. For reaction with cysteine thiols on the enzyme, the hapten should contain a good leaving group such as I, Br or tosyl; alternatively, the hapten can contain a thiol, preferably activated with 2,2' dithiodipyridine or DTNB. Another method of conjugation, described in Rowley, G. L., D. Leung, and P. Singh (U.S. Pat. No. 4,220,722, Sep. 2, 1980, filed Feb. 10, 1978) involves modification of the enzyme with bromoacetyl containing reactants; the bromo groups are subsequently reacted with thiol-containing haptens. The reaction of enzyme with bromoacetyl modifier, and the bromoacetyl enzyme with the thiolated hapten, are subject to the same reaction condition variables described above.

Another aspect of the present invention relates to improved assay reagents for use in the determination of an analyte in a sample suspected of containing the analyte. The assay reagents include an analyte-label conjugate; and the improvement comprises employing as the label mutant glucose-6-phosphate dehydrogenase (G6PDH) enzymes having at least one mutation per subunit as compared to precursor G6PDH wherein the mutations are proximate to an epitopic site recognized by an anti-G6PDH antibody capable of inhibiting the activity of the precursor G6PDH. Preferably, the label conjugate reagent is comprised of the conjugate and an aqueous medium, the pH medium being optimized to balance, among any other considerations, the activity and stability of the label conjugate. In one of its preferred embodiments, the present invention relates to aqueous mutant G6PDH-sbp member conjugate reagents wherein the pH is 6–10, preferably 7–9, more preferably 7.5–8.5.

Another aspect of the present invention relates to kits for conducting an assay for the determination of a specific binding pair (sbp) member. The kits comprise in packaged combination an sbp partner of the sbp member and a composition which comprises the sbp member or an analog of the sbp member conjugated to a mutant $NAD^+$ dependent bacterial glucose-6-phosphate dehydrogenase (G6PDH) having at least one amino acid mutation per subunit as compared to precursor G6PDH. Additionally the kits may contain an inhibitory anti-G6PDH antibody.

Surface active additives, including bulking agents such as BLG or PEG; defoamers and surfactants such as tween-20, plurafac A38, triton X-100, pluronic 25R2, RSA, BSA, Mod-u-cyte, sol-u-pro, or the like; and other materials commonly used in the art can be added to improve solubility and reduce nonspecific binding of reagents and analyte to surfaces.

Anti-microbial agents such as azide thimerosal, gentamicin and the like can be added to assay reagents in order to extend the storage life of the reagents. In one of its most preferred embodiments, the present invention relates to assay reagents containing anti-microbial agents.

To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit may comprise as one or more reagents antibodies capable of binding analyte or inhibitory antibodies capable of inhibiting a G6PDH-analyte analog conjugate of the invention. The kit may also include the conjugates of the invention. The kit can further include other packaged reagents for conducting an assay including members of the signal producing system, ancillary reagents, and so forth.

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Another aspect of the present invention relates to a mutant glucose-6-phosphate dehydrogenase (G6PDH) enzyme that is the expression product of a mutated DNA sequence encoding a glucose-6-phosphate dehydrogenase, the mutant DNA sequence being derived from a precursor glucose-6-phosphate dehydrogenase by the deletion, insertion or substitution of one or more amino acids in the precursor glucose-6-phosphate dehydrogenase. Preferably, the G6PDH is an $NAD^+$ dependent bacterial G6PDH, more preferably the mutant DNA sequence is derived from a precursor glucose-6-phosphate dehydrogenase by the deletion, insertion or substitution of two or more amino acids in the precursor glucose-6-phosphate dehydrogenase.

Another aspect of the present invention relates to mutant glucose-6-phosphate dehydrogenase (G6PDH) enzymes having at least one mutation per subunit as compared to precursor G6PDH wherein the mutation is proximate to an epitopic site recognized by an anti-G6PDH antibody capable of inhibiting the activity of the precursor G6PDH.

To prepare the glucose-6-phosphate dehydrogenases (G6PDHs) and G6PDH conjugates described in this invention, it is first necessary to obtain genomic DNA that codes for the production of G6PDH from suitable Leuconostoc organisms. These DNAs can be cloned in *E. coli* cloning vectors. Colonies containing recombinant cloning vectors harboring the gene for G6PDH may be screened for by colony or plaque hybridization using labeled probes specific for the gene. Alternatively, the gene encoding G6PDH can be isolated by means of the polymerase chain reaction (PCR) using appropriate oligodeoxynucleotide primers. Suitable oligodeoxynucleotide probes and primers can be readily synthesized based on the nucleotide sequences of the G6PDH genes described below.

Once the gene encoding a particular G6PDH has been isolated and expressed, mutations causing changes in the amino acid sequence of the protein can be introduced by any of a number of methods of site-specific mutagenesis. Specific mutations which result in G6PDHs with improved properties for use as immunoassay conjugates are described below. Methods for the purification of non-recombinant Leuconostoc G6PDHs are well known in the literature. These same methods can be successfully applied to mutant recombinant G6PDHs as described below. Finally, the methods for the production of conjugates useful in immunoassays employing these purified mutant recombinant G6PDHs and the use of these conjugates in improved homogeneous immunoassays are described in the examples below.

The basic molecular biological techniques employed in accomplishing features of this invention, such as DNA and plasmid isolation, restriction enzyme digestion, DNA ligation, purification and characterization of DNAs by polyacrylamide and agarose gel electrophoresis, labeling and hybridization of DNAs, Southern blotting, maintenance and growth of bacterial strains, and other general techniques are all well know in the literature. Specifically, the general techniques of molecular biology are described in "Molecular Cloning A Laboratory Manual" by Sambrook, J., Fritsch, E. F., and Maniatis, T. published by Cold Spring Harbor Laboratory Press, 2nd edition, 1989, or "A Practical Guide to Molecular Cloning" by Bernard Perbal published by John Wiley & Sons, New York, 1984. Specific methods for obtaining the gene for G6PDH and expressing and purifying the protein are described below.

Another aspect of the present invention relates to mutant DNA sequences encoding such glucose-6-phosphate dehydrogenases (G6PDH) enzymes. These mutant DNA sequences are derived from a precursor DNA sequence which encodes a naturally-occurring or recombinant precursor enzyme. The mutant DNA sequences are derived by modifying the precursor DNA sequence to encode the substitution, deletion or insertion of at least one amino acid residue encoded by the precursor DNA sequence. These recombinant DNA sequences encode glucose-6-phosphate dehydrogenase mutant enzymes having a novel amino acid sequence.

Further the invention relates to expression vectors containing such mutant glucose-6-phosphate dehydrogenase DNA sequences as well as host cells transformed with such vectors which are capable or producing such mutant enzymes.

Another aspect of the present invention relates to engineered DNA sequences characterized by a nucleotide sequence encoding a glucose-6-phosphate dehydrogenase (G6PDH) enzyme produced by an organism for expression in a unicellular host, wherein the G6PDH has at least two amino acid mutations as compared to precursor G6PDH of the organism.

Further the invention relates to expression vectors containing such mutant glucose-6-phosphate dehydrogenase DNA sequences as well as host cells transformed with such vectors which are capable or producing such mutant enzymes.

Another aspect of the present invention relates to plasmids characterized by containing an engineered native DNA sequence encoding a glucose-6-phosphate dehydrogenase (G6PDH) enzyme for expression in a unicellular host, wherein the G6PDH has at least two amino acid mutations as compared to precursor G6PDH of the organism.

Another aspect of the present invention relates to transformed unicellular hosts characterized by the presence of a plasmid with an engineered DNA sequence encoding a glucose-6-phosphate dehydrogenase (G6PDH) enzyme wherein the G6PDH has at least two amino acid mutations as compared to precursor G6PDH of the organism.

The requirements for an expression vector will include a selectable, with an intracellular expression system from a strong, inducible promoter. To optimize expression, a vector having its own ribosome binding site (rbs) is preferred, rather than engineering the G6PDH gene. An example of such a plasmid, shown in FIG. 9, is pJS12 based on the vector pDR540, shown in FIG. 10, an ampicillin-selectable plasmid having a tac promoter and a Bam HI cloning site. The first two bases of the Bam HI site (<u>GA</u>ATTC) complete the sequence of the second rbs (AG<u>GA</u>) following the promoter. To achieve a desirable spacing (7–9 bases) between the rbs and the G6PDH start codon, the 5' end of a PCR fragment containing the gene, for example, can be designed so that the ATG is spaced 4 bases away from the end of the Bam HI site.

Another example of a useful plasmid, shown in FIG. 11, is pJS14 based on pKK233-2, shown in FIG. 12. This expression vector has several improvements as compared to pJS12 based on pDR540. It carries an Nco I site (CC<u>ATG</u>G), the ATG of which corresponds to the properly positioned start codon of the expressed protein. This start codon site eliminates the need to properly space the rbs and ATG sites. The vector also contains a transcriptional terminator sequence following the multiple cloning site, which reduces or eliminates run-on transcription from a plasmid.

Once the desired G6PDH DNA fragment has been successfully cloned into the expression vector, the resulting cells are tested for expression of desired G6PDH and absence of expression of native G6PDH. This is most readily done by enzymatic assay for activity of the recombinant G6PDH in the presence of $NAD^+$. Alternatively, western blots are performed on cell extracts using polyclonal antibodies that recognize the desired G6PDH but do not recognize other related but undesirable enzymes such as any native enzyme produced by the host cell without the plasmid. For example, a subunit of G6PDH from *L. mesenteroides* appears as a protein of approximately 54 kDa (on a denaturing polyacrylamide gel) and cross-reacts with the antibodies. This protein is present in cells containing the expression plasmid, but is absent in extracts of cells without the plasmid. Levels of the specific G6PDH protein generally increases when the cultures are incubated in the presence of isopropylthio-β-galactoside (IPTG), demonstrating that protein production is inducible.

The following examples further describe the specific embodiments of the invention. These are typical illustrative examples and are intended to describe and not to limit the scope of the invention.

EXAMPLES

Preparation of Genomic DNA from Leuconostoc Organisms

Genomic DNA was prepared from Leuconostoc organisms by the method of Murphy, N. B., McConnell, D. J., and Schwarz, T. F. R. *J. Bact.* 169(1), 334–339 (1987). Specific instructions for bacterial growth and DNA isolation are given on pages 334 and 335.

Cloning and expression of Leuconostoc G6PDHs

The cloning and expression of *Leuconostoc mesenteroides* G6PDH has been described by Lee, W. T., Flynn, T. G., Lyons, C., and Levy, H. R. *J. Biol. Chem.* 266(20), 13028–13034 (1991). This technology has further been set forth in International Pat. No. Publication Number WO92/07078 (International Application Number PCT/US91/07715).

Alternatively, the probe TG46 (5' AGG-TAG-TGG-TCA-ATA-CGG-AAT-AGT-TGG-TTA-TCA-TCA-AAT-GCG-TTT-T 3') can be used in Southern blotting experiments to identify restriction fragments containing the G6PDH gene. Specifically, in the cloning of G6PDH from the National Collection of Industrial and Marine Bacteria, Aberdeen, Scotland (NCIMB) 3351 (*Leuconostoc citreum*), Southern blot hybridization of NCIMB 3351 genomic DNA with the 46 base pair (bp) TG46 probe showed strongly hybridizing 2.7 kilo base pair (kb) Kpn I and 2.5 kb Hind III fragments. Kpn I and Hind III digested NCIMB 3351 genomic DNA was size fractionated by agarose gel electrophoresis and libraries in the plasmid pUC18 were prepared in *E. coli* JM101. Colony hybridization with TG46 resulted in the isolation of clones containing overlapping Kpn I and Hind III fragments. In addition to the complete coding region for G6PDH, these clones contained approximately 1.7 kb of 5' flanking (Kon I clones) and approximately 1.1 kb 3' flanking sequences (Hind III clones). Approximately 0.8 kb downstream of the gene was a unique Mlu I site.

The 2.5 kb Hind III fragment, containing all but the first 20 codons of the gene, was cloned between the unique Hind III and NcoI sites of pKK233-2 (Pharmacia Molecular Biologicals, Piscataway, N.J.) along with a synthetic DNA duplex which spanned pKK233-2's unique Nco I and Hind III sites and encoded the first 20 amino acids of NCIMB 3351 G6PDH as derived from the DNA sequence of the cloned Kpn I fragment. The synthetic linker sequences were:

5'-C-ATG-GTT-GCA-GAA-ATC-AAA-ACA-TTA-GTT-ACT-TTT-TTT-GGT-GGA-ACT-GGT-GAT-TTA-GCA-AAG-CGT-A-3' (SEQ ID NO:10) and, 5' AG-CTT-ACG-CTT-TGC-TAA-ATC-ACC-AGT-TCC-ACC-AAA-AAA-AGT-AAC-TAA-TGT-TTT-GAT-TTC-TGC-AAC 3' (SEQ ID NO:11). The resulting plasmid was transformed into JM101 or HB101 and expressed the wild type G6PDH from *Leuconostoc citreum* (NCIMB 3351). It was called 3351/pKK233-2.

By another method, G6PDH from American Type Culture Collection (ATCC) 12291 (*Leuconostoc mesenteroides*) was cloned by polymerase chain reaction amplification of the gene from genomic DNA and direct ligation of the restricted amplification product into an expression vector. The polymerase chain reaction (PCR) is described by Saiki, R. K., Scharf, S., Faloone, F., Mullis, K. B., Horn, G. T., Erlich, H. A., and Arnheim, N. in *Science* 230, 1350–1354 (1985) and in U.S. Pat. No. 4,683,202. The use of this technology in DNA cloning is described in U.S. Pat. No. 4,800,159. Further the use of thermostable DNA polymerase in this process is described in U.S. Pat. No. 4,889,818. Methods for accomplishing PCR are further described in "The Polymerase Chain Reaction" by Erlich, H. A., Gibbs, R., and Kazazian, Jr., H. H. eds. published by the Cold Spring Harbor Laboratory Press (1989), especially pages 1–31. In the specific G6PDH cloning described here, two oligos were designed for the PCR reaction to create the entire G6PDH coding region from amplification of ATCC 12291 genomic DNA. The 5' PCR oligo, 5'-T-TTT-TGG-GAT-CCA-TCC-ATG-GTT-TCA-GAA-ATC-AAG-ACG-TTA-GTA-ACT-TTC-TTT-GG-3' (SEQ ID NO:12) provides an internal Bam HI site, an internal Nco I site (which includes the ATG of the initiation codon) and sequence hybridizing to the first 38 bases of the coding region. The 3' PCR oligo, 5' T-TTT-TTC-TAG-ATT-AAG-TTA-ACC-TTT-AAA-CAC-CCA-AGC-ATC-ACC-ATT-GGC-AGC-CAA-TAA-TTT-ATC-GGA-TG 3' (SEQ ID NO:13) provided the coding sequence for the last 17 amino acids of the protein, a stop codon, and an internal Xba I site. ATCC 12291 genomic DNA was used as a template to amplify the desired fragment in 30 cycles, using 94° C. denaturation, 42° C. hybridization, and 72° C. synthesis. Taq polymerase was purchased from Perkin-Elmer Cetus (Norwalk, Conn.) and used in conjunction with the Perkin-Elmer Cetus, DNA Thermal Cycler 480. The expression vector, pKK233-2 (Pharmacia Molecular Biologicals, Piscataway, N.J.) was prepared by cleaving it at the Hind III site, filling in the overhanging ends with Klenow fragment and ligating in a phosphorylated Xba I linker (d(pCTCTAGAG) and d(pGCTCTAGAG) purchased from New England Biolabs, Beverly, Mass.). The order of restriction enzyme sites, from the trc promoter, was then Nco I, Pst I and Xba I. A 1.5 kb fragment that included the entire coding sequence of G6PDH, beginning with the ATG of the start codon, was isolated by complete digest with Xba I and partial digestion (in some strains, for example ATCC 12291, the G6PDH gene may contain an internal Nco I site) with Nco I and cloned into the modified, Nco I, Xba I-cut pKK233-2.

DNA Sequencing and amino acid sequences of G6PDH Genes

Once the gene for G6PDH has been obtained, its complete nucleotide sequence may be determined by the method of Sanger, et al. (*Proc. Natl. Acad. Sci., USA* 74 (12), 5463–5467 (1977)). Such sequencing may be accomplished by the transfer of the DNA clones described above into suitable commercially available M13 vectors such as M13mp18 or M13mp19 (Messing, J., "Methods in Enzymology" 101 (part C); Recombinant DNA pp. 20–78. R. Wu, L. Grossman, K. Moldave (eds.) Academic Press, New York and Yanisch-Perron, C., Vieira, J. and Messing, J. *Gene* 33, 103–119 (1985). Alternatively, techniques have been published and are well known in the literature for determining the nucleotide sequence of a DNA directly from a double stranded vectors (see for example, Ku-chuan Hsiao, *Nucleic Acids Res.* 19 (10), 2787 (1991)).

DNA sequencing was accomplished using a Sequenase Kit (United States Biochemical Corp., Cleveland, Ohio) according to the instructions provided by the manufacturer and the above references. In addition to sequencing primers located within the cloning vector, other oligodeoxynucleotides useful as DNA sequencing primers for G6PDH from ATCC 12291 are described in Table 3. The DNA sequence of the G6PDH gene derived from *Leuconostoc mesenteroides* (ATCC 12291) is shown in FIG. 1. The DNA sequence of the G6PDH gene derived from *Leuconostoc citreum* (NCIMB 3351) and its flanking DNA is shown in FIG. 3. Additional DNA sequencing and hybridization primers may be readily deduced from the sequences.

Once the DNA sequence of the G6PDH gene was determined, the amino acid sequence of the gene could be deduced from the genetic code. The amino acid sequence of the G6PDH enzyme from *Leuconostoc mesenteroides* (ATCC 12291) is shown in FIG. 2. The amino acid sequence of the G6PDH enzyme from *Leuconostoc citreum* (NCIMB 3351) is shown in FIG. 4. Amino terminal and tryptic fragment amino acid sequencing of authentic G6PDH enzyme isolated from these strains showed that the correct and complete genes had been isolated by the genomic and PCR cloning. In some cases, recombinant proteins expressed in *E. coli* have an additional methionine residue at the amino terminus of the protein. The presence or absence of an amino terminal methionine had no significant detrimental effect on the specific activity or conjugation properties of the proteins described in this invention.

TABLE 3

DNA Sequencing Primers for G6PDH from ATCC 12291.

| Name | Sequence[a] | 5' start position[b] | Orientation[c] | |
|---|---|---|---|---|
| 271 | GAA-CGC-CTC-AGC-TTG-TGC | 273 | − | (SEQ ID NO:14) |
| 272 | GAC-ACA-GCC-GGT-GCA-TTG | 730 | + | (SEQ ID NO:15) |
| 273 | GCT-AGT-AGG-CCT-TCT-GAC | 458 | − | (SEQ ID NO:16) |
| 274 | GTG-GTG-CTT-TAT-CTG-CGG | 1417 | − | (SEQ ID NO:17) |
| 281 | CGT-CAG-ATA-CAG-TCC-AAC-C | 1264 | − | (SEQ ID NO:18) |
| 282 | CCG-CAG-ATA-AAG-CAC-CAC | 1400 | + | (SEQ ID NO:19) |
| 283 | CAC-GTT-CTT-CGA-CAC-CCA | 718 | − | (SEQ ID NO:20) |
| 285 | GCG-CTT-ACC-TGA-ACG-GAC | 1065 | − | (SEQ ID NO:21) |
| 287 | GCA-CCA-TAT-TGT-GCA-CGA-AC | 920 | − | (SEQ ID NO:22) |

TABLE 3-continued

DNA Sequencing Primers for G6PDH from ATCC 12291.

| Name | Sequence[a] | 5' start position[b] | Orientation[c] | |
|---|---|---|---|---|
| 288 | CCT-TCA-TCG-CCG-GCG-AAT-T | 989 | + | (SEQ ID NO:23) |
| 294 | CCA-AAG-GGT-GCT-ATC-GAA | 1171 | + | (SEQ ID NO:24) |
| 295 | GAC-ACA-GCT-GCC-GAA-CTC | 511 | + | (SEQ ID NO:25) |
| 296 | GAC-GTA-ACA-GAT-GCT-GCT | 301 | + | (SEQ ID NO:26) |
| 297 | GGT-GGC-ACT-GGT-GAC-TTG | 82 | + | (SEQ ID NO:27) |
| 300 | GAA-AAC-TGA-TGG-GTA-AAG-C | 129 | − | (SEQ ID NO:28) |
| 301 | TCA-GTT-GCG-CCA-CGT-TTC | 397 | + | (SEQ ID NO:29) |
| 302 | CGC-AGC-CTT-TAA-TGC-TTT-G | 846 | + | (SEQ ID NO:30) |
| 303 | GCT-GAC-TGG-AAT-GGC-GTT | 1339 | + | (SEQ ID NO:31) |
| 364 | ACG-CCA-GAA-CCA-TAC-GAA | 1279 | + | (SEQ ID NO:32) |

[a]DNA sequences are written 5' to 3'
[b]Numbering refers to FIG. 1.
[c]Oligodeoxynucleotides reading 5' to 3' directly into amino acid sequence such as shown FIG. 2 are designated +; oligodeoxynucleotides complimentary to the nucleotide sequence in FIG. 1 are designated − in orientation.

Mutagenesis of Recombinant Leuconostoc G6PDH

Several methods are available for the introduction of specific nucleotide changes in cloned genes. These methods, including that of Kunkel, T. A. *Proc. Natl. Acad. Sci., U.S.A.* 82, 488–492 (1985), are reviewed and described in detail in most laboratory manuals of molecular biology. Specific methodologies can be found in "Current Protocols in Molecular Biology", Ausubel, F. M., Brent, R., Kingston, R. E., Morre, D. D., Seidman, J. G., Smith, J. A., and Struhl, K. eds. published by Greene Publishing Associates and Wiley-Interscience, John Wiley & Sons, New York, especially pages 8.0.1 to 8.4.7 and in particular the section 8.1 entitled Oligonucleotide-Directed Mutagenesis without Phenotypic Selection. An additional source of methodology for the introduction and characterization of specific mutation can be found in "Molecular Cloning A Laboratory Manual", by Sambrook, J., Fritsch, E. F., and Maniates, T. published by Cold Spring Harbor Laboratory Press, 2nd edition, Chapter 15.51 to 15.80, especially 15.74 through 15.79.

The M13 site-specific mutagenesis techniques described above were employed in the isolation of the mutants listed in Table 4. The nomenclature used there to designate the mutants gives the one letter amino acid code for the native or "precursor" amino acid, the position of that amino acid along the polypeptide chain, and then the one letter amino acid code for the amino acid that replaces the precursor residue in the mutant form of the enzyme. Thus, for example "K343R" means that the K (lysine) normally present at amino acid position 343 has been replaced by R (arginine).

TABLE 4

Mutagenic oligodeoxynucleotides for M13 site-specific mutagenesis of G6PDH genes.

| Mutant | Strain | Sequence [a] | Oligo No. | |
|---|---|---|---|---|
| K343R | ATCC 12291 | CTT-AGC-TGC-TCG-TCA-GAC-ACG | 487 | (SEQ ID NO:33) |
| | | GGT-TGA-TAT-CGT-CTT-TAA- | 526 | (SEQ ID NO:34) |
| | | GGC-TGG-TAC-CTT-TAA-CTT-TG | | |
| K338R | ATCC 12291 | GTC-CCA-TTC-TAC-GTA-CGT- | 488 | (SEQ ID NO:35) |
| | | TCA-GGT-CGT-CGC-TTA-CGT-G | | |
| K282R | ATCC 12291 | GAA-GTT-AAC-CGT-TAC-TTT- | 508 | (SEQ ID NO:36) |
| | | GTT-AGA-GCT-CAA-TAT-GGT-G | | |
| K461R | ATCC 12291 | AAG-CAC-CAC-TCG-AGA-CTT- | 509 | (SEQ ID NO:37) |
| | | ACC-GTT-CGG-GCT-CAA | | |
| K472R | ATCC 12291 | GCA-TCC-GAT-CGT-TTA-TTG- | 511 | (SEQ ID NO:38) |
| | | GCT-G | | |
| K5R | NCIMB 3351 | GTT-CGA-GAA-ATC-CGT-ACA- | 534 | (SEQ ID NO:39) |
| | | CTA-GTT-ACT-TT | | |
| K454R | ATCC 12291 | CGT-TTA-TAC-TGC-AGA-TCG- | 537 | (SEQ ID NO:40) |
| | | TGC-ACC-ACT-TG | | |
| K182C | ATCC 12291 | CTA-CGT-GGG-TTG-CGA- | 569 | (SEQ ID NO:41) |
| | | AAT-GGT-TC | | |
| K182C | NCIMB 3351 | GAT-CAT-TAC-CTG-GGT- | 570 | (SEQ ID NO:42) |
| | | TGC-GAA-ATG-GTC-C | | |

TABLE 4-continued

Mutagenic oligodeoxynucleotides for M13 site-specific mutagenesis of G6PDH genes.

| Mutant | Strain | Sequence [a] | Oligo No. |
|---|---|---|---|
| L180C | ATCC 12291 | CTA-TTC-CGT-ATT-GAC-CAC-TAC-TGT-GGT-AAG-GAA-ATG-GTT-CAA-AAC-ATT-GCT-GCC-C | 514 (SEQ ID NO:43) |
| K252R | NCIMB 3351 | CTT-GCT-ATG-GAA-CGT-CCA-GAT-TCA | 630 (SEQ ID NO:44) |
| K252C | NCIMB 3351 | CTT-GCT-ATG-GAA-TGC-CCA-GAT-TCA | 632 (SEQ ID NO:45) |
| A52K | NCIMB 3351 | ATT-TGA-CTG-ATA-AGG-AAT-TCA-AGC-A | 660 (SEQ ID NO:46) |
| K128R | NCIMB 3351 | CTG-TGG-CAC-CGC-GGT-TCT-TTG-GGA-CAA-TTG-CAC-GTT-ATC-TCA-AG | 662 (SEQ ID NO:47) |
| K128R/K131R | NCIMB 3351 | GAC-AAT-TGC-ACG-TTA-TCT-CCG-TTC-AGA-GGG-T | 663 (SEQ ID NO:48) |
| K77R | NCIMB 3351 | TGA-AAA-GTG-TTC-GAT-GAA-TGC-CTC-GGC | 540 (SEQ ID NO:49) |
| K37C | ATCC 12291 | TAT-AAA-AAA-GGA-TAT-CTG-CAA-TGC-CAT-TTT-GCC-ATT | 678 (SEQ ID NO:50) |
| A2C | NCIMB 3351 | GAC-CAT-GGT-TTG-CGA-AAT-CAA-AAC-ATT-AG | 738 (SEQ ID NO:51) |

[a]Sequences are written 5' to 3'.

Besides site specific mutagenesis in M13 vectors, specific mutations can also be introduced in plasmid DNA by PCR. Higuchi, R., Krunmmel, B., and Saiki, R.K. have described these techniques in *Nucleic Acids Res.* 16(15), 7351–7367 (1985). This technique has the advantage that no transfer of genes between M13 vectors and plasmid expression vectors (such as pKK233-2 used here) is necessary. This mutagenesis technique involves the amplification in a first round of two independent fragments of the gene. These consist of flanking wild type primers derived from either the vector outside of the gene insert or from some distant position within the gene itself and complimentary internal primers located precisely at the site of the mutation. These internal primers contain wild type sequence except for the mutation and in some cases also a modified restriction site in the vicinity of the mutation. This latter feature allows detection of recombinant genes carrying the desired mutation after the ligation and transformation processes. Two separate amplification reactions consisting of either one of the flanking primers together with the mutant primer facing it on the other strand were carried out and the presence and quantity of the correct fragment was tested by electrophoresis.

These fragments were electrophoretically separated on SeaChem GTG grade agarose (FMC BioProducts, Rockland, Me.) and gel purified using Elu-Quik glass beads (Schleicher & Schuell, Keene, N.H.) according to the manufacturers' instructions. The purified DNAs were used as templates for a second round of PCR together with the original flanking primers in the same tube. Amplification of this mix led to production of a template from which a mutant fragment of DNA could be excised by restriction. Restriction sites were generally chosen so as to release a fragment of between 100–300 bp. Following agarose-gel purification, as above, this fragment could then be inserted into a precut vector from which had been removed the same wild type piece of DNA. Successful clones of mutant genes could be tested in several ways, including restriction analysis looking for the non-coding mutated site present in the original pair of primers as well as by direct sequencing of the region.

PCR reactions were performed in a buffer containing 10 mM Tris-HCl, pH 8.3, 2 mM $MgCl_2$, 50 mM KCl, 50 $\mu$M of each of the four normal deoxyribonucleoside triphosphates and 2.5 units of Amplitaq DNA polymerase (Perkin-Elmer Cetus, Norwalk, Conn.). Primers were generally approximately 1 $\mu$M in concentration. Cycling was as follows: 1 min at 94° C. followed by 30 cycles of 30 sec at 94° C., 30 sec at 50° C. and 1 min at 72° C. followed by 1 cycle of 30 sec at 94° C., 30 sec at 50° C. and 4 min at 72° C. after which reactions were stored at 4° C.

The PCR technique described above was employed to isolate the mutants listed in Table 5.

TABLE 5

Mutagenic oligodeoxynucleotides for PCR Site-specific mutagenesis of G6PDH genes.

| Mutant | Strain | Sequence[a] | Oligo No. |
|---|---|---|---|
| K128R | ATCC 12291 | AGC-TAG-TAG-GCC-TTC-TGA-CTT-AAG-ATA-ACG-GGC-AAT-TGT-ACC | 451 (SEQ ID NO:52) |
| K131R | ATCC 12291 | AGC-TAG-TAG-GCC-TTC-TGA-ACG-AAG-ATA-TTT-GGC | 452 (SEQ ID NO:53) |
| K252R | ATCC 12291 | GAA-TGA-TTC-TGG-ACG-TTC-CAT-CGC-TAA | 469 (SEQ ID NO:54) |
| K252R | | TTA-GCG-ATG-GAA-CGT-CCA-GAA-TCA-TTC | 470 (SEQ ID NO:55) |
| K148R | ATCC 12291 | GAG-GTA-CCG-AAA-GGA-CGT-TCA-ATC | 471 (SEQ ID NO:56) |
| K148R | | GAT-TGA-ACG-TCC-TTT-CGG-TAC-CTC | 472 (SEQ ID NO:57) |
| K259R | ATCC 12291 | TCA-TTC-ACT-GAC-CGT-GAT-ATC-CGT-GCC | 477 (SEQ ID NO:58) |
| K259R | | GGC-ACG-GAT-ATC-ACG-GTC-AGT-GAA-TGA | 478 (SEQ ID NO:59) |
| K265R | ATCC 12291 | ATT-CGT-GCC-GCG-CGC-AAC-GCA-GCC-TTT | 479 (SEQ ID NO:60) |
| K265R | ATCC 12291 | AAA-GGC-TGC-GGT-GCG-CGC-GGC-ACG-AAT | 480 (SEQ ID NO:61) |
| K128R | NCIMB 3351 | ACT-ATC-AGC-TAG-CAA-ACC-CTC-TGA-CTT-GAG-ATA-ACG-TGC-AAT-TGT | 491 (SEQ ID NO:62) |
| K131R | NCIMB 3351 | ACT-ATC-AGC-TAG-CAA-ACC-CTC-TGA-ACT-GAG-ATA-TTT | 492 (SEQ ID NO:63) |
| K282R | NCIMB 3351 | GCC-GAA-GTC-AAC-CGT-TAT-TTC-GTC-CGT | 493 (SEQ ID NO:64) |
| K338R | NCIMB 3351 | GAT-ATC-GAC-ACG-TGT-TTG-TTT-AGC-AGC-TAA-ACG-ACG-GCC-TGA-ACG | 494 (SEQ ID NO:65) |
| K343R | NCIMB 3351 | GAT-ATC-GAC-ACG-TGT-TTG-ACG-AGC-AGC-TAA-ACG | 495 (SEQ ID NO:66) |
| K352R | NCIMB 3351 | AAA-CAA-ACA-CGT-GTC-GAT-ATC-GTC-TTC-CGT-GCT-GGT-ACC | 496 (SEQ ID NO:67) |
| K454R | NCIMB 3351 | ATT-TCA-GCT-GTC-TAC-ACT-GCT-GAT-CGT-GCA-CCA-CTT | 497 (SEQ ID NO:68) |
| K461R | NCIMB 3351 | TGC-TTC-AGG-TCC-CAT-GGA-ACC-TGA-ACG-GTA-TGT-TTC | 498 (SEQ ID NO:69) |
| K5R | NCIMB 3351 | ACT-AAC-TAA-TGT-ACG-GAT-ATC-TGC-AAC | 500 (SEQ ID NO:70) |
| K5R | | GTT-GCA-GAT-ATC-CGT-ACA-TTA-GTT-ACT | 501 (SEQ ID NO:71) |
| K182R | NCIMB 3351 | CCG-AAG-AGC-TCC-AAC-GTG-ACT-TAG-AA | 502 (SEQ ID NO:72) |
| K182R | | TTC-TAA-GTC-ACG-TTG-GAG-CTC-TTC-GG | 503 (SEQ ID NO:73) |
| A77E | NCIMB 3351 | TGA-AAA-GTG-TTC-GAT-GAA-TGC-CTC-GGC | 540 (SEQ ID NO:74) |
| A77E | | GCC-GAG-GCA-TTC-ATC-GAA-CAC-TTT-TCA | 542 (SEQ ID NO:75) |
| A52D | NCIMB 3351 | GAT-TTG-ACT-GAT-GAT-GAG-TTC-AAG-CAA | 541 (SEQ ID NO:76) |
| A52D | | TTG-CTT-GAA-CTC-ATC-ATC-AGT-CAA-ATC | 543 (SEQ ID NO:77) |

TABLE 5-continued

Mutagenic oligodeoxynucleotides for PCR Site-specific mutagenesis of G6PDH genes.

| Mutant | Strain | Sequence[a] | Oligo No. |
|---|---|---|---|
| A155D/ K162R | NCIMB 3351 | TAA-GTC-GTT-TTG-GAG-CTC-TTC-GGC-AGT-GTC-GTA-TGA | 544 (SEQ ID NO:78) |
| A155D/ K162R | | TCA-TAC-GAC-ACT-GCC-GAA-GAG-CTC-CAA-AAC-GAC-TTA | 545 (SEQ ID NO:79) |
| A63K | NCIMB 3351 | GTT-CGT-GAA-TCA-ATC-AAG-GAC-TTT-ACT-GAA-G | 546 (SEQ ID NO:80) |
| A63K | | CTT-CAG-TAA-AGT-CCT-TAA-TTA-ATT-CAC-GAA-C | 547 (SEQ ID NO:81) |
| A52C | NCIMB 3351 | CAG-CGT-TTG-ACT-GAT-TGT-GAG-TTC-AAG-CAA | 606 (SEQ ID NO:82) |
| A52C | | TGC-TTG-AAC-TCA-CAA-TCA-GTC-AAA-TC | 607 (SEQ ID NO:83) |
| D48A/ A52C | NCIMB 3351 | ACA-GCA-CGT-CAG-GCT-TTG-ACT-GAT-TGT-GAC-TTC-AAG-CAA | 608 (SEQ ID NO:84) |
| D48A/ A52C | | TGC-TTG-AAC-TCA-CAA-TCA-GTC-AAA-GCC-TGA-CGT-GC | 609 (SEQ ID NO:85) |
| Q47A/ A48C | ATCC 12291 | GGA-ACG-GCC-CGT-GCA-TGC-CTC-AAT-GA | 652 (SEQ ID NO:86) |
| Q47A/ A48C | | TCA-TTG-AGG-CAT-GCA-CGG-GCC-GTT-CC | 653 (SEQ ID NO:87) |
| D52C | ATCC 12291 | CAA-TGA-TTG-CAG-GTT-CAA-ACA-A | 654 (SEQ ID NO:88) |
| D52C | | TTG-TTT-GAA-CTC-GCA-ATC-ATT-G | 655 (SEQ ID NO:89) |
| K55C | ATCC 12291 | GAT-GAC-GAG-TTC-TGC-CAA-TTG-GTT-CG | 658 (SEQ ID NO:90) |
| K55C | | CGA-ACC-AAT-TGG-CAG-AAC-TCG-TCA-TC | 659 (SEQ ID NO:91) |
| Q56C | ATCC 12291 | GAT-GAC-GAG-TTC-AAA-TGC-TTG-GTT-CAT-G | 670 (SEQ ID NO:92) |
| Q56C | | CAC-GAA-CCA-AGC-ATT-TGA-ACT-CGT-CAT-C | 671 (SEQ ID NO:93) |
| E53C | ATCC 12291 | CAA-TGA-TGA-CTG-CTT-CAA-ACA | 672 (SEQ ID NO:94) |
| E53C | | TGT-TTG-AAG-CAG-TCA-TCA-TTG | 673 (SEQ ID NO:95) |
| Q47C | ATCC 12291 | GGA-ACG-GCC-CGT-TGC-GCC-CTC-AAT-GAT-GAC-GAG-TTC | 674 (SEQ ID NO:96) |
| Q47C | | GAA-CTC-GTC-ATC-ATT-GAG-GGC-GCA-ACG-GGC-CGT-TCC | 675 (SEQ ID NO:97) |
| L49C | ATCC 12291 | GGA-ACG-GCC-CGT-CAA-GCC-TGC-AAT-GAT-GAC-GAG-TTC | 676 (SEQ ID NO:98) |
| L49C | | GAA-CTC-GTC-ATC-ATT-GCA-GGC-TTG-ACG-GGC-CGT-TCC | 677 (SEQ ID NO:99) |
| R46C | ATCC 12291 | GGA-ACG-GCC-TGC-CAA-GCC-CTC-AAT-GAT-GAC-GAG-TTC | 698 (SEQ ID NO:100) |
| R46C | | GAA-CTC-GTC-ATC-ATT-GAG-GGC-TTG-GCA-GGC-CGT-TCC | 699 (SEQ ID NO:101) |
| N50C | ATCC 12291 | CAA-GCC-CTC-TGC-GAT-GAC-GAG-TTC-AAA-CA | 700 (SEQ ID NO:102) |
| N50C | | TGT-TTG-AAC-TCG-TCA-TCG-CAG-AGG-GCT-TG | 701 (SEQ ID NO:103) |
| D51C | ATCC 12291 | CAA-GCC-CTC-AAT-TGC-GAC-GAG-TTC-AAA-CA | 705 (SEQ ID NO:104) |
| D51C | | TGT-TTG-AAC-TCG-TCG-CAA-TTG-AGG-GCT-TG | 706 (SEQ ID NO:105) |

TABLE 5-continued

Mutagenic oligodeoxynucleotides for PCR Site-specific mutagenesis of G6PDH genes.

| Mutant | Strain | Sequence[a] | Oligo No. |
|---|---|---|---|
| F54C | ATCC 12291 | GAT-GAC-GAA-TGC-AAA-CAA-TTG-GTT-CGT-G | 707 (SEQ ID NO:106) |
| F54C | | CAC-GAA-CCA-ATT-GTT-TGC-ATT-CGT-CAT-C | 708 (SEQ ID NO:107) |
| K128C | ATCC 12291 | ACA-ATT-GCC-TGC-TAT-CTT-AAG-TCA-GAA-GGT-CTA-CT | 709 (SEQ ID NO:108) |
| K128C | | AGT-AGA-CCT-TCT-GAC-TTA-AGA-TAG-CAG-GCA-ATT-GT | 710 (SEQ ID NO:109) |
| K131C | ATCC 12291 | GCC-AAA-TAT-CTT-TGC-TCA-GAA-GGT-CTA-CTA-GCT-G | 711 (SEQ ID NO:110) |
| K131C | | CAG-CTA-GTA-GAC-CTT-CTG-AGC-AAA-GAT-ATT-TGG-C | 712 (SEQ ID NO:111) |
| L57C | ATCC 12291 | GAT-GAC-GAG-TTC-AAA-CAA-TGC-GTT-CGT-G | 752 (SEQ ID NO:112) |
| L57C | | CAC-GAA-CGC-ATT-GTT-TGA-ACT-CGT-CAT-C | 753 (SEQ ID NO:113) |
| V58C | ATCC 12291 | GAT-GAC-GAG-TTC-AAA-CAA-TTG-TGC-CGT-G | 754 (SEQ ID NO:114) |
| V58C | | CAC-GGC-ACA-ATT-GTT-TGA-ACT-CGT-CAT-C | 755 (SEQ ID NO:115) |
| R59C | ATCC 12291 | GAC-GAG-TTC-AAA-CAA-TTG-GTT-TGC-GAT-TCA | 756 (SEQ ID NO:116) |
| R59C | | TGA-ATC-GAC-AAC-CAA-TTG-TTT-GAA-CTC-GTC | 757 (SEQ ID NO:117) |
| D60C | ATCC 12291 | GAC-GAG-TTC-AAA-CAA-TTG-GTT-CGT-TGC-TCA-ATT | 758 (SEQ ID NO:118) |
| D60C | | AAT-TGA-GCA-ACG-AAC-CAA-TTG-TTT-GAA-CTC-GTC | 759 (SEQ ID NO:119) |

[a]Sequences are written 5' to 3'.

In the case of the K21R, K19R, K282R, K454R, and K472R mutants in NCIMB 3351 a unique Bam HI site approximately 0.3 kb upstream of the Nco I site in 3351/pKK233-2 was used to move the entire gene including pKK233-2's trc promoter and NCIMB 3351 G6PDH gene terminator, on an approximately 2.4 kb Mlu I-Bam HI fragment from 3351/pKK233-2 into M13um30 (International Biotechnologies, Inc., New Haven, Conn.). This construction, called 3351/um30, allowed site-directed mutagenesis by primer extension essentially according to the methods of Zoller, M. J. and Smith, M. in *Methods Enzymol.* 100, 468–500 (1983). Single-stranded DNA template from this 3351/um30 clone corresponded to the sense (coding) strand. For this reason the mutagenic oligodeoxynucleotides used below correspond to the anti-sense strand. Individual K19R, K21R, K282R, K454R and K472R mutants were isolated using the following oligonucleotides (asterisks denote changes from wild type sequence and introduced, or destroyed, restriction sites are noted):

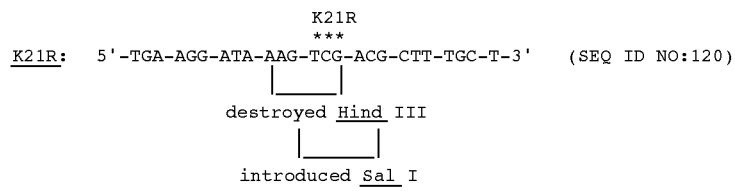

K21R: 5'-TGA-AGG-ATA-AAG-TCG-ACG-CTT-TGC-T-3'  (SEQ ID NO:120)

Note that K21R 3351/um30 single-stranded template was used for the following K19R mutagenesis to create the double mutant.

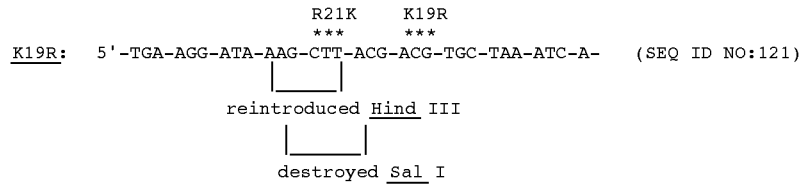

K19R: 5'-TGA-AGG-ATA-AAG-CTT-ACG-ACG-TGC-TAA-ATC-A-  (SEQ ID NO:121)

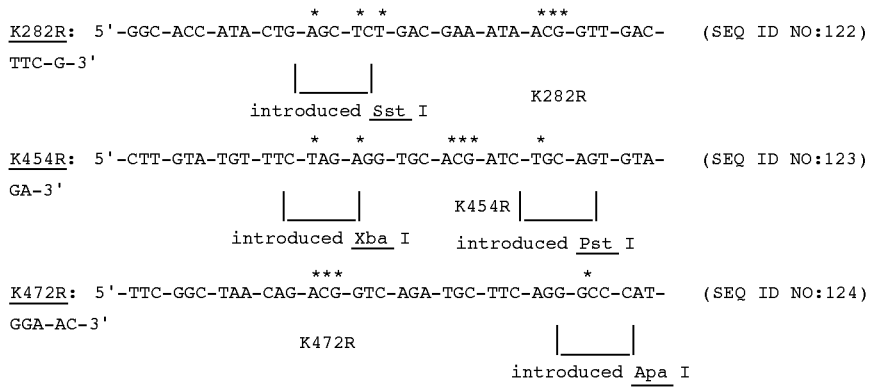

Introduced or destroyed restriction sites were designed to be silent at the protein level except in cases where they also result in the desired K to R or R to K changes (i.e. K21R and K19R oligodeoxynucleotides). The sites are used as an aid in isolating the desired mutant from a mixed mutant and wild type population. Following mutagenesis in M13, the plaque-purified, sequence verified clone was redigested with Mlu I and Bam HI and the 2.4 kb fragment reintroduced into a suitably digested pKK233-2 vector. The introduced or destroyed restriction sites, described above, were used to screen for the mutant 3351/pKK233-2.

The double mutant K19R/K282R was obtained in the following manner. K19R/pKK233-2 was digested with Nhe I and Kpn I. The large fragment (less approximately 0.65 kb) was isolated. K282R/pKK233-2 was digested with Nhe I and Kpn I, the approximately 0.65 kb fragment (containing K282R and the Sst I site) isolated. These two fragments were ligated and transformed into *E. coli* JM101. Plasmids from the resulting transformants were prepared and screened for K282R's Sst I site, indicating the presence of the double mutation.

The double mutant K454R/K472R was obtained in the following manner. K472R/pKK233-2 was digested with Nco I and Bam HI. The large fragment (less approximately 0.3 kb pKK233-2 Bam HI-Nco I and approximately 1.4 kb Nco I-Nco I fragments) isolated. K454R/pKK233-2 was digested with Kpn I and Nco I, the approximately 0.33 kb fragment (containing K454R and its linked Xba I and Pst I sites) isolated. Wild type 3351/pKK233-2 was digested with Bam HI and Kpn I and the approximately 1.4 kb fragment isolated. These three fragments were ligated and transformed into *E. coli* JM101. The resulting transformants screened for K454R's Xba I site.

A quadruple mutant, called "4X" or "quad", was constructed from the two double mutants above in the following manner. K19R/K282R/pKK233-2 was digested with Mlu I and Kpn I, the large fragmented (less approximately 1.2 kb) isolated. K454R/K472R/pKK233-2 was digested with Mlu I and Kpn I, the approximately 1.2 kb fragment (containing K454R, K472R, Pst I, Xba I and Apa I sites) isolated. These two fragments were ligated and transformed into *E. coli* JM101. The resulting transformants were screened for K472R's Apa I site. The resulting "quad" mutant was then K19R/K282R/K454R/K472R.

Contrary to what might have been expected, multiple lysine to arginine substitutions in G6PDH frequently resulted in enzymes, which when conjugated, showed improved specific activity, stability, and better immunoassay performance as compared with precursor enzyme or mutant enzymes containing only individual single mutations. Thus, for example, the quad enzyme performs better, and is preferred, over precursor G6PDH or mutant G6PDHs containing only each of the single mutations that make it up.

Tables 4 and 5 above describe a number of individual and some multiple mutations that can be made in precursor G6PDH. These mutations may also be made in the quad mutant so as to result in G6PDHs with higher numbers of mutations. For example, using the above described methods, K128R can be introduced into the quad to result in a mutant G6PDH that is K19R/K128R/K282R/K454R/K472R. This mutant is called the "pent" or 5X". K15R and K461R can be introduced into the quad so as to result in K5R/K19R/K282R/K454R/K461R/K472R. This mutant is called the "hex" or "6X". Further, K128R can be added to the hex to result in a mutant that is K5R/K19R/K128R/K282R/K454R/K461R/K472R. This mutant is called the "sept" or "7X". Additionally, K128R/K131R can be introduced into the hex to result in a mutant G6PDH that is K5R/K19R/K128R/K131R/K282R/K454R/K461R/K472R. This mutant is called the "oct" or "8X", and so on. Multiple lysine to arginine mutations at any two or more naturally occurring lysines are desirable and within the scope of this invention with the exception of positions 21 and 182 (in ATCC 12291 and NCIMB 3351). Mutational substitution of arginine at these latter two positions typically result in lowered specific activity and poor immunoassay performance. In all cases, subsequent DNA sequencing of the G6PDH gene was used to verify the position and nature of all single and multiple mutants.

Isolation and Purification of Recombinant G6PDH

The isolation and purification of G6PDH from *Leuconostoc mesenteroides* was described by Olive, C. and Levy, H. R. *Biochemistry* 6 (3), 730–736 (1967). Larger quantities of the protein were accommodated by the modification to this procedure described in Haghighi, B., Flynn, T. G., and Levy, H. R. *Biochemistry* 21 (25), 6415–6420 (1982), specifically page 6416 column 1. A more rapid procedure which is useful is that described by Hey, Y. and Dean, P. D. G. *Biochem. J.* 209, 363–371 (1983). The above methods were successful in enabling the isolation and purification of the mutant G6PDHs described in this invention.

Example I

The quinidine analog O-carboxypentylcupreidine was activated by reaction with 1 equivalent of N-hydroxysuccinimide (NHS) and 1.1 equivalent of 1-ethyl- 3-(3-dimethylaminopropyl)-carbodiimide (EDAC) in dimethylformamide (DMF). The activation reaction was stirred for 72 hours at 4° C. The concentration of the carboxypentylcupreidine was 0.16 M.

A solution containing 0.5 mg of "8X" G6PDH show with 2 mg glucose-6-phosphate disodium salt and 4 mg of NADH in 100 µl of 0.1 M sodium bicarbonate buffer was prepared. To this was slowly added 25 µl of DMF while stirring on ice. A total of 7.5 µl of the activated carboxypentylcupreidine was then added in several aliquots and allowed to react for 1 hour/addition in order to reach the desired endpoint of >70% maximum inhibition.

The enzyme was monitored in accordance with the assay described below for determining % deactivation. The % inhibition was determined by adding an excess of anti-quinidine antibody and assaying the enzyme activity according to the method described below. The conjugate was worked up by chromatography over Bio-Gel P6-DG (Bio Rad) (6 ml column), employing 0.1 M sodium bicarbonate buffer (pH 8.1) as eluant, collecting 200 µl fractions. These fractions were pooled to give a total volume of 1.2 ml.

The components of enzyme assays used to monitor the progress of the conjugation were as follows:

Samples from the conjugation reaction were diluted into a buffer containing 0.2 M Tris-Cl and 0.1% bovine serum albumin (BSA) at pH 8.0 prior to assay. Dilutions were made such that the rate in the assay described was between 500 and 1000 mΔA/min. The added assay buffer contained 0.055 M Tris-Cl, 0.5% NaCl, and 0.01% v/v Triton X–100 at a pH of 8.1. The substrate solution contained 0.007 M G6P and 0.0028 M NAD$^+$ at pH 5.5. A Gilford Stasar III microsample spectrophotometer is employed with a Thermocuvette with a flow cell.

The protocol employed for carrying out an assay is as adapted from U.S. Pat. No. 4,238,389, example 7, column 8. A 50 µl aliquot of substrate solution is drawn up into a diluter and dispensed with 250 µl of assay buffer into a 2 ml Croan cup, followed by a 50 µl aliquot of assay buffer (or anti-quinidine antibody solution containing an excess of antibody in cases where % inhibition in being determined) with 250 µl of the assay buffer. A 50 µl aliquot of enzyme solution and 250 µl of assay buffer are then added to the Croan cup. Immediately after the enzyme addition, the entire sample is aspirated into the flow cell. After 15 seconds, a first reading is taken, followed by a second reading, after a 45 second interval from aspiration. The results in terms of deactivation and inhibition are reported in Table 6.

The low deactivation achieved in this conjugation (30%) compares very favorably with conjugations of commercial enzyme, in which deactivations of 45–60% are observed. Lower deactivation is often correlated with enhanced thermal stability of the conjugate (see example 3 below).

TABLE 6

QUINIDINE CONJUGATION RESULTS

| Sample | Total Hapten (µl) | % Deactivation | % Inhib. |
|---|---|---|---|
| 1 | — | | |
| 2 | 5 | 15 | 56 |
| 3 | 7.5 | 30 | 71 |

Example II

A preparation of 3',5'-diiodo-4'-hydroxy-3-phenylpropionic acid (DIHPPA) was activated by reaction with 1 equivalent of N-hydroxysuccinimide and 1 equivalent of (EDAC) in dimethylformamide (DMF). The activation reaction was stirred for 24 hours at 4° C. The concentration of the DIHPPA was 0.05 M.

A solution containing 0.25 mg of G6PDH (wild type or variant as listed in Table 7) with 4 mg glucose-6-phosphate disodium salt and 4 mg of NADH in 100 µl of 0.55 M Tris-Cl (pH 8.0) buffer was prepared. To this was slowly added 25 µl of DMF while stirring on ice. A total of 11–13 µl of the activated DIHPPA was then added in several aliquots and allowed to react for 1 hour/addition in order to reach the desired endpoint of 65–75% maximum inhibition. The procedures described above were used for monitoring enzyme activity, determining maximum inhibition (using an anti-thyroxine pAb), and working up the conjugate. The final results of these conjugations are reported in Table 7.

These conjugates were diluted and used in an immunoassay for thyroxine as described below. The conjugates made from variant G6PDH's showed larger standard curves over the range of thyroxine concentrations tested (See Table 8). Larger standard curves often give more reproducible and precise results in immunoassays.

The solutions used for dilution of conjugates and antibodies are: Antibody Diluent: 0.009 M NAD$^+$, 0.0011 M PEG 6000, 0.0095 M Glucose-6-phosphate, monosodium, 0.00026 M ANS (8-Analino-1-naphthalene-sulfonic acid), 0.0165 M Tris, 0.1 M NaCl, 0.000038 M Plurafac A39, 0.0013 M EDTA, 0.0000067 M BGG (Bovine gamma globulin), 0.098 M Mannitol, 0.000049 M Thimerosal, 0.053% gentamicin, 0.0120% Dow Corning AF silicone, at pH 6.0. Conjugate Diluent: 0.0189 M glucose-6-phosphate, monosodium, 0.00018 M PEG 6000, 0.073 M Tris, 0.0634 M barbital, sodium, 0.00009 M BSA, 0.0234 M NaCl, 0.053w gentamicin, 0.012% Dow Corning AF silicone, 0.000049 M Thimerosal, 0.0027 M EDTA, at pH 8.0.

The conjugate was diluted to give an appropriate rate (180–190 mΔA/min) in the absence of antibody using the protocol described below. Antibody dilution was optimized to give the largest standard curve in that assay. Calibrators were made by diluting thyroxine into thyroxine-free human serum at concentrations of 0, 2, 4, 8, 12, and 20 µg/dL.

TABLE 7

DIHPPA CONJUGATION RESULTS

| Enzyme | Total Hapten (µl) | Final % Deactivation | Final % Inhib. |
|---|---|---|---|
| wild type 3351 [USB] | 11 | 64 | 73 |
| 3351-K5R | 11 | 63 | 72 |
| 3351-K19R | 11 | 47 | 75 |
| | 13 | 68 | 77 |
| 3351-K454,472R | 11 | 60 | 73 |
| 3351-K19,282, 454,472R (4X) | 13 | 71 | 75 |

Assays were performed on a COBAS MIRA automated analyzer (Roche Diagnostics) with the following protocol (run at 37° C.):

Step 1) 4 µl sample +55 µl water are combined in the instrument cuvette with 150 µl of anti-thyroxine solution
(325 second incubation)

Step 2) 75 µl of conjugate solution +20 µl of water are added to the cuvette
(25 second incubation)

Step 3) The enzymatic rate (change in absorbance at 340 nm) is measured for 125 seconds The rates measured for thyroxine samples are shown in Table 8.

TABLE 8

STANDARD CURVES FOR THYROXINE ASSAYS RATES (mAA/min)

| Sample (µg/dl Thyroxine) | precursor | K5R | K19R#1 | K454,472R | K19,282 454,472R |
|---|---|---|---|---|---|
| 0 | 143.3 | 137.2 | 135.8 | 136.1 | 126.9 |
| 2 | 147.0 | 141.3 | 139.8 | 141.4 | 131.0 |
| 4 | 151.5 | 144.9 | 144.9 | 145.7 | 136.7 |
| 8 | 159.0 | 153.1 | 154.5 | 154.3 | 147.2 |
| 12 | 164.6 | 161.2 | 160.5 | 161.2 | 154.3 |
| 20 | 174.6 | 174.1 | 173.8 | 173.3 | 167.7 |
| Total mod. | 31.3 | 36.9 | 38.0 | 37.2 | 40.8 |

Example III 3-ketodigoxigenin O-carboxymethyl oxime was activated by reaction with 1 equivalent of N-hydroxysuccinimide and 1.3 equivalent of dicyclohexylcarbodiimide in tetrahydrofuran (digoxigenin concentration was 0.043 M). The activation reaction was stirred for 24 hours at room temperature, then filtered through glass wool, dried, and stored at −20° C. under anhydrous conditions. The crude activated ester was worked up by chromatography over silica gel in 1:1 dichloromethane:acetonitrile. The resultant material was dried under a stream of Ar gas and stored at −20° C. under anhydrous conditions. Before use, a 1 mg sample of the activated ester was dissolved in 179 µl of anhydrous DMF to give a 0.01 M solution.

A solution containing 0.25 mg of G6PDH (wild type or variant as listed in Table 9) with 0.8 mg glucose-6-phosphate disodium salt in 100 µl of 0.1 M sodium bicarbonate buffer (pH 8.0) was prepared. To this was slowly added 25 µl of DMF while stirring on ice. A total of 8–12 µl of the activated 3-ketodigoxigenin O-carboxymethyl oxime was then added in several aliquots and allowed to react for 1 hour/addition in order to reach the desired endpoint of 50–57% maximum inhibition. The procedures described above were used for monitoring enzyme activity, determining maximum inhibition (using a rabbit antidigoxin antiserum), and working up the conjugate. The final results of the conjugations are shown in Table 9.

These conjugates were used in an immunoassay for digoxin as described below. The conjugates made from variant G6PDH's showed larger standard curves than did those made from wild type enzyme over the range of digoxin concentrations tested (See Table 10). Larger standard curves often give more reproducible and precise results in immunoassays.

These conjugates were used in a formulation in which the first reagent contained detergent in a low pH buffer for pretreatment of patient samples. This reagent also contained substrates: 0.0101 M NAD+, 0.0175 M Glucose-6-phosphate, monosodium, 0.176 M NaCl, 0.025 M Glycylglycine, 5.0% Sucrose, 0.025% Proclin 300, 1.6% Triton X-100, 0.004% Silicone, at pH 2.35. Rabbit antidigoxin antibodies were encapsulated in liposomes as described below. The solution used for dilution of conjugates and liposomes is 0.3 M Tris, 0.1% RSA (Rabbit Serum Albumin), 0.025% EDTA, 0.7 mg/L Pepstatin A, 10 TIU/L Aprotinin, 0.025% Proclin 300, 0.002% Silicone, at pH 8.25. The conjugate was diluted to give an appropriate rate (100 mAA/min) in the absence of antibody using the protocol described below. The dilution of antibody-containing liposomes was optimized to give the largest standard curve using the digoxin samples described next. Samples consisted of human serum with digoxin added to concentrations of 0, 0.5, 1, 2, 3, and 4 ng/ml.

Liposomes containing antibodies were prepared in the following way. Antibodies from rabbit serum were purified by ammonium sulfate precipitation (0.18 g/ml), reconstitution in 0.1 M Tris, 0.1% EDTA, pH 8.0, and dialysis against 0.1 M Tris, 0.1% EDTA, pH 8.0. Final protein concentration was 19 mg/ml. 1-Palmitoyl-2-Oleyl Phoshatidylcholine (POPC), 1-Palmitoyl-2-Oleyl Phoshatidylglycerol (POPG), and cholesterol (Avanti Polar Lipids) were combined in a ratio of 76:4:20 (w/w) for a total of 1.8 g. These lipids were dissolved in 13.68 ml chloroform. Using a 60° water bath to speed evaporation, the chloroform was evaporated under a stream of nitrogen gas to leave a thin film of lipids on the inside of the flask. 36 ml of tert-butanol was then added and the lipids redissolved at 60°. The lipid/tert-butanol solution was divided into aliquots containing 300 mg lipid in 6 ml volume. These aliquots were then frozen, lyophilized, and sealed under vacuum. To 300 mg of dried lipids was added 1.5 ml of antibody solution containing 28.5 mg protein. This solution was agitated on a vortex mixer for 15 minutes, then allowed to stand at room temperature for 30 minutes to fully hydrate the lipids. This suspension was then extruded ("The Extruder", Lipex Biomembranes Inc.) 3 times through stacked polycarbonate filters (pore sizes 1.0, 0.4, and 0.2 µm) using 400 psi of pressure (nitrogen gas). One ml of 0.1 M Tris buffer (pH 8.0) was added, and the extrusion was repeated 4 more times. The sample was then subjected to gel filtration on a Sephacryl 1000 column, and fractions were tested for both cholesterol (using Cholesterol/HP reagents from Boehringer Mannheim according to manufacturers protocol on the COBAS MIRA) and for the ability to inhibit enzymatic rate in the assay system described below. Those fractions containing liposomes were pooled and used in subsequent assays.

TABLE 9

DIGOXIN CONJUGATION RESULTS

| Enzyme | Total Hapten (µl) | Final % Deact. | Final % Inhib. |
|---|---|---|---|
| wild type 3351 | 9 | 40 | 53 |
| 3351-K282R | 9 | 21 | 53 |
| 3351-K454R | 9 | 28 | 54 |
| 3351-K454,472R | 8 | 30 | 56 |
| 3351-K19,282, 454,472R (4X) | 9 | 26 | 56 |

Assays were performed on a COBAS MIRA automated analyzer (Roche Diagnostics) with the following protocol (run at 37° C.):

Step 1) 36 µl sample +20 µl water are combined in the instrument cuvette with 150 µl of pretreatment/substrate solution
(275 second incubation)

Step 2) 75 µl of conjugate/liposome solution +20 µl of water are added to the cuvette
(75 second incubation)

Step 3) The enzymatic rate (change in absorbance at 340 nm) is measured for 350 seconds The rates measured for digoxin samples are shown in Table 10.

These conjugates were also subjected to thermal stress (30° C. for up to 44 days) to determine their stability. At selected intervals the enzyme activity was measured in assays as described above. The percentage of enzymatic activity remaining at each time point is shown in Table 11, from which it can be seen that the conjugates made from variant enzymes were more stable than those made from the wild type enzyme. This enhanced stability may be correlated with the decreased deactivation observed during the conjugation reaction as shown by a comparison of Tables 9 and 11.

TABLE 10

DIGOXIN STANDARD CURVES

| Sample (ng/dl digoxin) | precursor | K282R | K454R | K454, 472R | K19,282, 454,472R |
|---|---|---|---|---|---|
| 0 | 65.0 | 64.9 | 64.4 | 59.3 | 58.7 |
| 0.5 | 66.1 | 66.1 | 65.6 | 60.7 | 59.8 |
| 1.0 | 67.5 | 67.5 | 66.9 | 61.8 | 60.9 |
| 2.0 | 69.7 | 69.8 | 69.7 | 64.3 | 63.5 |
| 3.0 | 71.7 | 72.5 | 71.9 | 66.8 | 65.3 |
| 4.0 | 73.4 | 74.6 | 74.3 | 69.2 | 67.6 |
| Mod. | 8.3 | 9.7 | 9.9 | 9.9 | 8.9 |

TABLE 11

DIGOXIN CONJUGATE STABILITY

STUDY 1

| | Percent Activity Remaining | | | | |
|---|---|---|---|---|---|
| Conjugate | Day 1 | 6 | 13 | 22 | 26 | 44 |
| Wild-type | 100 | 86 | 78 | 71 | 68 | 58 |
| K282R | 100 | 92 | 85 | 78 | 75 | 65 |
| K454R | 100 | 90 | 83 | 76 | 73 | 63 |

STUDY 2

| | Percent Activity Remaining | | |
|---|---|---|---|
| Conjugate | Day 1 | 7 | 18 |
| Wild-type | 100 | 85 | 75 |
| K454,472R | 100 | 91 | 81 |
| K19,282,454,472R | 100 | 92 | 83 |

Example IV

A bromoacetyl derivative of 3-ketodigoxigenin O-carboxymethyl oxime was prepared as described in U.S. Pat. No. 4,727,022 (Example 4, columns 9 and 10). This material was stored either dry or as a 0.037 M solution in anhydrous DMF.

Samples of G6PDH variants 12291-D52C, 12291-E53C, and 12291-Q56C (250 µg in 0.5–2 ml) were dialyzed vs. 4 L of thoroughly degassed buffer containing 50 mM sodium phosphate and 1 mM EDTA at pH 7.0. The enzymes were then concentrated to 100 µl in Centricon-30 concentrators (Amicon). While stirring the enzyme solutions on ice, 5 µl of the bromoacetyl digoxin/DMF solution was added. This addition was followed by a flush with Argon gas, and the reaction container tightly sealed. After stirring the reaction for 24 hours at 4° C. in the dark, an additional 3.3 µl of the bromoacetyl digoxin/DMF solution was added. The reaction was stirred once again for 24 hours at 4° C. in the dark. Following this second incubation, the conjugate was worked up as described above, except phosphate/EDTA buffer was used in the chromatography.

These conjugates were used in combination with two kinds of antibodies to generate an immunoassay system. One set of antibodies were the anti-G6PDH monoclonal antibodies described in U.S. Pat. No. 4,727,022, especially antibody V1A1. The other antibodies used were monoclonal antidigoxin antibodies.

The conjugates were diluted into buffer containing 100 mM Tris-Cl, pH 7.8 at concentrations which would result in rates of 80–110 mΔA/min (in the absence of antibodies) in the assay described below. All antibodies were also diluted into this buffer. For this experiment approximately a 25-fold molar excess of anti-G6PDH and approximately 1 molar equivalent of anti-digoxin Ab (relative to conjugate) were used. A 0.05 M solution of glucose-6-phosphate was prepared in 0.5% NaCl, and the pH adjusted to 7.0 with NaOH. A 0.053 M solution of NAD$^+$ was prepared in 0.5% NaCl, and the pH adjusted to 5.9 with NaOH. Human serum samples containing 0, 0.5, 1, 2, 3, and 4 ng/ml of digoxin were used to generate standard curves.

Assays were performed on a COBAS MIRA-S automated analyzer (Roche Diagnostics) with the following protocol (run at 37° C.):

Step 1) 12 µl sample +38 µl water are combined in the instrument cuvette with 100 µl of anti-digoxin mAb (125 second incubation)

Step 2) 35 µl of conjugate solution +50 µl of G6P solution (diluent 1) are added to the cuvette (125 second incubation)

Step 3) 35 µl of anti-G6PDH solution +50 µl of NAD$^+$ (diluent 2) solution are added to the cuvette (100 second incubation)

Step 4) The enzymatic rate (change in absorbance at 340 nm) is measured for 125 seconds The rates measured for digoxin samples are shown in Table 12.

TABLE 12

DIGOXIN ASSAYS WITH CYSTEINE-LINKED DRUG ANALOG

| Digoxin concentration | Rates (mΔA/min) | | |
|---|---|---|---|
| in sample | D52C | E53C | Q56C |
| 0 | 42.1 | 39.7 | 56.6 |
| 0.5 ng/ml | 38.6 | 36.3 | 53.1 |
| 1 ng/ml | 35.6 | 32.9 | 49.1 |
| 2 ng/ml | 29.7 | 27.9 | 44.8 |
| 3 ng/ml | 25.6 | 22.2 | 39.8 |
| 4 ng/ml | 23.5 | 19.3 | 36.7 |
| Total modulation | 18.6 | 20.4 | 19.9 |

The patents and patent applications referred to in the above description are each incorporated herein by reference in their entirety.

Although the foregoing invention has been described in some detail by way of illustration and example for the purposes of clarity and understanding, it will be obvious that certain changes or modifications may be practiced within the scope of the appended claims. For example, many possible approaches to the cloning, expression, and mutagenesis of the G6PDH genes of the invention could be practiced by one ordinarily skilled in the art.

What is claimed is:

1. DNA encoding a mutant glucose-6-phosphate dehydrogenase (G6PDH) that is the expression product of a mutated DNA sequence encoding a G6PDH, the mutant G6PDH being derived from a precursor G6PDH by the deletion of, or substitution for, at least one lysine per subunit, or the insertion of, or substitution of, at least one cysteine per subunit, as compared to the precursor G6PDH wherein said mutant G6PDH has the ability to catalyze the oxidation of D-glucose-6-phosphate to D-glucono-δ-lactone-6-phosphate by utilizing either NAD$^+$ or NADP$^+$.

2. Expression vectors encoding the DNA of claim 1.

3. Host cells transformed with the expression vectors of claim 2.

4. The DNA of claim 1 wherein said substitution for lysine is the substitution of arginine for lysine.

5. The DNA of claim 1 wherein said substitution for lysine or said substitution of cysteine is at residues 35 through 70.

6. The DNA of claim 1 comprising the substitution of at least one cysteine per subunit.

7. DNA encoding a mutant glucose-6-phosphate dehydrogenase (G6PDH) that is the expression product of a mutated DNA sequence encoding a G6PDH, the mutant G6PDH being derived from a precursor G6PDH by the deletion, insertion or substitution of at least one amino acid per subunit as compared to the precursor G6PDH wherein said mutant G6PDH has the ability to catalyze the oxidation of D-glucose-6-phosphate to D-glucono-δ-lactone-6-phosphate by utilizing either NAD$^+$ or NADP$^+$ and wherein said amino acid is at a position sequentially proximate or spatially proximate to residues 2 through 5, residues 15 through 21, residues 35 through 70, residue 77, residues 128 through 162, residues 180 through 182, residues 252 through 282, residues 338 through 352 and residues 454 through 472 of the amino acid sequence of said precursor G6PDH and wherein said mutant G6PDH when conjugated to an sbp member has a higher enzymatic activity when the sbp member is not bound to its sbp partner relative to the corresponding property of the precursor G6PDH conjugated to a like number of sbp members.

8. Expression vectors encoding the DNA of claim 7.

9. Host cells transformed with the expression vectors of claim 8.

* * * * *